United States Patent
Gilligan et al.

(10) Patent No.: US 11,998,640 B2
(45) Date of Patent: Jun. 4, 2024

(54) ROOM TEMPERATURE STABLE ORAL CALCITONIN FORMULATION

(71) Applicants: PARK THERAPEUTICS, INC., Monmouth Junction, NJ (US); ENTERIS BIOPHARMA, INC, Boonton, NJ (US)

(72) Inventors: James P. Gilligan, Denville, NJ (US); George R. Maurer, Bell Mead, NJ (US); Aniruddha M. Railkar, Ambler, PA (US); Phillip Bauer, Highland Park, IL (US); Thomas A. Daggs, Verona, NJ (US); Paul P. Shields, North Caldwell, NJ (US)

(73) Assignees: Park Therapeutics, Inc., Monmouth Junction, NJ (US); Enteris Biopharma, Inc., Boonton, NJ (US)

( * ) Notice: Subject to any disclaimer, the term of this patent is extended or adjusted under 35 U.S.C. 154(b) by 76 days.

(21) Appl. No.: 17/675,643

(22) Filed: Feb. 18, 2022

(65) Prior Publication Data
US 2023/0000779 A1    Jan. 5, 2023

Related U.S. Application Data

(60) Division of application No. 16/267,902, filed on Feb. 5, 2019, now Pat. No. 11,285,113, which is a continuation of application No. PCT/US2017/045229, filed on Aug. 3, 2017.

(60) Provisional application No. 62/371,377, filed on Aug. 5, 2016.

(51) Int. Cl.
| | |
|---|---|
| *A61K 9/28* | (2006.01) |
| *A61K 9/20* | (2006.01) |
| *A61K 38/23* | (2006.01) |
| *A61P 19/02* | (2006.01) |
| *A61P 19/10* | (2006.01) |

(52) U.S. Cl.
CPC .......... *A61K 9/2886* (2013.01); *A61K 9/2018* (2013.01); *A61K 9/2081* (2013.01); *A61K 9/2846* (2013.01); *A61K 9/2853* (2013.01); *A61K 9/2893* (2013.01); *A61K 38/23* (2013.01); *A61P 19/02* (2018.01); *A61P 19/10* (2018.01); *A61K 9/2095* (2013.01)

(58) Field of Classification Search
None
See application file for complete search history.

(56) References Cited

U.S. PATENT DOCUMENTS

| | | | |
|---|---|---|---|
| 5,380,790 A | 1/1995 | Chen et al. | |
| 6,482,433 B1 | 11/2002 | DeRoos et al. | |
| 7,316,819 B2 | 1/2008 | Crotts et al. | |
| 8,377,863 B2 * | 2/2013 | Stern .................. | A61P 19/10 424/465 |
| 8,377,995 B2 | 2/2013 | Ikeda et al. | |
| 8,513,183 B2 | 8/2013 | Stern et al. | |
| 8,592,366 B2 | 11/2013 | Stern et al. | |
| 8,664,178 B2 | 3/2014 | Stern et al. | |
| 8,835,377 B2 | 9/2014 | Mehta et al. | |
| 9,220,704 B2 | 12/2015 | Kim et al. | |
| 9,220,758 B2 | 12/2015 | Mehta et al. | |
| 9,399,017 B2 | 7/2016 | Stern et al. | |
| 9,504,727 B2 | 11/2016 | Mehta et al. | |
| 2005/0215476 A1 | 9/2005 | Mehta et al. | |
| 2006/0105050 A1 | 5/2006 | Holm et al. | |
| 2012/0071410 A1 | 3/2012 | Mehta et al. | |
| 2016/0339081 A1 | 11/2016 | Stern et al. | |

FOREIGN PATENT DOCUMENTS

| | | |
|---|---|---|
| EP | 0517211 | 12/1992 |
| JP | H04247026 | 1/1991 |
| JP | 2004175768 A | 6/2004 |
| WO | WO1996001612 | 1/1996 |
| WO | WO1997033531 | 9/1997 |
| WO | WO2002058735 | 8/2002 |
| WO | WO2002072075 | 9/2002 |
| WO | WO2004064758 | 8/2004 |
| WO | WO2004091584 | 10/2004 |
| WO | WO2007070450 | 6/2007 |
| WO | WO2008150426 | 12/2008 |
| WO | WO2016115082 | 7/2016 |

OTHER PUBLICATIONS

Heuschmid, et al., "Polyethylene glycol-polyvinyl alcohol grafted copolymer: Study of the bioavailability after oral administration to rats," Food and Chemical Toxicology 51: S3-S6 (2013).
Stern, et al., "Oral Delivery of Peptides by Peptelligence™ Technology," Drug Development and Delivery 13(2): 36-42 (2013).

* cited by examiner

*Primary Examiner* — Celeste A Roney
(74) *Attorney, Agent, or Firm* — HALEY GUILIANO LLP; James F. Haley, Jr.; Brian M. Gummow

(57) ABSTRACT

Room-temperature stable dosage forms for oral delivery of calcitonin are disclosed herein. Dosage forms for oral delivery of calcitonin with low water content are also disclosed herein. Further disclosed herein are methods for producing such room-temperature stable dosage forms and low-water content dosage forms. Methods of treatment comprising the administration of such room-temperature stable dosage forms and low-water content dosage forms are also disclosed herein.

20 Claims, 3 Drawing Sheets

Specification includes a Sequence Listing.

SEQUENCE LISTING

```
<160> NUMBER OF SEQ ID NOS: 1

<210> SEQ ID NO 1
<211> LENGTH: 32
<212> TYPE: PRT
<213> ORGANISM: Salmo salar
<220> FEATURE:
<221> NAME/KEY: AMIDATION
<223> OTHER INFORMATION: C-term amidated

<400> SEQUENCE: 1

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30
```

ROOM TEMPERATURE STABLE ORAL CALCITONIN FORMULATION

CROSS REFERENCE TO RELATED APPLICATION

This application is a divisional application of U.S. patent application Ser. No. 16/267,902, filed on Feb. 5, 2019, which is a continuation of International Patent Application No. PCT/US2017/045229, filed on Aug. 3, 2017, which claims the benefit of U.S. Provisional Patent Application No. 62/371,377, filed Aug. 5, 2016, which are all hereby incorporated by reference herein in their respective entireties.

The Sequence Listing associated with this application is provided in text format in lieu of a paper copy and is hereby incorporated by reference into the specification. The name of the text file containing the Sequence Listing is 107371-0008-102_SL.txt. The text file is 785 bytes in size, was created on Feb. 18, 2022, and is being submitted electronically via EFS-Web.

BACKGROUND OF THE DISCLOSURE

Peptide and protein based therapeutics possess several advantageous characteristics as drugs; including having highly specific physiologic targets leading to desirable pharmacologic intervention outcomes with a low incidence of side effects. A major drawback of proteins and peptide based therapeutics is the routine need to administer these compounds via injection and the routine need for refrigeration. Peptides such as teriparatide (Forteo®) and salmon calcitonin (Miacalcin® & Fortical®) need to be refrigerated as do insulin, amylin, and GLP-related peptides.

Salmon calcitonin, for example, is a peptide hormone which decreases bone breakdown by osteoclasts and the subsequent release of calcium from bone. When used to treat bone-related diseases and calcium disorders (such as osteoporosis, Paget's disease, hypercalcemia of malignancy, and the like), it has the effect of helping maintain bone integrity and density by preventing bone breakdown. Many types of calcitonin have been isolated (e.g., human calcitonin, salmon calcitonin, eel calcitonin, porcine calcitonin, and chicken calcitonin). Notwithstanding a difference in molecular structure, salmon calcitonin may be used in humans for treatment of the calcitonin-responsive diseases discussed above. Salmon calcitonin is approximately 30-50 times more potent than human calcitonin.

Peptide pharmaceuticals are typically administered by injection or by nasal administration. Oral administration tends to be problematic because of the proteolytic degradation of the peptide by resident enzymes in the stomach and intestine. The large molecular size of peptides also prevents or significantly lowers their bioavailability. Lastly, most peptides are zwitterionic; this polar nature further reduces bioavailability. Salmon calcitonin, as an example, lacks sufficient stability in the gastrointestinal tract where it is rapidly degraded by resident digestive enzymes into inactive fragments. In addition, due to its size and polar nature, it tends to be poorly transported through intestinal walls into the blood following oral administration. For this reason, commercially available calcitonin is formulated for injection or nasal administration. Injection and nasal administration, however, are significantly less convenient than, and involve more patient discomfort than, oral administration.

U.S. Pat. No. 6,086,918 discloses a multi-component system for oral delivery of peptides which included, inter alia, significant quantities of acid useful in lowering intestinal pH and hence the activity of intestinal proteases that have neutral or basic pH optima. Preferably, the components of the system are released into the intestines as close to simultaneously as possible. Uniform dispersion of the many components of the composition can aid this objective. However, interaction of the acid excipient with the peptide active agent is preferably avoided due to acid catalyzed degradation of the peptide.

U.S. Patent Publication No. 2003/0017203 discloses a bi-layer tablet with a water-soluble coating that substantially prevents contact between a pH-lowering agent in a pharmaceutical formulation and an outer enteric coating. While such a formulation reduced the interaction of the peptide with pharmaceutical acid, consistent, reproducible, and near-simultaneous release of all components was more difficult. U.S. Pat. Nos. 8,377,863; 8,513,183; 8,592,366; 8,664,178 describe the use of malto-dextrin coated acid particles which allow the co-mingling of the peptide with the pH lowering agent in a manner which provides for the coordinated release of the peptide and pH lowering agent while at the same time preventing acid catalyzed degradation of the peptide. These patents also disclose the improvement in reproducible dissolution and bioavailability conferred by use of a water soluble sub-coat and a pH acid resistant enteric coat. Nevertheless, these tablets, although representing a significant improvement over bi-layer tablets, still required refrigeration in order to provide adequate commercially viable stability. At room temperature, these tablets would lose potency and may fail to meet regulatory requirements (90-110% label claim) for a solid dosage form. Accordingly, there remains a need for a room-temperature stable oral dosage form of salmon calcitonin.

SUMMARY OF THE DISCLOSURE

The present disclosure provides oral dosage forms, such as tablet formulations, as well as methods for making such tablet formulations. The present disclosure is based, in part, on developments that led to production of oral dosage forms, such as tablets, with minimal water content, and improved processes for attaining this minimal water content. This was particularly difficult for the formulation provided herein where the amount of active agent present (here, calcitonin) is relatively small versus the amount of excipients and the other non-active constituent components of the tablet. The present disclosure provides numerous benefits including, in certain embodiments, room temperature stability.

The present disclosure describes changes made to, e.g., the tablet core and the application of the sub-coat and enteric coat which affords room temperature stability to the present tablet formulation. A first aspect of the present disclosure provides a method for spray coating a tablet core for oral delivery of calcitonin. In some embodiments, the method minimizes the amount of water absorbed onto the tablet core during the coating process.

In some embodiments, the method for spray coating a tablet core for oral delivery of calcitonin comprising: (a) providing a tablet core; (b) applying a water-soluble barrier layer in an initial spray at a first spray rate sufficient to add approximately 0.25% (w/w) to the tablet core in about 30 minutes at an average product temperature (i.e., bed temperature) of at least 45° C.; and (c) applying an enteric coating. Optionally, the tablet core comprises (i) calcitonin intermixed with coated citric acid particles, (ii) crospovidone; (iii) copovidone; (iv) microcrystalline cellulose; and (v) magnesium stearate. In some embodiments, the microcrystalline cellulose is silicified microcrystalline cellulose.

A second aspect of the present disclosure provides a method of preparing a tablet for oral delivery of calcitonin comprising (a) dry blending calcitonin, silicified microcrystalline cellulose, coated citric acid, copovidone, crospovidone, and magnesium stearate; (b) compressing the blended mixture into a tablet core; (c) applying a water-soluble barrier layer in an initial spray at a first spray rate sufficient to add approximately 0.25% (w/w) to the tablet core in about 30 minutes at an average product temperature of at least 45° C.; and (d) applying an enteric coating. In some embodiments, the microcrystalline cellulose is silicified microcrystalline cellulose.

In some embodiments of any of the above methods, the calcitonin is salmon calcitonin. The tablet may comprise about 100 to about 1,000 μg salmon calcitonin, about 100 to about 500 μg salmon calcitonin, preferably about 200 μg salmon calcitonin. Optionally, the coated citric acid particles are maltodextrin-coated citric acid particles. In some embodiments of any of the above methods, the tablet core comprises (i) about 0.01% (w/w) to about 0.10% (w/w) salmon calcitonin; (ii) about 62% (w/w) maltodextrin-coated citric acid; (iii) about 1.1% (w/w) crospovidone; (iv) about 5% (w/w) copovidone; (v) about 31% (w/w) silicified microcrystalline cellulose; and (vi) about 0.5% (w/w) magnesium stearate. In some embodiments, the tablet core comprises about 0.02% (w/w) salmon calcitonin.

In some embodiments of any of the above methods, the water-soluble barrier layer comprises a polyvinyl alcohol-polyethylene glycol graft copolymer. Optionally, the enteric coating comprises a methacrylic acid-ethyl acrylate copolymer (1:1).

In some embodiments of any of the above methods, the first spray rate is sufficient to add approximately 0.5% (w/w) to the tablet core in about 30 minutes. Optionally, the first spray rate is such that no more than 0.5% (w/w) is added to the tablet core in about 30 minutes.

In some embodiments of any of the above methods, after applying the water-soluble barrier layer at the first spray rate for at least 30 minutes, the water-soluble barrier layer is applied in a subsequent spray at a second spray rate, which is faster than the first spray rate. In some embodiments, the second spray rate is sufficient to add about 5.5% (w/w) to the tablet core in about four and a half hours. Optionally, the second spray rate is sufficient to add about 5.5% (w/w) to the tablet core in about four hours. The second spray rate may be sufficient to add about 5.5% (w/w) to the tablet core in about three and a half hours. In some embodiments, the second spray rate is sufficient to add about 5.5% (w/w) to the tablet core in about three hours. Optionally, the second spray rate is sufficient to add about 5.5% (w/w) to the tablet core in about two and a half hours. In some embodiments, the second spray rate is sufficient to add about 5.5% (w/w) to the tablet core in about two hours.

In some embodiments of any of the above methods, the method comprises applying the water-soluble barrier layer at the first spray rate until about 0.5% (w/w) is added to the tablet core and then applying the water-soluble barrier layer at the second spray rate. Optionally, the method comprises applying the water-soluble barrier layer at the first spray rate until about 0.6% (w/w) is added to the tablet core and then applying the water-soluble barrier layer at the second spray rate. In some embodiments, the method comprises applying the water-soluble barrier layer at the first spray rate until about 0.7% (w/w) is added to the tablet core and then applying the water-soluble barrier layer at the second spray rate. The method may comprise applying the water-soluble barrier layer at the first spray rate until about 0.8% (w/w) is added to the tablet core and then applying the water-soluble barrier layer at the second spray rate. Optionally, the method comprises applying the water-soluble barrier layer at the first spray rate until about 0.9% (w/w) is added to the tablet core and then applying the water-soluble barrier layer at the second spray rate. In some embodiments, the method comprises applying the water-soluble barrier layer at the first spray rate until about 1.0% (w/w) is added to the tablet core and then applying the water-soluble barrier layer at the second spray rate. Optionally, the method comprises applying the water-soluble barrier layer at the first spray rate until about 1.25% (w/w) is added to the tablet core and then applying the water-soluble barrier layer at the second spray rate. In some embodiments, the method comprises applying the water-soluble barrier layer at the first spray rate until about 1.5% (w/w) is added to the tablet core and then applying the water-soluble barrier layer at the second spray rate. Optionally, the method comprises applying the water-soluble barrier layer at the first spray rate until about 1.75% (w/w) is added to the tablet core and then applying the water-soluble barrier layer at the second spray rate. In some embodiments, the method comprises applying the water-soluble barrier layer at the first spray rate until about 2.0% (w/w) is added to the tablet core and then applying the water-soluble barrier layer at the second spray rate.

In some embodiments of any of the above methods, the water-soluble barrier layer is applied at the second spray rate until a total of about 3.0% (w/w) is added to the tablet core. Optionally, the water-soluble barrier layer is applied at the second spray rate until a total of about 4.0% (w/w) is added to the tablet core. The water-soluble barrier layer may be applied at the second spray rate until a total of about 5.0% (w/w) is added to the tablet core. In some embodiments, the water-soluble barrier layer is applied at the second spray rate until a total of about 6.0% (w/w) is added to the tablet core. Optionally, the water-soluble barrier layer is applied at the second spray rate until a total of about 7.0% (w/w) is added to the tablet core.

In some embodiments of any of the above methods, the average product temperature (i.e., bed temperature) during the initial spray is 50° C.±5° C. In some embodiments, the average product temperature during the initial spray is at least 46° C. Optionally, the average product temperature during the initial spray is at least 47° C. The average product temperature during the initial spray may be at least 48° C. In some embodiments, the average product temperature during the initial spray is at least 49° C. Optionally, the average product temperature during the initial spray is at least 50° C.

In some embodiments of any of the above methods, the minimum product temperature during the initial spray is at least 45° C.

In some embodiments of any of the above methods, the enteric coating adds about 6% to the weight of the tablet, including the tablet core and the water-soluble barrier layer. Optionally, the enteric coating adds about 7% to the weight of the tablet, including the tablet core and the water-soluble barrier layer. In some embodiments, the enteric coating adds about 8% to the weight of the tablet, including the tablet core and the water-soluble barrier layer.

A third aspect of the present disclosure provides a pharmaceutical solid dosage form for oral delivery of calcitonin comprising: (a) a calcitonin intermixed with coated acid particles, wherein the coated acid particles are coated with a pharmaceutically acceptable protective coating, wherein the protective coating separates the acid from the calcitonin in the composition; (b) an enteric coating; and (c) a water-soluble barrier layer that separates the coated acid particles from the enteric coating, wherein the tablet contains no more than 2.5% (w/w) water. The solid dosage form may be a capsule or a tablet. In some embodiments, the capsule is a powder-filled capsule. In some embodiments, the capsule is used for over-encapsulation of a tablet core. When the solid dosage form is a capsule, the barrier layer can be the capsule body and cap. In some embodiments, the capsule body and cap are coated with an enteric coating. Optionally, the capsule body and cap comprise one or more pharmaceutically approved enteric polymers.

When the solid dosage form is a tablet, the calcitonin intermixed with coated acid particles are present in the tablet core and the tablet core is coated with the water-soluble barrier layer and the enteric coating. The water-soluble barrier layer may be prepared and applied using a non-aqueous solvent, such as isopropyl alcohol or methylene chloride.

In some embodiments, the solid dosage form, such as a tablet, contains no more than 2.25% (w/w) water. The solid dosage form may contain no more than 2.0% (w/w) water. In some embodiments, the solid dosage form, such as a tablet, contains no more than 1.9% (w/w) water. Optionally, the solid dosage form, such as a tablet, contains no more than 1.8% (w/w) water. The solid dosage form, such as a tablet, may contain no more than 1.7% (w/w) water. In some embodiments, the solid dosage form, such as a table, contains no more than 1.6% (w/w) water. Optionally, the solid dosage form, such as a tablet, contains no more than 1.5% (w/w) water.

In some embodiments, the total acid in the pharmaceutical solid dosage form is in a quantity which, if added to ten milliliters of 0.1 M aqueous sodium bicarbonate solution, would be sufficient to lower the pH of said solution to no higher than 5.5. Optionally, the solid dosage form does not include an amount of base which, if released together with the acid, would prevent the pH of said solution from dropping to 5.5 or below. The acid may be selected from citric acid, tartaric acid and an acid salt of an amino acid. Optionally, the acid is citric acid. In some embodiments, the protective coating of the coated acid particles is a sugar. Optionally, the sugar is glucose. The sugar may be maltodextrin. In certain embodiments, the solid dosage form is a tablet.

In some embodiments, the water-soluble barrier layer comprises a polyvinyl alcohol-polyethylene glycol graft copolymer. Optionally, the water-soluble barrier layer adds 3-6% to the weight of the pharmaceutical tablet, exclusive of the enteric coating.

In some embodiments, the enteric coating comprises a methacrylic acid-ethyl acrylate copolymer (1:1). Optionally, the enteric coating adds 6-8% to the weight of the tablet, including the tablet core and the water-soluble barrier layer.

In some embodiments, the calcitonin is selected from the group consisting of human calcitonin, salmon calcitonin, eel calcitonin, elkatonin, porcine calcitonin, and chicken calcitonin. Optionally, the calcitonin is salmon calcitonin. The solid dosage form, such as a tablet, may comprise about 100 to about 1,000 µg salmon calcitonin, about 100 to about 500 µg salmon calcitonin, preferably about 200 µg salmon calcitonin.

A fourth aspect of the present disclosure provides a pharmaceutical tablet for oral delivery of calcitonin comprising: (a) a tablet core comprising (i) salmon calcitonin intermixed with maltodextrin-coated citric acid particles, wherein the coated acid particles are coated with a pharmaceutically acceptable protective coating, wherein the protective coating separates the acid from the salmon calcitonin in the composition; (ii) crospovidone; (iii) copovidone; (iv) microcrystalline cellulose; and (v) magnesium stearate; (b) an enteric coating, wherein the enteric coating comprises a methacrylic acid-ethyl acrylate copolymer (1:1); and (c) a water-soluble barrier layer that separates the coated acid particles from the enteric coating, wherein the water-soluble barrier layer comprises a polyvinyl alcohol-polyethylene glycol graft copolymer; wherein the tablet contains no more than 2.5% (w/w) water. In some embodiments, the microcrystalline cellulose is silicified microcrystalline cellulose.

In some embodiments, the tablet comprises about 100 to about 1000 µg salmon calcitonin, preferably about 200 µg salmon calcitonin. Optionally, the tablet core comprises (i) about 0.01% (w/w) to about 0.10% (w/w) salmon calcitonin; (ii) about 62% (w/w) maltodextrin-coated citric acid; (iii) about 1.1% (w/w) crospovidone; (iv) about 5% (w/w) copovidone; (v) about 31% (w/w) silicified microcrystalline cellulose; and (vi) about 0.5% (w/w) magnesium stearate. In some embodiments, the tablet core comprises 0.02% (w/w) salmon calcitonin.

In some embodiments, the water-soluble barrier layer adds about 6% to the weight of the tablet core, exclusive of the enteric coating. Optionally, the enteric coating adds about 7% to the weight of the tablet, including the tablet core and the water-soluble barrier layer.

A fifth aspect of the present disclosure provides a pharmaceutical solid dosage form for oral delivery of calcitonin comprising: (a) a calcitonin intermixed with coated acid particles, wherein the coated acid particles are coated with a pharmaceutically acceptable protective coating, wherein the protective coating separates the acid from the calcitonin in the composition; (b) an enteric coating; and (c) a water-soluble barrier layer that separates the coated acid particles from the enteric coating, wherein the solid dosage form contains no more than 2.5% (w/w) water; and wherein the solid dosage form is stable at room temperature. The solid dosage form may be a capsule or a tablet. In some embodiments, the capsule is a powder-filled capsule. In some embodiments, the capsule is used for over-encapsulation of a tablet core. When the solid dosage form is a capsule, the barrier layer is the capsule body and cap. In some embodiments, the capsule body and cap are coated with an enteric coating. Optionally, the capsule body and cap comprise one or more pharmaceutically approved enteric polymers.

When the solid dosage form is a tablet, the calcitonin intermixed with coated acid particles are present in the tablet core and the tablet core is coated with the water-soluble barrier layer and the enteric coating. The water-soluble barrier layer may be prepared and applied using a non-aqueous solvent, such as isopropyl alcohol or methylene chloride.

In some embodiments of any of the foregoing or following, the solid dosage form contains no more than 2.25% (w/w) water. The solid dosage form may contain no more than 2.0% (w/w) water. In some embodiments, the solid dosage form contains no more than 1.9% (w/w) water. Optionally, the solid dosage form contains no more than 1.8% (w/w) water. The solid dosage form may contain no more than 1.7% (w/w) water. In some embodiments, the solid dosage form contains no more than 1.6% (w/w) water. Optionally, the solid dosage form contains no more than 1.5% (w/w) water. In certain embodiments, the solid dosage form is a tablet.

In some embodiments of any of the foregoing or following, the total acid in the pharmaceutical solid dosage form is in a quantity which, if added to ten milliliters of 0.1 M aqueous sodium bicarbonate solution, would be sufficient to lower the pH of said solution to no higher than 5.5. Optionally, the solid dosage form does not include an amount of base which, if released together with the acid, would prevent the pH of said solution from dropping to 5.5 or below. The acid may be selected from citric acid, tartaric acid and an acid salt of an amino acid. Optionally, the acid is citric acid. In some embodiments, the protective coating of the coated acid particles is a sugar. Optionally, the sugar is glucose. The sugar may be maltodextrin.

In some embodiments of any of the foregoing or following, the water-soluble barrier layer comprises a polyvinyl alcohol-polyethylene glycol graft copolymer. Optionally, the water-soluble barrier layer adds 3-6% to the weight of the pharmaceutical tablet, exclusive of the enteric coating.

In some embodiments of any of the foregoing or following, the enteric coating comprises a methacrylic acid-ethyl acrylate copolymer (1:1). Optionally, the enteric coating adds 6-8% to the weight of the tablet, including the tablet core and the water-soluble barrier layer.

In some embodiments, the calcitonin is selected from the group consisting of human calcitonin, salmon calcitonin, eel calcitonin, elkatonin, porcine calcitonin, and chicken calcitonin. Optionally, the calcitonin is salmon calcitonin. The solid dosage form may comprise about 100 to about 1000 µg salmon calcitonin, such as about 200 µg salmon calcitonin. In certain embodiments, the solid dosage form is a tablet.

A sixth aspect of the present disclosure provides a pharmaceutical tablet for oral delivery of calcitonin comprising: (a) a tablet core comprising (i) salmon calcitonin intermixed with maltodextrin-coated citric acid particles, wherein the coated acid particles are coated with a pharmaceutically acceptable protective coating, wherein the protective coating separates the acid from the salmon calcitonin in the composition; (ii) crospovidone; (iii) copovidone; (iv) microcrystalline cellulose; and (v) magnesium stearate; (b) an enteric coating, wherein the enteric coating comprises a methacrylic acid-ethyl acrylate copolymer (1:1); and (c) a water-soluble barrier layer that separates the coated acid particles from the enteric coating, wherein the water-soluble barrier layer comprises a polyvinyl alcohol-polyethylene glycol graft copolymer; wherein the tablet contains no more than 2.5% (w/w) water; and wherein the tablet is stable at room temperature. In some embodiments, the microcrystalline cellulose is silicified microcrystalline cellulose.

In some embodiments, the tablet comprises about 200 µg salmon calcitonin. Optionally, the tablet core comprises (i) about 0.01% (w/w) to about 0.10% (w/w) salmon calcitonin; (ii) about 62% (w/w) maltodextrin-coated citric acid; (iii) about 1.1% (w/w) crospovidone; (iv) about 5% (w/w) copovidone; (v) about 31% (w/w) silicified microcrystalline cellulose; and (vi) about 0.5% (w/w) magnesium stearate. In some embodiments, the tablet core comprises about 0.02% (w/w) salmon calcitonin.

In some embodiments, the water-soluble barrier layer adds about 6% to the weight of the tablet core, exclusive of the enteric coating. Optionally, the enteric coating adds about 7% to the weight of the tablet, including the tablet core and the water-soluble barrier layer.

Any of the pharmaceutical tablets for oral delivery of calcitonin may be produced by any of the methods disclosed above.

A seventh aspect of the present disclosure provides a method for treating a bone-related disease, a calcium disorder, an inflammatory disease or a degenerative disease by administering any of the above pharmaceutical solid dosage form or any solid dosage form of the disclosure described herein to a subject in need thereof. Optionally, the subject is a human patient. The subject may be a dog or a horse, or another companion animal.

In some embodiments, the bone-related disease is selected from the group consisting of osteoporosis, Paget's disease, pain associated with recent vertebral fragility fractures, and hypercalcemia of malignancy. In some embodiments, the inflammatory disease is selected from the group consisting of osteoarthritis (OA), rheumatoid arthritis (RA), juvenile rheumatoid arthritis (JRA), and ankylosing spondylitis (AS).

Particular embodiments of the disclosure are set forth in the following numbered paragraphs:

1. A pharmaceutical solid dosage form for oral delivery of calcitonin comprising:
   (a) a calcitonin intermixed with coated acid particles, wherein the coated acid particles are coated with a pharmaceutically acceptable protective coating, wherein the protective coating separates the acid from the calcitonin in the composition;
   (b) an enteric coating; and
   (c) a water-soluble barrier layer that separates the coated acid particles from the enteric coating,
wherein the solid dosage form contains no more than 2.5% (w/w) water.

2. The pharmaceutical solid dosage form according to paragraph 1, wherein the solid dosage form is a capsule or a tablet.

3. The pharmaceutical solid dosage form according to paragraph 2, wherein the capsule is a powder-filled capsule.

4. The pharmaceutical solid dosage form according to paragraph 2, wherein the capsule is used for over-encapsulation of a tablet core.

5. The pharmaceutical solid dosage form according to any one of paragraphs 2-4, wherein the barrier layer is the capsule body and cap.

6. The pharmaceutical solid dosage form according to paragraph 5, wherein the capsule body and cap are coated with an enteric coating.

7. The pharmaceutical solid dosage form according to paragraph 5, wherein the capsule body and cap comprise one or more enteric polymers, such as a pharmaceutically approved enteric polymer.

8. The pharmaceutical solid dosage form according to paragraph 2, wherein the solid dosage form is a tablet, wherein the calcitonin intermixed with coated acid particles are present in the tablet core, and wherein the tablet core is coated with the water-soluble barrier layer and the enteric coating.

9. The pharmaceutical solid dosage form according to any one of paragraphs 1-8, wherein the solid dosage form contains no more than 2.25% (w/w) water.

10. The pharmaceutical solid dosage form according to any one of paragraphs 1-8, wherein the solid dosage form contains no more than 2.0% (w/w) water.

11. The pharmaceutical solid dosage form according to any one of paragraphs 1-8, wherein the solid dosage form contains no more than 1.9% (w/w) water.

12. The pharmaceutical solid dosage form according to any one of paragraphs 1-8, wherein the solid dosage form contains no more than 1.8% (w/w) water.

13. The pharmaceutical solid dosage form according to any one of paragraphs 1-8, wherein the solid dosage form contains no more than 1.7% (w/w) water.

14. The pharmaceutical solid dosage form according to any one of paragraphs 1-8, wherein the solid dosage form contains no more than 1.6% (w/w) water.

15. The pharmaceutical solid dosage form according to any one of paragraphs 1-8, wherein the solid dosage form contains no more than 1.5% (w/w) water.

16. The pharmaceutical solid dosage form according to any one of paragraphs 1-15, wherein total acid in said pharmaceutical solid dosage form is in a quantity which, if added to ten milliliters of 0.1 M aqueous sodium bicarbonate solution, would be sufficient to lower the pH of said solution to no higher than 5.5.

17. The pharmaceutical solid dosage form according to any one of paragraphs 1-16, wherein the solid dosage form does not include an amount of base which, if released together with the acid, would prevent the pH of said solution from dropping to 5.5 or below.

18. The pharmaceutical solid dosage form of any one of paragraphs 1-17, wherein the acid is selected from citric acid, tartaric acid and an acid salt of an amino acid.

19. The pharmaceutical solid dosage form of paragraph 18, wherein the acid is citric acid.

20. The pharmaceutical solid dosage form of any one of paragraphs 1-19, wherein the protective coating of the coated acid particles is a sugar.

21. The pharmaceutical solid dosage form of paragraph 20, wherein the sugar is glucose.

22. The pharmaceutical solid dosage form of paragraph 20, wherein the sugar is maltodextrin.

23. The pharmaceutical solid dosage form of any one of paragraphs 1, 2 and 8-22, wherein the solid dosage form is a tablet, and wherein the barrier layer is a water-soluble barrier layer.

24. The pharmaceutical solid dosage form of any one of paragraphs 1, 2 and 8-23, wherein the solid dosage form is a tablet, and wherein the water-soluble barrier layer is prepared and applied using a non-aqueous solvent.

25. The pharmaceutical solid dosage form of paragraph 23 or 24, wherein the water-soluble barrier layer comprises a polyvinyl alcohol-polyethylene glycol graft copolymer.

26. The pharmaceutical solid dosage form of any one of paragraphs 23-25, wherein the solid dosage form is a tablet, and wherein the water-soluble barrier layer adds 3-6% to the weight of the pharmaceutical tablet, exclusive of the enteric coating.

27. The pharmaceutical solid dosage form of any one of paragraphs 1-26, wherein the enteric coating comprises a methacrylic acid-ethyl acrylate copolymer (1:1).

28. The pharmaceutical solid dosage form of any one of paragraphs 1, 2 and 8-27, wherein the solid dosage form is a tablet, and wherein the enteric coating adds 6-8% to the weight of the tablet, including the tablet core and the water-soluble barrier layer.

29. The pharmaceutical solid dosage form of any one of paragraphs 1-28, wherein the calcitonin is selected from the group consisting of human calcitonin, salmon calcitonin, eel calcitonin, elkatonin, porcine calcitonin, and chicken calcitonin.

30. The pharmaceutical solid dosage form of paragraph 29, wherein the calcitonin is salmon calcitonin.

31. The pharmaceutical solid dosage form of paragraph 30, wherein the solid dosage form comprises about 100 to about 1000 μg salmon calcitonin.

32. The pharmaceutical solid dosage form of paragraph 31, wherein the solid dosage form comprises about 200 μg salmon calcitonin.

33. The pharmaceutical solid dosage form of any one of paragraphs 1-32, wherein the solid dosage form further comprises an absorption enhancer.

34. The pharmaceutical solid dosage form of paragraph 33, wherein the absorption enhancer is L-lauroyl carnitine.

35. A pharmaceutical tablet for oral delivery of calcitonin comprising:
  (a) a tablet core comprising
    a. salmon calcitonin intermixed with maltodextrin-coated citric acid particles, wherein the coated acid particles are coated with a pharmaceutically acceptable protective coating, wherein the protective coating separates the acid from the salmon calcitonin in the composition;
    b. crospovidone;
    c. copovidone;
    d. microcrystalline cellulose; and
    e. magnesium stearate;
  (b) an enteric coating, wherein the enteric coating comprises a methacrylic acid-ethyl acrylate copolymer (1:1); and
  (c) a water-soluble barrier layer that separates the coated acid particles from the enteric coating, wherein the water-soluble barrier layer comprises a polyvinyl alcohol-polyethylene glycol graft copolymer; wherein the tablet contains no more than 2.5% (w/w) water.

36. The pharmaceutical tablet of paragraph 35, wherein the tablet comprises about 100 μg to about 1,000 μg salmon calcitonin.

37. The pharmaceutical tablet of paragraph 35 or 36, wherein the tablet core comprises
  (a) about 0.01% (w/w) to about 0.10% (w/w) salmon calcitonin;
  (b) about 62% (w/w) maltodextrin-coated citric acid;
  (c) about 1.1% (w/w) crospovidone;
  (d) about 5% (w/w) copovidone;
  (e) about 31% (w/w) silicified microcrystalline cellulose; and
  (f) about 0.5% (w/w) magnesium stearate.

38. The pharmaceutical tablet of any one of paragraphs 35-37, wherein the tablet comprises about 200 μg salmon calcitonin.

39. The pharmaceutical tablet of any one of paragraphs 35-38, wherein the tablet core comprises about 0.02% (w/w) salmon calcitonin.

40. The pharmaceutical tablet of any one of paragraphs 35-39, wherein the water-soluble barrier layer adds about 6% to the weight of the tablet core, exclusive of the enteric coating.

41. The pharmaceutical tablet of any one of paragraphs 35-40, wherein the enteric coating adds about 7% to the weight of the tablet, including the tablet core and the water-soluble barrier layer.

42. A pharmaceutical solid dosage form for oral delivery of calcitonin comprising:
  (a) a calcitonin intermixed with coated acid particles, wherein the coated acid particles are coated with a pharmaceutically acceptable protective coating, wherein the protective coating separates the acid from the calcitonin in the composition;
  (b) an enteric coating; and
  (c) a water-soluble barrier layer that separates the coated acid particles from the enteric coating, wherein the solid dosage form contains no more than 2.5% (w/w) water; and wherein the solid dosage form is stable at room temperature.

43. The pharmaceutical solid dosage form according to paragraph 42, wherein the solid dosage form is a capsule or a tablet.

44. The pharmaceutical solid dosage form according to paragraph 43, wherein the capsule is a powder-filled capsule.

45. The pharmaceutical solid dosage form according to paragraph 43, wherein the capsule is sued for over-encapsulation of a tablet core.

46. The pharmaceutical solid dosage form according to any one of paragraphs 43-45, wherein the barrier layer is the capsule body and cap.

47. The pharmaceutical solid dosage form according to paragraph 46, wherein the capsule body and cap are coated with an enteric coating.

48. The pharmaceutical solid dosage form according to paragraph 46, wherein the capsule body and cap comprise one or more pharmaceutically approved enteric polymers.

49. The pharmaceutical solid dosage form according to paragraph 43, wherein the solid dosage form is a tablet, wherein the calcitonin intermixed with coated acid particles are present in the tablet core, and wherein the tablet core is coated with the water-soluble barrier layer and the enteric coating.

50. The pharmaceutical solid dosage form according to any one of paragraphs 42-49, wherein the solid dosage form contains no more than 2.25% (w/w) water.

51. The pharmaceutical solid dosage form according to any one of paragraphs 42-49, wherein the solid dosage form contains no more than 2.0% (w/w) water.

52. The pharmaceutical solid dosage form according to any one of paragraphs 42-49, wherein the tablet contains no more than 1.9% (w/w) water.

53. The pharmaceutical solid dosage form according to any one of paragraphs 42-49, wherein the solid dosage form contains no more than 1.8% (w/w) water.

54. The pharmaceutical solid dosage form according to any one of paragraphs 42-49, wherein the solid dosage form contains no more than 1.7% (w/w) water.

55. The pharmaceutical solid dosage form according to any one of paragraphs 42-49, wherein the solid dosage form contains no more than 1.6% (w/w) water.

56. The pharmaceutical solid dosage form according to any one of paragraphs 42-49, wherein the solid dosage form contains no more than 1.5% (w/w) water.

57. The pharmaceutical solid dosage form according to any one of paragraphs 42-56, wherein total acid in said pharmaceutical composition is in a quantity which, if added to ten milliliters of 0.1 M aqueous sodium bicarbonate solution, would be sufficient to lower the pH of said solution to no higher than 5.5.

58. The pharmaceutical solid dosage form according to any one of paragraphs 42-57, wherein the composition does not include an amount of base which, if released together with the acid, would prevent the pH of said solution from dropping to 5.5 or below.

59. The pharmaceutical solid dosage form of any one of paragraphs 42-58, wherein the acid is selected from citric acid, tartaric acid and an acid salt of an amino acid.

60. The pharmaceutical solid dosage form of paragraph 59, wherein the acid is citric acid.

61. The pharmaceutical solid dosage form of any one of paragraphs 42-60, wherein the protective coating of the coated acid particles is a sugar.

62. The pharmaceutical solid dosage form of paragraph 61, wherein the sugar is glucose.

63. The pharmaceutical solid dosage form of paragraph 61, wherein the sugar is maltodextrin.

64. The pharmaceutical solid dosage form of any one of paragraphs 42, 43, and 49-63, wherein the solid dosage form is a tablet, and wherein the barrier layer is a water-soluble barrier layer.

65. The pharmaceutical solid dosage form of paragraph 64, wherein the water-soluble barrier layer is prepared and applied using a non-aqueous solvent, such as isopropyl alcohol or methylene chloride.

66. The pharmaceutical solid dosage form of paragraph 64 or 65, wherein the water-soluble barrier layer comprises a polyvinyl alcohol-polyethylene glycol graft copolymer.

67. The pharmaceutical solid dosage form of any one of paragraphs 64-66, wherein the water-soluble barrier layer adds 3-6% to the weight of the pharmaceutical composition, exclusive of the enteric coating.

68. The pharmaceutical solid dosage form of any one of paragraphs 42-67, wherein the enteric coating comprises a methacrylic acid-ethyl acrylate copolymer (1:1).

69. The pharmaceutical solid dosage form of any one of paragraphs 42, 43, and 49-68, wherein the solid dosage form is a tablet, and wherein the enteric coating adds 6-8% to the weight of the tablet, including the tablet core and the water-soluble barrier layer.

70. The pharmaceutical solid dosage form of any one of paragraphs 42-69, wherein the calcitonin is selected from the group consisting of human calcitonin, salmon calcitonin, eel calcitonin, elkatonin, porcine calcitonin, and chicken calcitonin.

71. The pharmaceutical solid dosage form of paragraph 70, wherein the calcitonin is salmon calcitonin.

72. The pharmaceutical solid dosage form of paragraph 71, wherein the solid dosage form comprises about 100 to about 1,000 µg salmon calcitonin.

73. The pharmaceutical solid dosage form of paragraph 72, wherein the solid dosage form comprises about 200 µg salmon calcitonin.

74. The pharmaceutical solid dosage form of any one of paragraphs 42-73, wherein the solid dosage form further comprises an absorption enhancer.

75. The pharmaceutical solid dosage form of paragraph 74, wherein the absorption enhancer is L-lauroyl carnitine.

76. A pharmaceutical tablet for oral delivery of calcitonin comprising:
  (a) a tablet core comprising
    a. salmon calcitonin intermixed with maltodextrin-coated citric acid particles, wherein the coated acid particles are coated with a pharmaceutically acceptable protective coating, wherein the protective coating separates the acid from the salmon calcitonin in the composition;
    b. crospovidone;
    c. copovidone;
    d. microcrystalline cellulose; and
    e. magnesium stearate;
  (b) an enteric coating, wherein the enteric coating comprises a methacrylic acid-ethyl acrylate copolymer (1:1); and
  (c) a water-soluble barrier layer that separates the coated acid particles from the enteric coating, wherein the water-soluble barrier layer comprises a polyvinyl alcohol-polyethylene glycol graft copolymer;
wherein the tablet contains no more than 2.5% (w/w) water; and
wherein the tablet is stable at room temperature.

77. The pharmaceutical tablet of paragraph 76, wherein the microcrystalline cellulose is silicified microcrystalline cellulose.

78. The pharmaceutical tablet of paragraph 76 or 77, wherein the tablet comprises about 200 µg salmon calcitonin.
79. The pharmaceutical tablet of paragraph 77 or 78, wherein the tablet core comprises
    (a) about 0.01% (w/w) to about 0.10% (w/w) salmon calcitonin;
    (b) about 62% (w/w) maltodextrin-coated citric acid;
    (c) about 1.1% (w/w) crospovidone;
    (d) about 5% (w/w) copovidone;
    (e) about 31% (w/w) silicified microcrystalline cellulose; and
    (f) about 0.5% (w/w) magnesium stearate.
80. The pharmaceutical tablet of paragraph 79, wherein the tablet core comprises about 0.02% (w/w) salmon calcitonin.
81. The pharmaceutical tablet of any one of paragraphs 76-80, wherein the water-soluble barrier layer adds about 6% to the weight of the tablet core, exclusive of the enteric coating.
82. The pharmaceutical tablet of any one of paragraphs 76-81, wherein the enteric coating adds about 7% to the weight of the tablet, including the tablet core and the water-soluble barrier layer.
83. A method for preparing a tablet for oral delivery of calcitonin comprising:
    (a) dry blending calcitonin, silicified microcrystalline cellulose, coated citric acid, copovidone, crospovidone, and magnesium stearate;
    (b) compressing the blended mixture into a tablet core;
    (c) applying a water-soluble barrier layer in an initial spray at a first spray rate sufficient to add approximately 0.25% (w/w) to the tablet core in about 30 minutes at an average product temperature of at least 45° C.; and
    (d) applying an enteric coating.
84. A method for spray coating a tablet core for oral delivery of calcitonin comprising:
    (a) providing a tablet core;
    (b) applying a water-soluble barrier layer in an initial spray at a first spray rate sufficient to add approximately 0.25% (w/w) of the water-soluble barrier layer to the tablet core in about 30 minutes at an average product temperature of at least 45° C.; and
    (c) applying an enteric coating.
85. The method of paragraph 84, wherein the tablet core comprises
    (a) calcitonin intermixed with coated citric acid particles,
    (b) crospovidone;
    (c) copovidone;
    (d) microcrystalline cellulose; and
    (e) magnesium stearate.
86. The method of paragraph 85, wherein the microcrystalline cellulose is silicified microcrystalline cellulose.
87. The method of any one of paragraphs 83-86, wherein the calcitonin is salmon calcitonin.
88. The method of paragraph 87, wherein the tablet comprises about 100 to about 1000 µg salmon calcitonin.
89. The method of paragraph 88, wherein the tablet comprises about 200 µg salmon calcitonin.
90. The method of any one of paragraphs 83-89, wherein the coated citric acid particles are maltodextrin-coated citric acid particles.
91. The method of any one of paragraphs 83 and 86-90, wherein the tablet core comprises
    (a) about 0.01% (w/w) to about 0.10% (w/w) salmon calcitonin;
    (b) about 62% (w/w) maltodextrin-coated citric acid;
    (c) about 1.1% (w/w) crospovidone;
    (d) about 5% (w/w) copovidone;
    (e) about 31% (w/w) silicified microcrystalline cellulose; and
    (f) about 0.5% (w/w) magnesium stearate.
92. The method of paragraph 91, wherein the tablet core comprises about 0.02% (w/w) salmon calcitonin.
93. The method of any one of paragraphs 83-92, wherein the tablet core further comprises an absorption enhancer.
94. The method of paragraph 93, wherein the absorption enhancer is L-lauroyl carnitine.
95. The method of any one of paragraphs 83-94, wherein the water-soluble barrier layer comprises a polyvinyl alcohol-polyethylene glycol graft copolymer.
96. The method of any one of paragraphs 83-95, wherein the enteric coating comprises a methacrylic acid-ethyl acrylate copolymer (1:1).
97. The method of any one of paragraphs 83-96, wherein the first spray rate is sufficient to add approximately 0.5% (w/w) of the water-soluble barrier layer to the tablet core in about 30 minutes.
98. The method of any one of paragraphs 83-97, wherein the first spray rate is such that no more than 0.5% (w/w) of the water-soluble barrier layer is added to the tablet core in about 30 minutes.
99. The method of any one of paragraphs 83-98, wherein after applying the water-soluble barrier layer at the first spray rate for at least 30 minutes, the water-soluble barrier layer is applied in a subsequent spray at a second spray rate, which is faster than the first spray rate.
100. The method of paragraph 99, wherein the second spray rate is sufficient to add about 5.5% (w/w) of the water-soluble barrier layer to the tablet core in about four and a half hours.
101. The method of paragraph 99, wherein the second spray rate is sufficient to add about 5.5% (w/w) of the water-soluble barrier layer to the tablet core in about four hours.
102. The method of paragraph 99, wherein the second spray rate is sufficient to add about 5.5% (w/w) of the water-soluble barrier layer to the tablet core in about three and a half hours.
103. The method of paragraph 99, wherein the second spray rate is sufficient to add about 5.5% (w/w) of the water-soluble barrier layer to the tablet core in about three hours.
104. The method of paragraph 99, wherein the second spray rate is sufficient to add about 5.5% (w/w) of the water-soluble barrier layer to the tablet core in about two and a half hours.
105. The method of paragraph 99, wherein the second spray rate is sufficient to add about 5.5% (w/w) of the water-soluble barrier layer to the tablet core in about two hours.
106. The method of any one of paragraphs 99-105, wherein the method comprises applying the water-soluble barrier layer at the first spray rate until about 0.5% (w/w) of the water-soluble barrier layer is added to the tablet core and then applying the water-soluble barrier layer at the second spray rate.
107. The method of any one of paragraphs 99-105, wherein the method comprises applying the water-soluble barrier layer at the first spray rate until about 0.6% (w/w) of the water-soluble barrier layer is added to the tablet core and then applying the water-soluble barrier layer at the second spray rate.
108. The method of any one of paragraphs 99-105, wherein the method comprises applying the water-soluble barrier layer at the first spray rate until about 0.7% (w/w) of the water-soluble barrier layer is added to the tablet core and then applying the water-soluble barrier layer at the second spray rate.

109. The method of any one of paragraphs 99-105, wherein the method comprises applying the water-soluble barrier layer at the first spray rate until about 0.8% (w/w) of the water-soluble barrier layer is added to the tablet core and then applying the water-soluble barrier layer at the second spray rate.

110. The method of any one of paragraphs 99-105, wherein the method comprises applying the water-soluble barrier layer at the first spray rate until about 0.9% (w/w) of the water-soluble barrier layer is added to the tablet core and then applying the water-soluble barrier layer at the second spray rate.

111. The method of any one of paragraphs 99-105, wherein the method comprises applying the water-soluble barrier layer at the first spray rate until about 1.0% (w/w) of the water-soluble barrier layer is added to the tablet core and then applying the water-soluble barrier layer at the second spray rate.

112. The method of any one of paragraphs 99-105, wherein the method comprises applying the water-soluble barrier layer at the first spray rate until about 1.25% (w/w) of the water-soluble barrier layer is added to the tablet core and then applying the water-soluble barrier layer at the second spray rate.

113. The method of any one of paragraphs 99-105, wherein the method comprises applying the water-soluble barrier layer at the first spray rate until about 1.5% (w/w) of the water-soluble barrier layer is added to the tablet core and then applying the water-soluble barrier layer at the second spray rate.

114. The method of any one of paragraphs 99-105, wherein the method comprises applying the water-soluble barrier layer at the first spray rate until about 1.75% (w/w) of the water-soluble barrier layer is added to the tablet core and then applying the water-soluble barrier layer at the second spray rate.

115. The method of any one of paragraphs 99-105, wherein the method comprises applying the water-soluble barrier layer at the first spray rate until about 2.0% (w/w) of the water-soluble barrier layer is added to the tablet core and then applying the water-soluble barrier layer at the second spray rate.

116. The method of any one of paragraphs 106-115, wherein the water-soluble barrier layer is applied at the second spray rate until a total of about 3.0% (w/w) of the water-soluble barrier layer is added to the tablet core.

117. The method of any one of paragraphs 106-115, wherein the water-soluble barrier layer is applied at the second spray rate until a total of about 4.0% (w/w) of the water-soluble barrier layer is added to the tablet core.

118. The method of any one of paragraphs 106-115, wherein the water-soluble barrier layer is applied at the second spray rate until a total of about 5.0% (w/w) of the water-soluble barrier layer is added to the tablet core.

119. The method of any one of paragraphs 106-115, wherein the water-soluble barrier layer is applied at the second spray rate until a total of about 6.0% (w/w) of the water-soluble barrier layer is added to the tablet core.

120. The method of any one of paragraphs 106-115, wherein the water-soluble barrier layer is applied at the second spray rate until a total of about 7.0% (w/w) of the water-soluble barrier layer is added to the tablet core.

121. The method of any one of paragraphs 83-120, wherein the average product temperature during the initial spray is at least 46° C.

122. The method of paragraph 121, wherein the average product temperature during the initial spray is at least 47° C.

123. The method of paragraph 121, wherein the average product temperature during the initial spray is at least 48° C.

124. The method of paragraph 121, wherein the average product temperature during the initial spray is at least 49° C.

125. The method of paragraph 121, wherein the average product temperature during the initial spray is at least 50° C.

126. The method of any one of paragraphs 83-125, wherein the minimum product temperature during the initial spray is at least 45° C.

127. The method of any one of paragraphs 83-126, wherein the enteric coating adds about 6% to the weight of the tablet, including the tablet core and the water-soluble barrier layer.

128. The method of any one of paragraphs 83-126, wherein the enteric coating adds about 7% to the weight of the tablet, including the tablet core and the water-soluble barrier layer.

129. The method of any one of paragraphs 83-126, wherein the enteric coating adds about 8% to the weight of the tablet, including the tablet core and the water-soluble barrier layer.

130. A pharmaceutical tablet for oral delivery of calcitonin, wherein the tablet is prepared by the method of any one of paragraphs 83-129. 131. A method for treating a bone-related disease, a calcium disorder, an inflammatory disease or a degenerative disease by administering the solid oral dosage form of any one of paragraphs 1-34 and 42-75 pharmaceutical tablet of any one of paragraphs 35-41, 76-82 and 131 to a subject in need thereof.

132. The method of paragraph 131, wherein the subject is a mammal.

133. The method of paragraph 131, wherein the subject is a human patient.

134. The method of any one of paragraphs 131-133, wherein bone-related disease is selected from the group consisting of osteoporosis, Paget's disease, pain associated with recent vertebral fragility fracture, and hypercalcemia of malignancy.

135. The method of any one of paragraphs 131-133, wherein the inflammatory disease is selected from the group consisting of osteoarthritis (OA), rheumatoid arthritis (RA), juvenile rheumatoid arthritis (JRA), and ankylosing spondylitis (AS).

The disclosure contemplates combinations of any of the aspects and embodiments described herein. For example, the disclosure contemplates that a tablet of the disclosure can be described using any combination of structural and/or functional features described herein, and that any such tablet may be used in any of the methods described herein.

DETAILED DESCRIPTION OF THE DISCLOSURE

Figure 1:
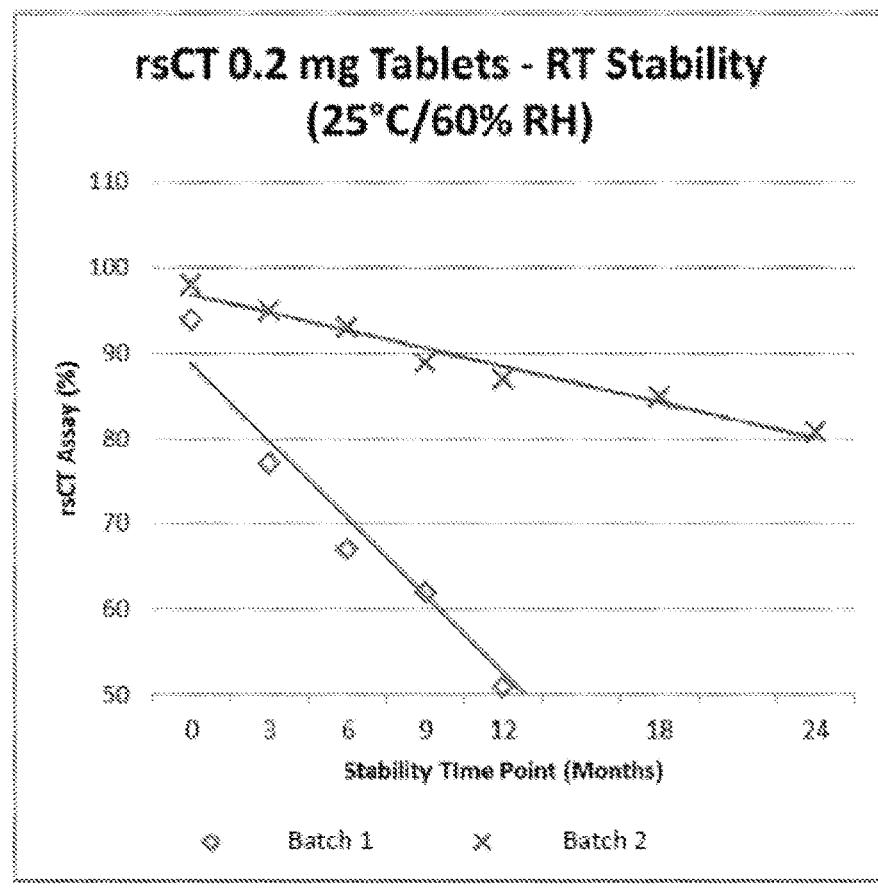
FIG. 1 demonstrates the improvement in room temperature stability (25° C. and 60% relative humidity) that is achieved when tablets are manufactured in accordance with the specifications outlined in this patent application (Batch 2, 1.8% water w/w).

In order that the disclosure described herein may be fully understood, the following detailed description is set forth.

Unless defined otherwise, all technical and scientific terms used herein have the same meaning as those commonly understood by one of skill in the art to which this disclosure belongs. Although methods and materials similar or equivalent to those described herein can be used in the practice or testing of the present disclosure, suitable methods and materials are described below. The materials, methods and examples are illustrative only, and are not intended to be limiting. All publications, patents and other documents mentioned herein are incorporated by reference in their entirety. Unless otherwise indicated, all concentrations presented as a percentage (%) are percent weight to weight (w/w).

As used herein, the term "about" modifying the quantity of an ingredient, parameter, calculation, or measurement in the compositions of the disclosure or employed in the methods of the disclosure refers to variation in the numerical quantity that can occur, for example, through typical measuring and liquid handling procedures used for making isolated polypeptides or pharmaceutical compositions in the real world; through inadvertent error in these procedures; through differences in the manufacture, source, or purity of the ingredients employed to make the compositions or carry out the methods; and the like without having a substantial effect on the chemical or physical attributes of the compositions or methods of the disclosure. Such variation can be within an order of magnitude, typically within 10%, more typically still within 5%, of a given value or range. The term "about" also encompasses amounts that differ due to different equilibrium conditions for a composition resulting from a particular initial mixture. Whether or not modified by the term "about", the claims include equivalents to the quantities.

As used herein, the term "comprising" is an open-ended term that includes the specific elements and may include additional, unrecited elements. "Comprising" may be synonymous with "including" or "containing". "Comprising" may also, separately and independently of the above definition, be read as "consisting essentially of" or "consisting of". As used herein, "consisting of" is a closed term that includes only the specific elements recited, and "consisting essentially of" includes the specific elements recited and may include additional unrecited, nonmaterial elements.

The term "room temperature," as used herein, refers to a comfortable indoor ambient temperature, e.g., at which laboratory experiments are usually performed. The U.S. Pharmacopeia defines room temperature as 20-25° C.

The terms "room-temperature stable" and "stable at room temperature," as used herein, may be used interchangeably and refer to a pharmaceutical formulation, such as a tablet or capsule, that does not require refrigeration for acceptable shelf life stability. For example, a pharmaceutical formulation that retains 80% of its biological activity for at least 24 months from the time of packaging at room temperature would be considered room-temperature stable. In some embodiments, a pharmaceutical formulation that retains 9-110% of its biological activity for at least 6 months from the time of packaging at room temperature would be considered room-temperature stable. Optionally, a pharmaceutical formulation that retains 90-110% of its biological activity for at least 9 months from the time of packaging at room temperature would be considered room-temperature stable. Room temperature stability of the oral dosage forms of calcitonin disclosed herein may be determined using an accelerated stability challenge at increased temperature and humidity. For example, a short-term accelerated stability study at 40° C. and 75% relative humidity may be predictive of long-term room-temperature stability. Similarly a short-term accelerated stability study at 50° C. and 71% relative humidity may be predictive of long-term room-temperature stability.

The term "stability," as used herein, refers to the chemical and physical integrity of a dosage unit. A stable formulation typically retains at least 80% of its biological activity. In some embodiments, a stable formulation retains at least 85% of its biological activity. Optionally, a stable formulation retains 90% of its biological activity. Stability is typically measured over an extended period of time. Taking into account expected supply-chain and distribution storage conditions, a pharmaceutical composition, such as a tablet, should be stable for at least 6 months from the time of packaging. In some embodiments, the pharmaceutical composition is stable for at least 9 months from the time of packaging.

The term "subject," as used herein, refers to a mammal. In some embodiments, the subject is a human patient. In some embodiments, the subject is an animal, such as a companion animal, such as a dog or a horse. In certain embodiments, the subject is suffering from a bone-related disorder, a calcium disorder, bone pain, an inflammatory disease or a degenerative disease.

The term "therapeutically effective amount," as used herein, refers to an amount of a polypeptide or composition comprising a polypeptide which is effective in eliciting a response in a vertebrate host. For example, a therapeutically effective amount of calcitonin may be an amount that is effective in treating or preventing a bone-related disorder, a calcium disorder, bone pain, an inflammatory disease or a degenerative disease in a subject. For example, a therapeutically effective amount of calcitonin may reduce bone loss; subchondral bone loss; alkaline phosphatase levels (e.g., in subjects suffering from Paget's disease); pain, including pain associated with Paget's disease, ankylosing spondylitis, or a recent fragility fracture and pain in an arthritic joint; and cartilage loss. Optionally, a therapeutically effective amount of calcitonin may stimulate cartilage synthesis or improve mobility in a subject suffering from arthritis. It is understood that any single dose of a therapeutically effective amount contributes to any overall observable response. The particular "therapeutically effective dosage or amount" will depend upon the age, weight and medical condition of the host, as well as on the method of administration. Suitable doses are readily determined by persons skilled in the art.

GENERAL DESCRIPTION

The present disclosure arises out of the unexpected observation that the relative water content in solid oral calcitonin dosage forms impacted the room-temperature stability. Tablets having greater water content were less stable at room temperature and required refrigeration. Tablets having less water content were more stable at room temperature, alleviating the need for refrigeration. Decreasing the water content increased the amount of recoverable intact biologically active salmon calcitonin. Without wishing to be bound by theory, the lower water content in addition to reducing the level of acid catalyzed peptide hydrolysis may preserve the potency and recoverable peptide content from the tablet. As discussed in more detail below, achieving sufficiently low water content to realize this benefit to stability was particularly difficult because standard techniques typically introduce water content into the solid dosage form.

Peptide based therapeutics due to their potency require relatively little amounts of the molecule to be biologically active; for instance injectable doses of sCT range from 8-16 μg and nasal calcitonin products contain 33 μgs of sCT. When considering a solid dosage form whose core may contain up to 1000 mg of excipients the amount of mass contributed by the peptide is small. If, for example, the peptide content of a tablet is 200 μg and the mass of the tablet is 1000 mg there is 5000 times more mass associated with the tablet components than the active ingredient.

From a manufacturing perspective this ratio (excipients: active ingredient) creates a problem when trying to achieve "content uniformity" which means that each tablet contains the intended dose of peptide. To overcome this problem, a typical approach in the art is to dissolve the peptide in an aqueous buffer or water to perform steps such as "wet granulation" that assists in the uniform dispersion of the peptide with the tablet components. This approach was used for example in the generation of bi-layer calcitonin tablets (U.S. Publication No. 2003/0017203) to assure content uniformity.

Dry blend with compression is preferred because the wet granulation technique leads to acid catalyzed hydrolysis of the peptide by the acid component (which is present in large excess when compared with the peptide) when stored at room temperature. Under refrigerated conditions the rate of this acid catalyzed hydrolysis is reduced substantially and allows for acceptable shelf life stability. Having a tablet with room temperature stability provides a significant improvement in convenience for patients and physicians alike. The present disclosure describes changes to the tablet core and the application of the sub-coat and enteric coat that result in a room temperature stable tablet.

To reduce tablet core moisture content, excipients with low moisture content were sourced. In addition, the manufacturing specification for the water content of the peptide(s) was reduced from <10% to <5%. To further reduce water content, a dry blend direct compression process was developed to manufacture the tablet cores with low water content. The process included a series of steps including low energy milling of the peptide with the excipients that allowed for dry blending of the manufacturing excipients with the peptide which achieved acceptable content uniformity.

The development of a tablet core with the requisite properties to support room temperature stability is the first step of the manufacturing process. The use of a barrier coating and pH sensitive enteric coating to deliver the solid dosage form to the proximal region of the intestine for drug delivery has been previously described (see, e.g., U.S. Pat. No. 8,377,863, incorporated by reference herein in its entirety). The barrier coating and outer enteric coating ensure that the tablet does not open in the stomach where the peptide would be degraded by gastric enzymes. The combination of the barrier coating (e.g., 6% (w/w) of the tablet core) and enteric coating (e.g., 7% (w/w) of the barrier-coated tablet core (i.e., the tablet core and barrier coat)) provides a mechanism to achieve rapid coordinated release of the drug and the excipients in the proximal intestine. This coordinated release of an pH modifying agent and the peptide are crucial to achieve acceptable bioavailability. Despite the use of selected excipients and dry blending to generate a tablet core with minimal water content, water content in the tablet core was found to increase following addition of the barrier coating and enteric coating when using industry standard techniques.

Methods of Coating a Tablet Core

The standard pharmaceutical coating materials used for coating the core tablets are both aqueous soluble agents that are applied to the tablets in a spray drying coater. Standard spray coating techniques, however, were found to introduce water content to the tablet core. The present disclosure provides conditions that were developed to prevent the ingress of water into the tablet core and to limit accumulation of water within the tablet core and/or at the tablet core/barrier coat interface, which would otherwise undermine the manufacture of a tablet core with low water content. As a result, the present disclosure provides both new methods, as well as new pharmaceutical tablets. The development of spray rates temperatures and airflow velocity minimize the observed increases in tablet water content and thereby reduce the likelihood and extent of acid catalyzed hydrolysis of peptide bonds and loss of peptide potency by binding to carbohydrate moieties present in the excipients. Alternatively, a water soluble barrier coating may be prepared and applied using non-aqueous (organic) solvents, such as isopropyl alcohol or methylene chloride. The water soluble barrier coating may be applied using a mixture of water and a non-aqueous solvent, e.g., 70% isopropyl alcohol and 30% water.

The sub-coating process may be carried out in two stages. In the first stage, the coating solution is sprayed at a low rate, using elevated drying temperatures and dry coating conditions. The objective is to prevent moisture penetration into the tablet core. After a certain amount of weight gain has been achieved, the spray rate may be increased to accelerate coating weight gain in the second stage of application. The accelerated spray rate helps ensure tablet quality; applying the entire sub-coating (i.e., barrier coating) at the low rate of the first stage may result in edge erosion, which may impact the function of the enteric coating applied over the sub-coat. Further, use of a single, low spray rate application may sacrifice a pharmaceutically elegant coating, resulting in pitting or an orange peel appearance, which may impact subsequent tablet imprinting, which helps with tablet identification. Further, the prolonged elevated drying temperatures of first-stage coating may negatively impact the peptide drug substance due to heat-induced denaturation and inactivation. A two-stage process, however, has been shown herein to minimize the impact of water ingress on the tablet core or water trapped at the tablet core/barrier coat interface, while maintaining tablet quality, including surface integrity.

Accordingly, aspects of the present disclosure provides a method for spray coating a tablet core for oral delivery of calcitonin. In some embodiments, the method minimizes the amount of water absorbed onto the tablet core during the coating process. Preferably, no or substantially no water is absorbed onto the tablet core during the coating process. In some embodiments, the coating process actually reduces the amount of water present in the tablet core.

In some embodiments, the method for spray coating a tablet core for oral delivery of calcitonin comprises: (a)

providing a tablet core; (b) applying a water-soluble barrier layer in an initial spray at a first spray rate sufficient to add approximately 0.25% (w/w) of the water-soluble barrier layer to the tablet core in about 30 minutes at an average product temperature of at least 45° C.; and (c) applying an enteric coating. Optionally, the tablet core comprises (i) calcitonin intermixed with coated citric acid particles, (ii) crospovidone; (iii) copovidone; (iv) microcrystalline cellulose; and (v) magnesium stearate. In some embodiments, the microcrystalline cellulose is silicified microcrystalline cellulose.

In some embodiments, the tablet core contains no more than 2.5% (w/w) water prior to the spray coating steps. In some embodiments, the tablet contains less than 2.5% (w/w) water prior to the spray coating steps. Optionally, the tablet core contains no more than 2.25% (w/w) water prior to the spray coating steps. Optionally, the tablet core contains no more than 2.20% (w/w) water prior to the spray coating steps. In some embodiments, the tablet core contains no more than 2.15% (w/w) water prior to the spray coating steps. Optionally, the tablet core contains no more than 2.10% (w/w) water prior to the spray coating steps. In some embodiments, the tablet core contains no more than 2.05% (w/w) water prior to the spray coating steps. Optionally, the tablet core contains no more than 2.0% (w/w) water prior to the spray coating steps. In some embodiments, the tablet core contains no more than 1.95% (w/w) water prior to the spray coating steps. Optionally, the tablet core contains no more than 1.9% (w/w) water prior to the spray coating steps. In some embodiments, the tablet core contains no more than 1.85% (w/w) water prior to the spray coating steps. Optionally, the tablet core contains no more than 1.8% (w/w) water prior to the spray coating steps. In some embodiments, the tablet core contains no more than 1.75% (w/w) water prior to the spray coating steps. Optionally, the tablet core contains no more than 1.7% (w/w) water prior to the spray coating steps. In some embodiments, the tablet core contains no more than 1.65% (w/w) water prior to the spray coating steps. Optionally, the tablet core contains no more than 1.6% (w/w) water prior to the spray coating steps. In some embodiments, the tablet core contains no more than 1.55% (w/w) water prior to the spray coating steps. Optionally, the tablet core contains no more than 1.5% (w/w) water prior to the spray coating steps. In some embodiments, the tablet core contains no more than 1.45% (w/w) water prior to the spray coating steps. Optionally, the tablet core contains no more than 1.4% (w/w) water prior to the spray coating steps. In some embodiments, the tablet core contains no more than 1.35% (w/w) water prior to the spray coating steps. Optionally, the tablet core contains no more than 1.3% (w/w) water prior to the spray coating steps. In some embodiments, the tablet core contains no more than 1.25% (w/w) water prior to the spray coating steps. Optionally, the tablet core contains no more than 1.2% (w/w) water prior to the spray coating steps. In some embodiments, the tablet core contains no more than 1.15% (w/w) water prior to the spray coating steps. Optionally, the tablet core contains no more than 1.1% (w/w) water prior to the spray coating steps. In some embodiments, the tablet core contains no more than 1.05% (w/w) water prior to the spray coating steps. Optionally, the tablet core contains no more than 1.0% (w/w) water prior to the spray coating steps. In some embodiments, the tablet core contains no more than 0.95% (w/w) water prior to the spray coating steps. Optionally, the tablet core contains no more than 0.9% (w/w) water prior to the spray coating steps. In some embodiments, the tablet core contains no more than 0.85% (w/w) water prior to the spray coating steps. Optionally, the tablet core contains no more than 0.8% (w/w) water prior to the spray coating steps. In some embodiments, the water content of the tablet core is determined by Karl Fischer titration, such as Karl Fischer Coulometric Titration Method 1c.

In some embodiments, the total acid in the tablet core is in a quantity which, if added to ten milliliters of 0.1 M aqueous sodium bicarbonate solution, would be sufficient to lower the pH of said solution to no higher than 5.5. Optionally, the tablet does not include an amount of base which, if released together with the acid, would prevent the pH of said solution from dropping to 5.5 or below. The acid may be selected from citric acid, tartaric acid and an acid salt of an amino acid. Optionally, the acid is citric acid. In some embodiments, the coating on the acid particles is a pharmaceutically acceptable protective coating that is non-acidic and has a solubility in water of at least one gram per 100 milliliters of water at room temperature. In some embodiments, the protective coating of the coated acid particles is a sugar. Optionally, the sugar is glucose. The sugar may be maltodextrin.

In some embodiments, the calcitonin is selected from the group consisting of human calcitonin, salmon calcitonin, eel calcitonin, elkatonin, porcine calcitonin, and chicken calcitonin. Optionally, the calcitonin is salmon calcitonin. The salmon calcitonin may have the amino acid sequence of CSNLSTCVLGKLSQELHKLQTYPRTNTGSGTP-NH$_2$ (SEQ ID NO: 1), wherein P—NH$_2$ represents an amidated proline. The tablet may comprise about 100 to about 1000 µg salmon calcitonin. The tablet may comprise about 100 to about 500 µg salmon calcitonin, such as 100 to 300 µg or 100 to 250 µg. In some embodiments, the tablet comprises about 100 µg salmon calcitonin. Optionally, the tablet comprises about 150 µg salmon calcitonin. In some embodiments, the tablet comprises about 200 µg salmon calcitonin. Optionally, the tablet comprises about 250 µg salmon calcitonin. In some embodiments, the tablet comprises about 300 µg salmon calcitonin. Optionally, the tablet comprises about 350 µg salmon calcitonin. In some embodiments, the tablet comprises about 400 µg salmon calcitonin. Optionally, the tablet comprises about 450 µg salmon calcitonin. In some embodiments, the tablet comprises about 500 µg salmon calcitonin. Preferably, the tablet comprises about 200 µg salmon calcitonin. Optionally, the coated citric acid particles are maltodextrin-coated citric acid particles. In some embodiments, the tablet core comprises (i) about 0.01% (w/w) to about 0.10% (w/w) salmon calcitonin; (ii) about 62% (w/w) maltodextrin-coated citric acid; (iii) about 1.1% (w/w) crospovidone; (iv) about 5% (w/w) copovidone; (v) about 31% (w/w) silicified microcrystalline cellulose; and (vi) about 0.5% (w/w) magnesium stearate. Optionally, the tablet core comprises about 0.02% (w/w) salmon calcitonin.

In some embodiments, the tablet may contain one or more additional pharmaceutical excipients. In some embodiments, the one or more additional pharmaceutical excipients are in the tablet core. Non-limiting examples of additional pharmaceutical excipients include absorption enhancers (e.g., solubility enhancers and transport enhancers), fillers, binders, glidants, antioxidants, additional peptides, carriers, diluents, preservatives, and colorants. The use of such excipients is disclosed, infra.

In some embodiments, the water-soluble barrier layer comprises hydroxypropylmethylcellulose, hydroxypropylcellulose, methylcellulose, polyvinylpyrolidone, or a polyvinyl alcohol-polyethylene glycol graft copolymer, such as a polyvinyl alcohol-polyethylene glycol graft copolymer. The enteric coating may be selected from the group consisting of cellulose acetate phthalate, hydroxypropyl methylethylcellulose succinate, hydroxypropyl methylcellulose phthalate, carboxyl methylethylcellulose, methacrylic acid-methyl methacrylate copolymer, and methacrylic acid-ethyl acrylate. Optionally, the enteric coating comprises a methacrylic acid-ethyl acrylate copolymer (1:1).

In some embodiments, the first spray rate is sufficient to add approximately 0.3% (w/w) of the water-soluble barrier layer to the tablet core in about 30 minutes. Optionally, the first spray rate is sufficient to add approximately 0.35% (w/w) of the water-soluble barrier layer to the tablet core in about 30 minutes. The first spray rate may be sufficient to add approximately 0.4% (w/w) of the water-soluble barrier layer to the tablet core in about 30 minutes. In some embodiments, the first spray rate is sufficient to add approximately 0.45% (w/w) of the water-soluble barrier layer to the tablet core in about 30 minutes. Optionally, the first spray rate is sufficient to add approximately 0.5% (w/w) of the water-soluble barrier layer to the tablet core in about 30 minutes. It is contemplated that the initial spray time may be, for example, 30 minutes or may be more or less than 30 minutes.

In some embodiments, the first spray rate is such that no more than 0.5% (w/w) of the water-soluble barrier layer is added to the tablet core in about 30 minutes. Optionally, the first spray rate is such that no more than 0.45% (w/w) of the water-soluble barrier layer is added to the tablet core in about 30 minutes. The first spray rate may be such that no more than 0.4% (w/w) of the water-soluble barrier layer is added to the tablet core in about 30 minutes. In some embodiments, the first spray rate is such that no more than 0.35% (w/w) of the water-soluble barrier layer is added to the tablet core in about 30 minutes. Optionally, the first spray rate is such that no more than 0.3% (w/w) of the water-soluble barrier layer is added to the tablet core in about 30 minutes. The first spray rate may be such that no more than 0.25% (w/w) of the water-soluble barrier layer is added to the tablet core in about 30 minutes.

In some embodiments of any of the above methods, after applying the water-soluble barrier layer at the first spray rate for at least 30 minutes, the water-soluble barrier layer is applied in a subsequent spray at a second spray rate, which is faster than the first spray rate. The water-soluble barrier layer may be applied at the first spray rate for at least 45 minutes before applying the water-soluble barrier layer at the second spray rate. Optionally, the water-soluble barrier layer is applied at the first spray rate for at least 60 minutes before applying the water-soluble barrier layer at the second spray rate. In some embodiments, the water-soluble barrier layer is applied at the first spray rate for at least 75 minutes before applying the water-soluble barrier layer at the second spray rate. Optionally, the water-soluble barrier layer is applied at the first spray rate for at least 90 minutes before applying the water-soluble barrier layer at the second spray rate. In some embodiments, the water-soluble barrier layer is applied at the first spray rate for at least 105 minutes before applying the water-soluble barrier layer at the second spray rate. Optionally, the water-soluble barrier layer is applied at the first spray rate for at least 120 minutes before applying the water-soluble barrier layer at the second spray rate.

In some embodiments of any of the above methods, after applying the water-soluble barrier layer at the first spray rate for about 30 minutes, the water-soluble barrier layer is applied in a subsequent spray (which may be, for example, from the same or a different nozzle) at a second spray rate, which is faster than the first spray rate. The water-soluble barrier layer may be applied at the first spray rate for about 45 minutes before applying the water-soluble barrier layer at the second spray rate. Optionally, the water-soluble barrier layer is applied at the first spray rate for about 60 minutes before applying the water-soluble barrier layer at the second spray rate. In some embodiments, the water-soluble barrier layer is applied at the first spray rate for about 75 minutes before applying the water-soluble barrier layer at the second spray rate. Optionally, the water-soluble barrier layer is applied at the first spray rate for about 90 minutes before applying the water-soluble barrier layer at the second spray rate. In some embodiments, the water-soluble barrier layer is applied at the first spray rate for about 105 minutes before applying the water-soluble barrier layer at the second spray rate. Optionally, the water-soluble barrier layer is applied at the first spray rate for about 120 minutes before applying the water-soluble barrier layer at the second spray rate.

In some embodiments, the subsequent spray is performed with the same nozzle as the initial spray. Optionally, the subsequent spray is performed with a different nozzle than the initial spray.

In some embodiments of any of the above methods, the second spray rate is at least 1.4 times faster than the first spray rate. Optionally, the second spray rate is at least 1.5 times faster than the first spray rate. The second spray rate may be at least 1.6 times faster than the first spray rate. In some embodiments of any of the above methods, the second spray rate is at least 1.7 times faster than the first spray rate. Optionally, the second spray rate is at least 1.8 times faster than the first spray rate. The second spray rate may be at least 1.9 times faster than the first spray rate. In some embodiments of any of the above methods, the second spray rate is at least 2.0 times faster than the first spray rate. Optionally, the second spray rate is at least 2.1 times faster than the first spray rate. The second spray rate may be at least 2.2 times faster than the first spray rate. In some embodiments of any of the above methods, the second spray rate is at least 2.3 times faster than the first spray rate. Optionally, the second spray rate is at least 2.4 times faster than the first spray rate. The second spray rate may be at least 2.5 times faster than the first spray rate. In some embodiments of any of the above methods, the second spray rate is at least 2.75 times faster than the first spray rate. Optionally, the second spray rate is at least 3.0 times faster than the first spray rate.

In some embodiments of any of the above methods, the second spray rate is about 1.4 times faster than the first spray rate. Optionally, the second spray rate is about 1.5 times faster than the first spray rate. The second spray rate may be about 1.6 times faster than the first spray rate. In some embodiments of any of the above methods, the second spray rate is about 1.7 times faster than the first spray rate. Optionally, the second spray rate is about 1.8 times faster than the first spray rate. The second spray rate may be about 1.9 times faster than the first spray rate. In some embodiments of any of the above methods, the second spray rate is about 2.0 times faster than the first spray rate. Optionally, the second spray rate is about 2.1 times faster than the first spray rate. The second spray rate may be about 2.2 times faster than the first spray rate. In some embodiments of any of the above methods, the second spray rate is about 2.3 times faster than the first spray rate. Optionally, the second spray rate is about 2.4 times faster than the first spray rate. The second spray rate may be about 2.5 times faster than the first spray rate. In some embodiments of any of the above methods, the second spray rate is about 2.75 times faster than the first spray rate. Optionally, the second spray rate is about 3.0 times faster than the first spray rate.

In some embodiments, the second spray rate is sufficient to add about 5.5% (w/w) of the water-soluble barrier layer to the tablet core. In some embodiments, the second spray rate is sufficient to add about 5.5% (w/w) of the water-soluble barrier layer to the tablet core in about four and a half hours. Optionally, the second spray rate is sufficient to add about 5.5% (w/w) of the water-soluble barrier layer to the tablet core in about four hours. The second spray rate may be sufficient to add about 5.5% (w/w) of the water-soluble barrier layer to the tablet core in about three and a half hours. In some embodiments, the second spray rate is sufficient to add about 5.5% (w/w) of the water-soluble barrier layer to the tablet core in about three hours. The second spray rate may be sufficient to add about 5.5% (w/w) of the water-soluble barrier layer to the tablet core in about two and a half hours. Optionally, the second spray rate is sufficient to add about 5.5% (w/w) of the water-soluble barrier layer to the tablet core in about two hours. The second spray rate may be sufficient to add about 5.5% (w/w) of the water-soluble barrier layer to the tablet core in about one and a half hours.

In some embodiments, the method comprises applying the water-soluble barrier layer at the first spray rate until about 0.5% (w/w) of the water-soluble barrier layer is added to the tablet core and then applying the water-soluble barrier layer at the second spray rate. Optionally, the method comprises applying the water-soluble barrier layer at the first spray rate until about 0.6% (w/w) of the water-soluble barrier layer is added to the tablet core and then applying the water-soluble barrier layer at the second spray rate. In some embodiments, the method comprises applying the water-soluble barrier layer at the first spray rate until about 0.7% (w/w) of the water-soluble barrier layer is added to the tablet core and then applying the water-soluble barrier layer at the second spray rate. The method may comprise applying the water-soluble barrier layer at the first spray rate until about 0.8% (w/w) of the water-soluble barrier layer is added to the tablet core and then applying the water-soluble barrier layer at the second spray rate. Optionally, the method comprises applying the water-soluble barrier layer at the first spray rate until about 0.9% (w/w) of the water-soluble barrier layer is added to the tablet core and then applying the water-soluble barrier layer at the second spray rate. In some embodiments, the method comprises applying the water-soluble barrier layer at the first spray rate until about 1.0% (w/w) of the water-soluble barrier layer is added to the tablet core and then applying the water-soluble barrier layer at the second spray rate. Optionally, the method comprises applying the water-soluble barrier layer at the first spray rate until about 1.25% (w/w) of the water-soluble barrier layer is added to the tablet core and then applying the water-soluble barrier layer at the second spray rate. In some embodiments, the method comprises applying the water-soluble barrier layer at the first spray rate until about 1.5% (w/w) of the water-soluble barrier layer is added to the tablet core and then applying the water-soluble barrier layer at the second spray rate. Optionally, the method comprises applying the water-soluble barrier layer at the first spray rate until about 1.75% (w/w) of the water-soluble barrier layer is added to the tablet core and then applying the water-soluble barrier layer at the second spray rate. In some embodiments, the method comprises applying the water-soluble barrier layer at the first spray rate until about 2.0% (w/w) of the water-soluble barrier layer is added to the tablet core and then applying the water-soluble barrier layer at the second spray rate.

In some embodiments, the water-soluble barrier layer is applied at the second spray rate until a total of about 3.0% (w/w) of the water-soluble barrier layer is added to the tablet core. Optionally, the water-soluble barrier layer is applied at the second spray rate until a total of about 4.0% (w/w) of the water-soluble barrier layer is added to the tablet core. The water-soluble barrier layer may be applied at the second spray rate until a total of about 5.0% (w/w) of the water-soluble barrier layer is added to the tablet core. In some embodiments, the water-soluble barrier layer is applied at the second spray rate until a total of about 6.0% (w/w) of the water-soluble barrier layer is added to the tablet core. In some embodiments, the water-soluble barrier layer is applied at the second spray rate until a total of about 7.0% (w/w) of the water-soluble barrier layer is added to the tablet core.

The skilled artisan would recognize that average product temperature is achieved by adjusting the inlet temperature and air flow velocity of the spray coater. It is within the skill in the art to identify the correct inlet temperature and air flow velocity of any given spray coater to achieve the desired average product temperature. In some embodiments of any of the above methods, the average product temperature (i.e., bed temperature) during the initial spray of the water-soluble barrier layer is 50° C.±5° C. Optionally, the average product temperature during the initial spray is at least 46° C. In some embodiments, the average product temperature during the initial spray is at least 47° C. Optionally, the average product temperature during the initial spray is at least 48° C. The average product temperature during the initial spray may be at least 49° C. In some embodiments, the average product temperature during the initial spray is at least 50° C. Optionally, the average product temperature during the initial spray is at least 51° C. In some embodiments, the average product temperature during the initial spray is at least 52° C. Optionally, the average product temperature during the initial spray is at least 53° C. In some embodiments, the average product temperature during the initial spray is at least 54° C.

In some embodiments, the average product temperature (i.e., bed temperature) during the initial spray of the water-soluble barrier layer is about 45° C. Optionally, the average product temperature during the initial spray is about 46° C. In some embodiments, the average product temperature during the initial spray is about 47° C. Optionally, the average product temperature during the initial spray is about 48° C. The average product temperature during the initial spray may be about 49° C. In some embodiments, the average product temperature during the initial spray is about 50° C. Optionally, the average product temperature during the initial spray is about 51° C. In some embodiments, the average product temperature during the initial spray is about 52° C. Optionally, the average product temperature during the initial spray is about 53° C. The average product temperature during the initial spray may be about 54° C. In some embodiments, the average product temperature during the initial spray is about 55° C.

In some embodiments, the average product temperature during the initial spray of the water-soluble barrier layer is at most 55° C. Optionally, the average product temperature during the initial spray is at most 54° C. The average product temperature during the initial spray may be at most 53° C. In some embodiments, the average product temperature during the initial spray is at most 52° C. Optionally, the average product temperature during the initial spray is at most 51° C. In some embodiments, the average product temperature during the initial spray is at most 50° C. Optionally, the average product temperature during the initial spray is at most 48° C. The average product temperature during the initial spray may be at most 48° C. In some embodiments, the average product temperature during the initial spray is at most 47° C. Optionally, the average product temperature during the initial spray is at most 46° C.

In some embodiments, the average product temperature (i.e., bed temperature) during the initial spray of the water-soluble barrier layer between is about 45° C. and about 55° C. Optionally, the average product temperature during the initial spray is between about 46° C. and about 55° C. The average product temperature during the initial spray may be between about 47° C. and about 55° C. In some embodiments, the average product temperature during the initial spray is between about 48° C. and about 55° C. Optionally, the average product temperature during the initial spray is between about 49° C. and about 55° C. In some embodiments, the average product temperature during the initial spray is between about 50° C. and about 55° C. Optionally, the average product temperature during the initial spray is between about 51° C. and about 55° C. The average product temperature during the initial spray may be between about 52° C. and about 55° C. In some embodiments, the average product temperature during the initial spray is between about 53° C. and about 55° C. In some embodiments, the average product temperature (i.e., bed temperature) during the initial spray between is about 45° C. and about 54° C. Optionally, the average product temperature during the initial spray is between about 45° C. and about 53° C. The average product temperature during the initial spray may be between about 45° C. and about 52° C. In some embodiments, the average product temperature (i.e., bed temperature) during the initial spray between is about 45° C. and about 51° C. Optionally, the average product temperature during the initial spray is between about 45° C. and about 50° C. The average product temperature during the initial spray may be between about 45° C. and about 49° C. In some embodiments, the average product temperature (i.e., bed temperature) during the initial spray between is about 45° C. and about 48° C. Optionally, the average product temperature during the initial spray is between about 45° C. and about 47° C. The average product temperature during the initial spray may be between about 46° C. and about 54° C. In some embodiments, the average product temperature (i.e., bed temperature) during the initial spray between is about 46° C. and about 53° C. Optionally, the average product temperature during the initial spray is between about 47° C. and about 54° C. The average product temperature during the initial spray may be between about 47° C. and about 53° C. In some embodiments, the average product temperature (i.e., bed temperature) during the initial spray between is about 48° C. and about 54° C. Optionally, the average product temperature during the initial spray is between about 48° C. and about 53° C. The average product temperature during the initial spray may be between about 49° C. and about 54° C. In some embodiments, the average product temperature (i.e., bed temperature) during the initial spray between is about 49° C. and about 53° C. Optionally, the average product temperature during the initial spray is between about 50° C. and about 54° C. The average product temperature during the initial spray may be between about 50° C. and about 53° C. In some embodiments, the average product temperature (i.e., bed temperature) during the initial spray between is about 51° C. and about 54° C. Optionally, the average product temperature during the initial spray is between about 51° C. and about 53° C. The average product temperature during the initial spray may be between about 47° C. and about 52° C. In some embodiments, the average product temperature (i.e., bed temperature) during the initial spray between is about 47° C. and about 51° C. Optionally, the average product temperature during the initial spray is between about 47° C. and about 50° C. The average product temperature during the initial spray may be between about 49° C. and about 51° C.

In some embodiments, the minimum product temperature during the initial spray of the water-soluble barrier layer is at least 40° C. Optionally, the minimum product temperature during the initial spray is at least 41° C. The minimum product temperature during the initial spray may be at least 42° C. In some embodiments, the minimum product temperature during the initial spray is at least 43° C. Optionally, the minimum product temperature during the initial spray is at least 44° C. In some embodiments, the minimum product temperature during the initial spray is at least 45° C. Optionally, the minimum product temperature during the initial spray is at least 46° C. In some embodiments, the minimum product temperature during the initial spray is at least 47° C. In some embodiments, the minimum product temperature during the initial spray is at least 48° C. Optionally, the minimum product temperature during the initial spray is at least 49° C.

In some embodiments, the minimum product temperature during the initial spray of the water-soluble barrier layer is about 40° C. Optionally, the minimum product temperature during the initial spray is about 41° C. The minimum product temperature during the initial spray may be about 42° C. In some embodiments, the minimum product temperature during the initial spray is about 43° C. Optionally, the minimum product temperature during the initial spray is about 44° C. In some embodiments, the minimum product temperature during the initial spray is about 45° C. Optionally, the minimum product temperature during the initial spray is about 46° C. In some embodiments, the minimum product temperature during the initial spray is about 47° C. In some embodiments, the minimum product temperature during the initial spray is about 48° C. Optionally, the minimum product temperature during the initial spray is about 49° C.

In some embodiments, the maximum product temperature during the initial spray of the water-soluble barrier layer is at most 55° C. Optionally, the maximum product temperature during the initial spray is at most 54° C. The maximum product temperature during the initial spray may be at most 53° C. In some embodiments, the maximum product temperature during the initial spray is at most 52° C. Optionally, the maximum product temperature during the initial spray is at most 51° C. In some embodiments, the maximum product temperature during the initial spray is at most 50° C. Optionally, the maximum product temperature during the initial spray is at most 49° C. The maximum product temperature during the initial spray may be at most 48° C. In some embodiments, the maximum product temperature during the initial spray is at most 46° C. Optionally, the maximum product temperature during the initial spray is at most 46° C.

In some embodiments, the maximum product temperature during the initial spray of the water-soluble barrier layer is about 55° C. Optionally, the maximum product temperature during the initial spray is about 54° C. The maximum product temperature during the initial spray may be about 53° C. In some embodiments, the maximum product temperature during the initial spray is about 52° C. Optionally, the maximum product temperature during the initial spray is about 51° C. In some embodiments, the maximum product temperature during the initial spray is about 50° C. Optionally, the maximum product temperature during the initial spray is about 49° C. The maximum product temperature during the initial spray may be about 48° C. In some embodiments, the maximum product temperature during the initial spray is about 47° C. Optionally, the maximum product temperature during the initial spray is about 46° C.

In some embodiments of any of the above methods, the average product temperature (i.e., bed temperature) during the subsequent spray of the water-soluble barrier layer is 45° C.±5° C. In some embodiments, the average product temperature (i.e., bed temperature) during the subsequent spray of the water-soluble barrier layer is at least 40° C. In some embodiments, the average product temperature during the subsequent spray is at least 41° C. Optionally, the average product temperature during the subsequent spray is at least 42° C. In some embodiments, the average product temperature during the subsequent spray is at least 43° C. Optionally, the average product temperature during the subsequent spray is at least 44° C. The average product temperature during the subsequent spray may be at least 45° C. In some embodiments, the average product temperature during the subsequent spray is at least 46° C. Optionally, the average product temperature during the subsequent spray is at least 47° C. In some embodiments, the average product temperature during the subsequent spray is at least 48° C. Optionally, the average product temperature during the subsequent spray is at least 49° C. In some embodiments, the average product temperature during the subsequent spray is at least 50° C.

In some embodiments, the average product temperature (i.e., bed temperature) during the subsequent spray of the water-soluble barrier layer is about 40° C. In some embodiments, the average product temperature during the subsequent spray is about 41° C. Optionally, the average product temperature during the subsequent spray is about 42° C. In some embodiments, the average product temperature during the subsequent spray is about 43° C. Optionally, the average product temperature during the subsequent spray is about 44° C. The average product temperature during the subsequent spray may be about 45° C. In some embodiments, the average product temperature during the subsequent spray is about 46° C. Optionally, the average product temperature during the subsequent spray is about 47° C. In some embodiments, the average product temperature during the subsequent spray is about 48° C. The average product temperature during the subsequent spray may be about 49° C. In some embodiments, the average product temperature during the subsequent spray is about 50° C.

In some embodiments, the average product temperature during the initial spray of the water-soluble barrier layer is at most 50° C. Optionally, the average product temperature during the initial spray is at most 49° C. The average product temperature during the initial spray may be at most 48° C. In some embodiments, the average product temperature during the initial spray is at most 47° C. Optionally, the average product temperature during the initial spray is at most 46° C. In some embodiments, the average product temperature during the initial spray is at most 45° C. Optionally, the average product temperature during the initial spray is at most 44° C. The average product temperature during the initial spray may be at most 43° C. In some embodiments, the average product temperature during the initial spray is at most 42° C. Optionally, the average product temperature during the initial spray is at most 41° C.

In some embodiments, the average product temperature (i.e., bed temperature) during the subsequent spray of the water-soluble barrier layer is between about 40° C. and about 50° C. Optionally, the average product temperature during the subsequent spray is between about 41° C. and about 50° C. The average product temperature during the subsequent spray may be between about 42° C. and about 50° C. In some embodiments, the average product temperature during the subsequent spray is between about 43° C. and about 50° C. Optionally, the average product temperature during the subsequent spray is between about 44° C. and about 50° C. In some embodiments, the average product temperature during the subsequent spray is between about 45° C. and about 50° C. Optionally, the average product temperature during the subsequent spray is between about 46° C. and about 50° C. The average product temperature during the subsequent spray may be between about 47° C. and about 50° C. In some embodiments, the average product temperature during the subsequent spray is between about 48° C. and about 50° C. Optionally, the average product temperature during the subsequent spray is between about 40° C. and about 49° C. The average product temperature during the subsequent spray may be between about 40° C. and about 48° C. In some embodiments, the average product temperature during the subsequent spray is between about 40° C. and about 47° C. Optionally, the average product temperature during the subsequent spray is between about 40° C. and about 46° C. The average product temperature during the subsequent spray may be between about 40° C. and about 45° C. In some embodiments, the average product temperature during the subsequent spray is between about 40° C. and about 44° C. Optionally, the average product temperature during the subsequent spray is between about 40° C. and about 43° C. The average product temperature during the subsequent spray may be between about 40° C. and about 42° C. In some embodiments, the average product temperature during the subsequent spray is between about 41° C. and about 49° C. Optionally, the average product temperature during the subsequent spray is between about 48° C. and about 48° C. The average product temperature during the subsequent spray may be between about 43° C. and about 47° C. In some embodiments, the average product temperature during the subsequent spray is between about 44° C. and about 46° C.

In some embodiments, the minimum product temperature during the subsequent spray of the water-soluble barrier layer is at least 40° C. Optionally, the minimum product temperature during the subsequent spray is at least 41° C. The minimum product temperature during the subsequent spray may be at least 42° C. In some embodiments, the minimum product temperature during the subsequent spray is at least 43° C. Optionally, the minimum product temperature during the subsequent spray is at least 44° C. In some embodiments, the minimum product temperature during the subsequent spray is at least 45° C. Optionally, the minimum product temperature during the subsequent spray is at least 46° C. The minimum product temperature during the subsequent spray may be at least 47° C. In some embodiments, the minimum product temperature during the subsequent spray is at least 48° C. Optionally, the minimum product temperature during the subsequent spray is at least 49° C.

In some embodiments, the minimum product temperature during the subsequent spray of the water-soluble barrier layer is about 40° C. Optionally, the minimum product temperature during the subsequent spray is about 41° C. The minimum product temperature during the subsequent spray may be about 42° C. In some embodiments, the minimum product temperature during the subsequent spray is about 43° C. Optionally, the minimum product temperature during the subsequent spray is about 44° C. In some embodiments, the minimum product temperature during the subsequent spray is about 45° C. Optionally, the minimum product temperature during the subsequent spray is about 46° C. The minimum product temperature during the subsequent spray may be about 47° C. In some embodiments, the minimum product temperature during the subsequent spray is about 48° C. Optionally, the minimum product temperature during the subsequent spray is about 49° C.

In some embodiments, the maximum product temperature during the subsequent spray of the water-soluble barrier layer is at most 43° C. Optionally, the maximum product temperature during the subsequent spray is at most 44° C. In some embodiments, the maximum product temperature during the subsequent spray is at most 45° C. Optionally, the maximum product temperature during the subsequent spray is at most 46° C. The maximum product temperature during the subsequent spray may be at most 47° C. In some embodiments, the maximum product temperature during the subsequent spray is at most 48° C. Optionally, the maximum product temperature during the subsequent spray is at most 49° C. In some embodiments, the maximum product temperature during the subsequent spray is at most 50° C.

In some embodiments, the maximum product temperature during the subsequent spray of the water-soluble barrier layer is about 43° C. Optionally, the maximum product temperature during the subsequent spray is about 44° C. In some embodiments, the maximum product temperature during the subsequent spray is about 45° C. Optionally, the maximum product temperature during the subsequent spray is about 46° C. The maximum product temperature during the subsequent spray may be about 47° C. In some embodiments, the maximum product temperature during the subsequent spray is about 48° C. Optionally, the maximum product temperature during the subsequent spray is about 49° C. In some embodiments, the maximum product temperature during the subsequent spray is about 50° C.

In some embodiments, the enteric coating adds about 4% to the weight of the tablet, including the tablet core and the water-soluble barrier layer. Optionally, the enteric coating adds about 4.5% to the weight of the tablet, including the tablet core and the water-soluble barrier layer. In some embodiments, the enteric coating adds about 5% to the weight of the tablet, including the tablet core and the water-soluble barrier layer. Optionally, the enteric coating adds about 5.5% to the weight of the tablet, including the tablet core and the water-soluble barrier layer. In some embodiments, the enteric coating adds about 6% to the weight of the tablet, including the tablet core and the water-soluble barrier layer. Optionally, the enteric coating adds about 6.5% to the weight of the tablet, including the tablet core and the water-soluble barrier layer. In some embodiments, the enteric coating adds about 7% to the weight of the tablet, including the tablet core and the water-soluble barrier layer. Optionally, the enteric coating adds about 7.5% to the weight of the tablet, including the tablet core and the water-soluble barrier layer. In some embodiments, the enteric coating adds about 8% to the weight of the tablet, including the tablet core and the water-soluble barrier layer.

In some embodiments, a tablet of the disclosure, such as a tablet produced by the methods described herein, contains no more than 2.5% (w/w) water. In some embodiments, the tablet contains less than 2.5% (w/w) water. Optionally, the tablet contains no more than 2.25% (w/w) water. Optionally, the tablet contains no more than 2.20% (w/w) water. In some embodiments, the tablet contains no more than 2.15% (w/w) water. Optionally, the tablet contains no more than 2.10% (w/w) water. In some embodiments, the tablet contains no more than 2.05% (w/w) water. Optionally, the tablet contains no more than 2.0% (w/w) water. In some embodiments, the tablet contains no more than 1.95% (w/w) water. Optionally, the tablet contains no more than 1.9% (w/w) water. In some embodiments, the tablet contains no more than 1.85% (w/w) water. Optionally, the tablet contains no more than 1.8% (w/w) water. In some embodiments, the tablet contains no more than 1.75% (w/w) water. Optionally, the tablet contains no more than 1.7% (w/w) water. In some embodiments, the tablet contains no more than 1.65% (w/w) water. Optionally, the tablet contains no more than 1.6% (w/w) water. In some embodiments, the tablet contains no more than 1.55% (w/w) water. Optionally, the tablet contains no more than 1.5% (w/w) water. In some embodiments, the tablet contains no more than 1.45% (w/w) water. Optionally, the tablet contains no more than 1.4% (w/w) water. In some embodiments, the tablet contains no more than 1.35% (w/w) water. Optionally, the tablet contains no more than 1.3% (w/w) water. In some embodiments, the tablet contains no more than 1.25% (w/w) water. Optionally, the tablet contains no more than 1.2% (w/w) water. In some embodiments, the tablet contains no more than 1.15% (w/w) water. Optionally, the tablet contains no more than 1.1% (w/w) water. In some embodiments, the tablet contains no more than 1.05% (w/w) water. Optionally, the tablet contains no more than 1.0% (w/w) water. In some embodiments, the tablet contains no more than 0.95% (w/w) water. Optionally, the tablet contains no more than 0.9% (w/w) water. In some embodiments, the tablet contains no more than 0.85% (w/w) water. Optionally, the tablet contains no more than 0.8% (w/w) water. In some embodiments, the tablet contains no more than 0.75% (w/w) water. Optionally, the tablet contains no more than 0.7% (w/w) water. In some embodiments, the tablet contains no more than 0.65% (w/w) water. Optionally, the tablet contains no more than 0.6% (w/w) water. In some embodiments, the water content of the tablet is determined by Karl Fischer titration, such as Karl Fischer Coulometric Titration Method 1c.

In some embodiments, a tablet of the disclosure, such as a tablet produced by the methods described herein, contains about 2.5% (w/w) water. Optionally, the tablet contains about 2.25% (w/w) water. Optionally, the tablet contains about 2.20% (w/w) water. In some embodiments, the tablet contains about 2.15% (w/w) water. Optionally, the tablet contains about 2.10% (w/w) water. In some embodiments, the tablet contains about 2.05% (w/w) water. Optionally, the tablet contains about 2.0% (w/w) water. In some embodiments, the tablet contains about 1.95% (w/w) water. Optionally, the tablet contains about 1.9% (w/w) water. In some embodiments, the tablet contains about 1.85% (w/w) water. Optionally, the tablet contains about 1.8% (w/w) water. In some embodiments, the tablet contains about 1.75% (w/w) water. Optionally, the tablet contains about 1.7% (w/w) water. In some embodiments, the tablet contains about 1.65% (w/w) water. Optionally, the tablet contains about 1.6% (w/w) water. In some embodiments, the tablet contains about 1.55% (w/w) water. Optionally, the tablet contains about 1.5% (w/w) water. In some embodiments, the tablet contains about 1.45% (w/w) water. Optionally, the tablet contains about 1.4% (w/w) water. In some embodiments, the tablet contains about 1.35% (w/w) water. Optionally, the tablet contains about 1.3% (w/w) water. In some embodiments, the tablet contains about 1.25% (w/w) water. Optionally, the tablet contains about 1.2% (w/w) water. In some embodiments, the tablet contains about 1.15% (w/w) water. Optionally, the tablet contains about 1.1% (w/w) water. In some embodiments, the tablet contains about 1.05% (w/w) water. Optionally, the tablet contains about 1.0% (w/w) water. In some embodiments, the tablet contains about 0.95% (w/w) water. Optionally, the tablet contains about 0.9% (w/w) water. In some embodiments, the tablet contains about 0.85% (w/w) water. Optionally, the tablet contains about 0.8% (w/w) water. In some embodiments, the tablet contains about 0.75% (w/w) water. Optionally, the tablet contains about 0.7% (w/w) water. In some embodiments, the tablet contains about 0.65% (w/w) water. Optionally, the tablet contains about 0.6% (w/w) water. In some embodiments, the water content of the tablet is determined by Karl Fischer titration, such as Karl Fischer Coulometric Titration Method 1c.

In some embodiments, a tablet of the disclosure, such as a tablet produced by the methods described herein, contains between about 0.8% to about 2.2% (w/w) water. Optionally, the tablet contains between about 0.8% to about 2% (w/w) water. In some embodiments, the tablet produced by the method contains between about 0.8% to about 1.9% (w/w) water. Optionally, the tablet contains between about 0.8% to about 1.8% (w/w) water. In some embodiments, the tablet produced by the method contains between about 0.8% to about 1.7% (w/w) water. Optionally, the tablet contains between about 0.8% to about 1.6% (w/w) water. In some embodiments, the tablet produced by the method contains between about 0.8% to about 1.5% (w/w) water. Optionally, the tablet contains between about 0.8% to about 1.4% (w/w) water. In some embodiments, the tablet produced by the method contains between about 0.8% to about 1.3% (w/w) water. Optionally, the tablet contains between about 0.8% to about 1.2% (w/w) water. In some embodiments, the tablet produced by the method contains between about 0.8% to about 1.1% (w/w) water. Optionally, the tablet contains between about 0.8% to about 1.0% (w/w) water. In some embodiments, the tablet produced by the method contains between about 1.0% to about 2.25% (w/w) water. Optionally, the tablet contains between about 1.0% to about 2.0% (w/w) water. In some embodiments, the tablet produced by the method contains between about 1.0% to about 1.75% (w/w) water. Optionally, the tablet contains between about 1.0% to about 1.5% (w/w) water. In some embodiments, the tablet produced by the method contains between about 1.0% to about 1.25% (w/w) water. Optionally, the tablet contains between about 1.25% to about 2.0% (w/w) water. In some embodiments, the tablet produced by the method contains between about 1.25% to about 1.75% (w/w) water. Optionally, the tablet contains between about 1.25% to about 1.5% (w/w) water. In some embodiments, the tablet produced by the method contains between about 1.5% to about 2.0% (w/w) water. Optionally, the tablet contains between about 1.5% to about 1.75% (w/w) water. In some embodiments, the tablet contains between about 1.75% to about 2.0% (w/w) water.

In some embodiments, the tablet contains no more than 0.5% (w/w) more water than the tablet core prior to the spray coating steps (e.g., spray coating increases water content by less than or no more than 0.5% (w/w), such as less than or no more than 0.3%, 0.25, or 0.2 (w/w)). Optionally, the tablet contains no more or essentially no more water than the tablet core prior to the spray coating steps. In certain embodiments, the tablet contains less water than the tablet core prior to the spray coating steps. In some embodiments, the spray coating steps introduce no more than 0.5% (w/w) water into the tablet core (e.g., spray coating increases water content by less than or no more than 0.5% (w/w), such as less than or no more than 0.3%, 0.25, or 0.2 (w/w)). Optionally, the spray coating steps introduce no or essentially no water into the tablet core. In certain embodiments, the spray coating steps reduce the amount of water in the tablet core.

Methods of Preparing a Room Temperature Stable Tablet

A second aspect of the present disclosure provides a method of preparing a tablet for oral delivery of calcitonin comprising (a) dry blending calcitonin, silicified microcrystalline cellulose, coated citric acid, copovidone, crospovidone, and magnesium stearate; (b) compressing the blended mixture into a tablet core; (c) applying a water-soluble barrier layer in an initial spray at a first spray rate sufficient to add approximately 0.25% (w/w) to the tablet core in about 30 minutes at an average product temperature of at least 45° C.; and (d) applying an enteric coating.

To reduce tablet core moisture content, excipients with low moisture content were sourced. In addition, the manufacturing specification for the water content of the peptide(s) was reduced from <10% to <5%. To further reduce water content, a dry blend direct compression process was developed to manufacture the tablet cores with low water content. The process included a series of steps including low energy milling of the peptide with the excipients that allowed for dry blending of the manufacturing excipients with the peptide which achieved acceptable content uniformity.

In some embodiments, the tablet core contains no more than 2.5% (w/w) water prior to the spray coating steps. In some embodiments, the tablet core contains less than 2.5% (w/w) water prior to the spray coating steps. Optionally, the tablet core contains no more than 2.25% (w/w) water prior to the spray coating steps. Optionally, the tablet core contains no more than 2.20% (w/w) water prior to the spray coating steps. In some embodiments, the tablet core contains no more than 2.15% (w/w) water prior to the spray coating steps. Optionally, the tablet core contains no more than 2.10% (w/w) water prior to the spray coating steps. In some embodiments, the tablet core contains no more than 2.05% (w/w) water prior to the spray coating steps. Optionally, the tablet core contains no more than 2.0% (w/w) water prior to the spray coating steps. In some embodiments, the tablet core contains no more than 1.95% (w/w) water prior to the spray coating steps. Optionally, the tablet core contains no more than 1.9% (w/w) water prior to the spray coating steps. In some embodiments, the tablet core contains no more than 1.85% (w/w) water prior to the spray coating steps. Optionally, the tablet core contains no more than 1.8% (w/w) water prior to the spray coating steps. In some embodiments, the tablet core contains no more than 1.75% (w/w) water prior to the spray coating steps. Optionally, the tablet core contains no more than 1.7% (w/w) water prior to the spray coating steps. In some embodiments, the tablet core contains no more than 1.65% (w/w) water prior to the spray coating steps. Optionally, the tablet core contains no more than 1.6% (w/w) water prior to the spray coating steps. In some embodiments, the tablet core contains no more than 1.55% (w/w) water prior to the spray coating steps. Optionally, the tablet core contains no more than 1.5% (w/w) water prior to the spray coating steps. In some embodiments, the tablet core contains no more than 1.45% (w/w) water prior to the spray coating steps. Optionally, the tablet core contains no more than 1.4% (w/w) water prior to the spray coating steps. In some embodiments, the tablet core contains no more than 1.35% (w/w) water prior to the spray coating steps. Optionally, the tablet core contains no more than 1.3% (w/w) water prior to the spray coating steps. In some embodiments, the tablet core contains no more than 1.25% (w/w) water prior to the spray coating steps. Optionally, the tablet core contains no more than 1.2% (w/w) water prior to the spray coating steps. In some embodiments, the tablet core contains no more than 1.15% (w/w) water prior to the spray coating steps. Optionally, the tablet core contains no more than 1.1%

(w/w) water prior to the spray coating steps. In some embodiments, the tablet core contains no more than 1.05% (w/w) water prior to the spray coating steps. Optionally, the tablet core contains no more than 1.0% (w/w) water prior to the spray coating steps. In some embodiments, the tablet core contains no more than 0.95% (w/w) water prior to the spray coating steps. Optionally, the tablet core contains no more than 0.9% (w/w) water prior to the spray coating steps. In some embodiments, the tablet core contains no more than 0.85% (w/w) water prior to the spray coating steps. Optionally, the tablet core contains no more than 0.8% (w/w) water prior to the spray coating steps. In some embodiments, water content of the tablet core is determined by Karl Fischer titration, such as Karl Fischer Coulometric Titration Method 1c.

In some embodiments, the total acid in the tablet core is in a quantity which, if added to ten milliliters of 0.1 M aqueous sodium bicarbonate solution, would be sufficient to lower the pH of said solution to no higher than 5.5. Optionally, the tablet does not include an amount of base which, if released together with the acid, would prevent the pH of said solution from dropping to 5.5 or below. The acid may be selected from citric acid, tartaric acid and an acid salt of an amino acid. Optionally, the acid is citric acid. In some embodiments, the coating on the acid particles is a pharmaceutically acceptable protective coating that is non-acidic and has a solubility in water of at least one gram per 100 milliliters of water at room temperature. In some embodiments, the protective coating of the coated acid particles is a sugar. Optionally, the sugar is glucose. The sugar may be maltodextrin.

In some embodiments, the calcitonin is selected from the group consisting of human calcitonin, salmon calcitonin, eel calcitonin, elkatonin, porcine calcitonin, and chicken calcitonin. Optionally, the calcitonin is salmon calcitonin. The salmon calcitonin may have the amino acid sequence of CSNLSTCVLGKLSQELHKLQTYPRTNTGSGTP-NH$_2$ (SEQ ID NO: 1), wherein P—NH$_2$ represents an amidated proline. The tablet may comprise about 100 to about 1000 µg salmon calcitonin. The tablet may comprise about 100 to about 500 µg salmon calcitonin. In some embodiments, the tablet comprises about 100 µg salmon calcitonin. Optionally, the tablet comprises about 150 µg salmon calcitonin. In some embodiments, the tablet comprises about 200 µg salmon calcitonin. Optionally, the tablet comprises about 250 µg salmon calcitonin. In some embodiments, the tablet comprises about 300 µg salmon calcitonin. Optionally, the tablet comprises about 350 µg salmon calcitonin. In some embodiments, the tablet comprises about 400 µg salmon calcitonin. Optionally, the tablet comprises about 450 µg salmon calcitonin. In some embodiments, the tablet comprises about 500 µg salmon calcitonin. Preferably, the tablet comprises about 200 µg salmon calcitonin. Optionally, the coated citric acid particles are maltodextrin-coated citric acid particles. In some embodiments, the tablet core comprises (i) about 0.01% (w/w) to about 0.10% (w/w) salmon calcitonin; (ii) about 62% (w/w) maltodextrin-coated citric acid; (iii) about 1.1% (w/w) crospovidone; (iv) about 5% (w/w) copovidone; (v) about 31% (w/w) silicified microcrystalline cellulose; and (vi) about 0.5% (w/w) magnesium stearate. In some embodiments, the tablet core comprises about 0.02% (w/w) salmon calcitonin.

In some embodiments, the tablet may contain one or more additional pharmaceutical excipients. In some embodiments, the one or more additional pharmaceutical excipients are in the tablet core. Non-limiting examples of additional pharmaceutical excipients include absorption enhancers (e.g., solubility enhancers and transport enhancers), fillers, binders, glidants, antioxidants, additional peptides, carriers, diluents, preservatives, and colorants. The use of such excipients is disclosed, infra.

In some embodiments, the water-soluble barrier layer comprises hydroxypropylmethylcellulose, hydroxypropylcellulose, methylcellulose, polyvinylpyrolidone, or a polyvinyl alcohol-polyethylene glycol graft copolymer, such as a polyvinyl alcohol-polyethylene glycol graft copolymer. The enteric coating may be selected from the group consisting of cellulose acetate phthalate, hydroxypropyl methylethylcellulose succinate, hydroxypropyl methylcellulose phthalate, carboxyl methylethylcellulose, methacrylic acid-methyl methacrylate copolymer, and methacrylic acid-ethyl acrylate. Optionally, the enteric coating comprises a methacrylic acid-ethyl acrylate copolymer (1:1).

In some embodiments, the first spray rate is sufficient to add approximately 0.3% (w/w) of the water-soluble barrier layer to the tablet core in about 30 minutes. Optionally, the first spray rate is sufficient to add approximately 0.35% (w/w) of the water-soluble barrier layer to the tablet core in about 30 minutes. The first spray rate may be sufficient to add approximately 0.4% (w/w) of the water-soluble barrier layer to the tablet core in about 30 minutes. In some embodiments, the first spray rate is sufficient to add approximately 0.45% (w/w) of the water-soluble barrier layer to the tablet core in about 30 minutes. Optionally, the first spray rate is sufficient to add approximately 0.5% (w/w) of the water-soluble barrier layer to the tablet core in about 30 minutes.

In some embodiments, the first spray rate is such that no more than 0.5% (w/w) of the water-soluble barrier layer is added to the tablet core in about 30 minutes. Optionally, the first spray rate is such that no more than 0.45% (w/w) of the water-soluble barrier layer is added to the tablet core in about 30 minutes. The first spray rate may be such that no more than 0.4% (w/w) of the water-soluble barrier layer is added to the tablet core in about 30 minutes. In some embodiments, the first spray rate is such that no more than 0.35% (w/w) of the water-soluble barrier layer is added to the tablet core in about 30 minutes. Optionally, the first spray rate is such that no more than 0.3% (w/w) of the water-soluble barrier layer is added to the tablet core in about 30 minutes. The first spray rate may be such that no more than 0.25% (w/w) of the water-soluble barrier layer is added to the tablet core in about 30 minutes.

In some embodiments of any of the above methods, after applying the water-soluble barrier layer at the first spray rate for at least 30 minutes, the water-soluble barrier layer is applied in a subsequent spray at a second spray rate, which is faster than the first spray rate. The water-soluble barrier layer may be applied at the first spray rate for at least 45 minutes before applying the water-soluble barrier layer at the second spray rate. Optionally, the water-soluble barrier layer is applied at the first spray rate for at least 60 minutes before applying the water-soluble barrier layer at the second spray rate. In some embodiments, the water-soluble barrier layer is applied at the first spray rate for at least 75 minutes before applying the water-soluble barrier layer at the second spray rate. Optionally, the water-soluble barrier layer is applied at the first spray rate for at least 90 minutes before applying the water-soluble barrier layer at the second spray rate. In some embodiments, the water-soluble barrier layer is applied at the first spray rate for at least 115 minutes before applying the water-soluble barrier layer at the second spray rate. Optionally, the water-soluble barrier layer is applied at the first spray rate for at least 120 minutes before applying the water-soluble barrier layer at the second spray rate.

In some embodiments, the subsequent spray is performed with the same nozzle as the initial spray. Optionally, the subsequent spray is performed with a different nozzle than the initial spray.

In some embodiments of any of the above methods, the second spray rate is at least 1.4 times faster than the first spray rate. Optionally, the second spray rate is at least 1.5 times faster than the first spray rate. The second spray rate may be at least 1.6 times faster than the first spray rate. In some embodiments of any of the above methods, the second spray rate is at least 1.7 times faster than the first spray rate. Optionally, the second spray rate is at least 1.8 times faster than the first spray rate. The second spray rate may be at least 1.9 times faster than the first spray rate. In some embodiments of any of the above methods, the second spray rate is at least 2.0 times faster than the first spray rate. Optionally, the second spray rate is at least 2.1 times faster than the first spray rate. The second spray rate may be at least 2.2 times faster than the first spray rate. In some embodiments of any of the above methods, the second spray rate is at least 2.3 times faster than the first spray rate. Optionally, the second spray rate is at least 2.4 times faster than the first spray rate. The second spray rate may be at least 2.5 times faster than the first spray rate. In some embodiments of any of the above methods, the second spray rate is at least 2.75 times faster than the first spray rate. Optionally, the second spray rate is at least 3.0 times faster than the first spray rate.

In some embodiments of any of the above methods, the second spray rate is about 1.4 times faster than the first spray rate. Optionally, the second spray rate is about 1.5 times faster than the first spray rate. The second spray rate may be about 1.6 times faster than the first spray rate. In some embodiments of any of the above methods, the second spray rate is about 1.7 times faster than the first spray rate. Optionally, the second spray rate is about 1.8 times faster than the first spray rate. The second spray rate may be about 1.9 times faster than the first spray rate. In some embodiments of any of the above methods, the second spray rate is about 2.0 times faster than the first spray rate. Optionally, the second spray rate is about 2.1 times faster than the first spray rate. The second spray rate may be about 2.2 times faster than the first spray rate. In some embodiments of any of the above methods, the second spray rate is about 2.3 times faster than the first spray rate. Optionally, the second spray rate is about 2.4 times faster than the first spray rate. The second spray rate may be about 2.5 times faster than the first spray rate. In some embodiments of any of the above methods, the second spray rate is about 2.75 times faster than the first spray rate. Optionally, the second spray rate is about 3.0 times faster than the first spray rate.

In some embodiments, the second spray rate is sufficient to add about 5.5% (w/w) of the water-soluble barrier layer to the tablet core in about four and a half hours. Optionally, the second spray rate is sufficient to add about 5.5% (w/w) of the water-soluble barrier layer to the tablet core in about four hours. The second spray rate may be sufficient to add about 5.5% (w/w) of the water-soluble barrier layer to the tablet core in about three and a half hours. In some embodiments, the second spray rate is sufficient to add about 5.5% (w/w) of the water-soluble barrier layer to the tablet core in about three hours. The second spray rate may be sufficient to add about 5.5% (w/w) of the water-soluble barrier layer to the tablet core in about two and a half hours. Optionally, the second spray rate is sufficient to add about 5.5% (w/w) of the water-soluble barrier layer to the tablet core in about two hours. The second spray rate may be sufficient to add about 5.5% (w/w) of the water-soluble barrier layer to the tablet core in about one and a half hours.

In some embodiments, the method comprises applying the water-soluble barrier layer at the first spray rate until about 0.5% (w/w) is added to the tablet core and then applying the water-soluble barrier layer at the second spray rate. Optionally, the method comprises applying the water-soluble barrier layer at the first spray rate until about 0.6% (w/w) is added to the tablet core and then applying the water-soluble barrier layer at the second spray rate. In some embodiments, the method comprises applying the water-soluble barrier layer at the first spray rate until about 0.7% (w/w) is added to the tablet core and then applying the water-soluble barrier layer at the second spray rate. The method may comprise applying the water-soluble barrier layer at the first spray rate until about 0.8% (w/w) is added to the tablet core and then applying the water-soluble barrier layer at the second spray rate. Optionally, the method comprises applying the water-soluble barrier layer at the first spray rate until about 0.9% (w/w) is added to the tablet core and then applying the water-soluble barrier layer at the second spray rate. In some embodiments, the method comprises applying the water-soluble barrier layer at the first spray rate until about 1.0% (w/w) is added to the tablet core and then applying the water-soluble barrier layer at the second spray rate. Optionally, the method comprises applying the water-soluble barrier layer at the first spray rate until about 1.25% (w/w) is added to the tablet core and then applying the water-soluble barrier layer at the second spray rate. In some embodiments, the method comprises applying the water-soluble barrier layer at the first spray rate until about 1.5% (w/w) is added to the tablet core and then applying the water-soluble barrier layer at the second spray rate. Optionally, the method comprises applying the water-soluble barrier layer at the first spray rate until about 1.75% (w/w) is added to the tablet core and then applying the water-soluble barrier layer at the second spray rate. In some embodiments, the method comprises applying the water-soluble barrier layer at the first spray rate until about 2.0% (w/w) is added to the tablet core and then applying the water-soluble barrier layer at the second spray rate.

In some embodiments, the water-soluble barrier layer is applied at the second spray rate until a total of about 3.0% (w/w) is added to the tablet core. Optionally, the water-soluble barrier layer is applied at the second spray rate until a total of about 4.0% (w/w) is added to the tablet core. The water-soluble barrier layer may be applied at the second spray rate until a total of about 5.0% (w/w) is added to the tablet core. In some embodiments, the water-soluble barrier layer is applied at the second spray rate until a total of about 6.0% (w/w) is added to the tablet core. Optionally, the water-soluble barrier layer is applied at the second spray rate until a total of about 7.0% (w/w) is added to the tablet core.

The skilled artisan would recognize that average product temperature is achieved by adjusting the inlet temperature and air flow velocity of the spray coater. It is within the skill in the art to identify the correct inlet temperature and air flow velocity of any given spray coater to achieve the desired average product temperature. In some embodiments of any of the above methods, the average product temperature (i.e., bed temperature) during the initial spray of the water-soluble barrier layer is 50° C.±5° C. Optionally, the average product temperature during the initial spray is at least 46° C. In some embodiments, the average product temperature during the initial spray is at least 47° C. Optionally, the average product temperature during the initial spray is at least 48° C. The average product temperature during the initial spray may be at least 49° C. In some embodiments, the average product temperature during the initial spray is at least 50° C. Optionally, the average product temperature during the initial spray is at least 51° C. In some embodiments, the average product temperature during the initial spray is at least 52° C. Optionally, the average product temperature during the initial spray is at least 53° C. In some embodiments, the average product temperature during the initial spray is at least 54° C.

In some embodiments, the average product temperature (i.e., bed temperature) during the initial spray of the water-soluble barrier layer is about 45° C. Optionally, the average product temperature during the initial spray is about 46° C. In some embodiments, the average product temperature during the initial spray is about 47° C. Optionally, the average product temperature during the initial spray is about 48° C. The average product temperature during the initial spray may be about 49° C. In some embodiments, the average product temperature during the initial spray is about 50° C. Optionally, the average product temperature during the initial spray is about 51° C. In some embodiments, the average product temperature during the initial spray is about 52° C. Optionally, the average product temperature during the initial spray is about 53° C. The average product temperature during the initial spray may be about 54° C. In some embodiments, the average product temperature during the initial spray is about 55° C.

In some embodiments, the average product temperature (i.e., bed temperature) during the initial spray of the water-soluble barrier layer between is about 45° C. and about 55° C. Optionally, the average product temperature during the initial spray is between about 46° C. and about 55° C. The average product temperature during the initial spray may be between about 47° C. and about 55° C. In some embodiments, the average product temperature during the initial spray is between about 48° C. and about 55° C. Optionally, the average product temperature during the initial spray is between about 49° C. and about 55° C. In some embodiments, the average product temperature during the initial spray is between about 50° C. and about 55° C. Optionally, the average product temperature during the initial spray is between about 51° C. and about 55° C. The average product temperature during the initial spray may be between about 52° C. and about 55° C. In some embodiments, the average product temperature during the initial spray is between about 53° C. and about 55° C. In some embodiments, the average product temperature (i.e., bed temperature) during the initial spray between is about 45° C. and about 54° C. Optionally, the average product temperature during the initial spray is between about 45° C. and about 53° C. The average product temperature during the initial spray may be between about 45° C. and about 52° C. In some embodiments, the average product temperature (i.e., bed temperature) during the initial spray between is about 45° C. and about 51° C. Optionally, the average product temperature during the initial spray is between about 45° C. and about 50° C. The average product temperature during the initial spray may be between about 45° C. and about 49° C. In some embodiments, the average product temperature (i.e., bed temperature) during the initial spray between is about 45° C. and about 48° C. Optionally, the average product temperature during the initial spray is between about 45° C. and about 47° C. The average product temperature during the initial spray may be between about 46° C. and about 54° C. In some embodiments, the average product temperature (i.e., bed temperature) during the initial spray between is about 46° C. and about 53° C. Optionally, the average product temperature during the initial spray is between about 47° C. and about 54° C. The average product temperature during the initial spray may be between about 47° C. and about 53° C. In some embodiments, the average product temperature (i.e., bed temperature) during the initial spray between is about 48° C. and about 54° C. Optionally, the average product temperature during the initial spray is between about 48° C. and about 53° C. The average product temperature during the initial spray may be between about 49° C. and about 54° C. In some embodiments, the average product temperature (i.e., bed temperature) during the initial spray between is about 49° C. and about 53° C. Optionally, the average product temperature during the initial spray is between about 50° C. and about 54° C. The average product temperature during the initial spray may be between about 50° C. and about 53° C. In some embodiments, the average product temperature (i.e., bed temperature) during the initial spray between is about 51° C. and about 54° C. Optionally, the average product temperature during the initial spray is between about 51° C. and about 53° C. The average product temperature during the initial spray may be between about 47° C. and about 52° C. In some embodiments, the average product temperature (i.e., bed temperature) during the initial spray between is about 47° C. and about 51° C. Optionally, the average product temperature during the initial spray is between about 47° C. and about 50° C. The average product temperature during the initial spray may be between about 49° C. and about 51° C.

In some embodiments, the minimum product temperature during the initial spray of the water-soluble barrier layer is at least 40° C. Optionally, the minimum product temperature during the initial spray is at least 41° C. The minimum product temperature during the initial spray may be at least 42° C. In some embodiments, the minimum product temperature during the initial spray is at least 43° C. Optionally, the minimum product temperature during the initial spray is at least 44° C. In some embodiments, the minimum product temperature during the initial spray is at least 45° C. Optionally, the minimum product temperature during the initial spray is at least 46° C. In some embodiments, the minimum product temperature during the initial spray is at least 47° C. In some embodiments, the minimum product temperature during the initial spray is at least 48° C. Optionally, the minimum product temperature during the initial spray is at least 49° C.

In some embodiments, the minimum product temperature during the initial spray of the water-soluble barrier layer is about 40° C. Optionally, the minimum product temperature during the initial spray is about 41° C. The minimum product temperature during the initial spray may be about 42° C. In some embodiments, the minimum product temperature during the initial spray is about 43° C. Optionally, the minimum product temperature during the initial spray is about 44° C. In some embodiments, the minimum product temperature during the initial spray is about 45° C. Optionally, the minimum product temperature during the initial spray is about 46° C. In some embodiments, the minimum product temperature during the initial spray is about 47° C. In some embodiments, the minimum product temperature during the initial spray is about 48° C. Optionally, the minimum product temperature during the initial spray is about 49° C.

In some embodiments, the maximum product temperature during the initial spray of the water-soluble barrier layer is at most 50° C. Optionally, the maximum product temperature during the initial spray is at most 49° C. The maximum product temperature during the initial spray may be at most 48° C. In some embodiments, the maximum product temperature during the initial spray is at most 47° C. Optionally, the maximum product temperature during the initial spray is at most 46° C. In some embodiments, the maximum product temperature during the initial spray is at most 45° C. Optionally, the maximum product temperature during the initial spray is at most 44° C. The maximum product temperature during the initial spray may be at most 43° C. In some embodiments, the maximum product temperature during the initial spray is at most 42° C. Optionally, the maximum product temperature during the initial spray is at most 41° C.

In some embodiments, the maximum product temperature during the initial spray of the water-soluble barrier layer is about 50° C. Optionally, the maximum product temperature during the initial spray is about 49° C. The maximum product temperature during the initial spray may be about 48° C. In some embodiments, the maximum product temperature during the initial spray is about 47° C. Optionally, the maximum product temperature during the initial spray is about 46° C. In some embodiments, the maximum product temperature during the initial spray is about 45° C. Optionally, the maximum product temperature during the initial spray is about 44° C. The maximum product temperature during the initial spray may be about 43° C. In some embodiments, the maximum product temperature during the initial spray is about 42° C. Optionally, the maximum product temperature during the initial spray is about 41° C.

In some embodiments of any of the above methods, the average product temperature (i.e., bed temperature) during the subsequent spray of the water-soluble barrier layer is 45° C.±5° C. In some embodiments, the average product temperature (i.e., bed temperature) during the subsequent spray of the water-soluble barrier layer is at least 40° C. In some embodiments, the average product temperature during the subsequent spray is at least 41° C. Optionally, the average product temperature during the subsequent spray is at least 42° C. In some embodiments, the average product temperature during the subsequent spray is at least 43° C. Optionally, the average product temperature during the subsequent spray is at least 44° C. The average product temperature during the subsequent spray may be at least 45° C. In some embodiments, the average product temperature during the subsequent spray is at least 46° C. Optionally, the average product temperature during the subsequent spray is at least 47° C. In some embodiments, the average product temperature during the subsequent spray is at least 48° C. Optionally, the average product temperature during the subsequent spray is at least 49° C. In some embodiments, the average product temperature during the subsequent spray is at least 50° C.

In some embodiments, the average product temperature (i.e., bed temperature) during the subsequent spray of the water-soluble barrier layer is about 40° C. In some embodiments, the average product temperature during the subsequent spray is about 41° C. Optionally, the average product temperature during the subsequent spray is about 42° C. In some embodiments, the average product temperature during the subsequent spray is about 43° C. Optionally, the average product temperature during the subsequent spray is about 44° C. The average product temperature during the subsequent spray may be about 45° C. In some embodiments, the average product temperature during the subsequent spray is about 46° C. Optionally, the average product temperature during the subsequent spray is about 47° C. In some embodiments, the average product temperature during the subsequent spray is about 48° C. The average product temperature during the subsequent spray may be about 49° C. In some embodiments, the average product temperature during the subsequent spray is about 50° C.

In some embodiments, the average product temperature (i.e., bed temperature) during the subsequent spray of the water-soluble barrier layer is between about 40° C. and about 50° C. Optionally, the average product temperature during the subsequent spray is between about 41° C. and about 50° C. The average product temperature during the subsequent spray may be between about 42° C. and about 50° C. In some embodiments, the average product temperature during the subsequent spray is between about 43° C. and about 50° C. Optionally, the average product temperature during the subsequent spray is between about 44° C. and about 50° C. In some embodiments, the average product temperature during the subsequent spray is between about 45° C. and about 50° C. Optionally, the average product temperature during the subsequent spray is between about 46° C. and about 50° C. The average product temperature during the subsequent spray may be between about 47° C. and about 50° C. In some embodiments, the average product temperature during the subsequent spray is between about 48° C. and about 50° C. Optionally, the average product temperature during the subsequent spray is between about 40° C. and about 49° C. The average product temperature during the subsequent spray may be between about 40° C. and about 48° C. In some embodiments, the average product temperature during the subsequent spray is between about 40° C. and about 47° C. Optionally, the average product temperature during the subsequent spray is between about 40° C. and about 46° C. The average product temperature during the subsequent spray may be between about 40° C. and about 45° C. In some embodiments, the average product temperature during the subsequent spray is between about 40° C. and about 44° C. Optionally, the average product temperature during the subsequent spray is between about 40° C. and about 43° C. The average product temperature during the subsequent spray may be between about 40° C. and about 42° C. In some embodiments, the average product temperature during the subsequent spray is between about 41° C. and about 49° C. Optionally, the average product temperature during the subsequent spray is between about 48° C. and about 48° C. The average product temperature during the subsequent spray may be between about 43° C. and about 47° C. In some embodiments, the average product temperature during the subsequent spray is between about 44° C. and about 46° C.

In some embodiments, the minimum product temperature during the subsequent spray of the water-soluble barrier layer is at least 40° C. Optionally, the minimum product temperature during the subsequent spray is at least 41° C. The minimum product temperature during the subsequent spray may be at least 42° C. In some embodiments, the minimum product temperature during the subsequent spray is at least 43° C. Optionally, the minimum product temperature during the subsequent spray is at least 44° C. In some embodiments, the minimum product temperature during the subsequent spray is at least 45° C. Optionally, the minimum product temperature during the subsequent spray is at least 46° C. The minimum product temperature during the subsequent spray may be at least 47° C. In some embodiments, the minimum product temperature during the subsequent spray is at least 48° C. Optionally, the minimum product temperature during the subsequent spray is at least 49° C.

In some embodiments, the minimum product temperature during the subsequent spray of the water-soluble barrier layer is about 40° C. Optionally, the minimum product temperature during the subsequent spray is about 41° C. The minimum product temperature during the subsequent spray may be about 42° C. In some embodiments, the minimum product temperature during the subsequent spray is about 43° C. Optionally, the minimum product temperature during the subsequent spray is about 44° C. In some embodiments, the minimum product temperature during the subsequent spray is about 45° C. Optionally, the minimum product temperature during the subsequent spray is about 46° C. The minimum product temperature during the subsequent spray may be about 47° C. In some embodiments, the minimum product temperature during the subsequent spray is about 48° C. Optionally, the minimum product temperature during the subsequent spray is about 49° C.

In some embodiments, the maximum product temperature during the subsequent spray of the water-soluble barrier layer is at most 43° C. Optionally, the maximum product temperature during the subsequent spray is at most 44° C. In some embodiments, the maximum product temperature during the subsequent spray is at most 45° C. Optionally, the maximum product temperature during the subsequent spray is at most 46° C. The maximum product temperature during the subsequent spray may be at most 47° C. In some embodiments, the maximum product temperature during the subsequent spray is at most 48° C. Optionally, the maximum product temperature during the subsequent spray is at most 49° C. In some embodiments, the maximum product temperature during the subsequent spray is at most 50° C.

In some embodiments, the maximum product temperature during the subsequent spray of the water-soluble barrier layer is about 43° C. Optionally, the maximum product temperature during the subsequent spray is about 44° C. In some embodiments, the maximum product temperature during the subsequent spray is about 45° C. Optionally, the maximum product temperature during the subsequent spray is about 46° C. The maximum product temperature during the subsequent spray may be about 47° C. In some embodiments, the maximum product temperature during the subsequent spray is about 48° C. Optionally, the maximum product temperature during the subsequent spray is about 49° C. In some embodiments, the maximum product temperature during the subsequent spray is about 50° C.

In some embodiments, the enteric coating adds about 4% to the weight of the tablet, including the tablet core and the water-soluble barrier layer. Optionally, the enteric coating adds about 4.5% to the weight of the tablet, including the tablet core and the water-soluble barrier layer. In some embodiments, the enteric coating adds about 5% to the weight of the tablet, including the tablet core and the water-soluble barrier layer. Optionally, the enteric coating adds about 5.5% to the weight of the tablet, including the tablet core and the water-soluble barrier layer. In some embodiments, the enteric coating adds about 6% to the weight of the tablet, including the tablet core and the water-soluble barrier layer. Optionally, the enteric coating adds about 6.5% to the weight of the tablet, including the tablet core and the water-soluble barrier layer. In some embodiments, the enteric coating adds about 7% to the weight of the tablet, including the tablet core and the water-soluble barrier layer. Optionally, the enteric coating adds about 7.5% to the weight of the tablet, including the tablet core and the water-soluble barrier layer. In some embodiments, the enteric coating adds about 8% to the weight of the tablet, including the tablet core and the water-soluble barrier layer.

In some embodiments, the tablet produced by the method contains no more than 2.5% (w/w) water. In some embodiments, the tablet produced by the method contains less than 2.5% (w/w) water. Optionally, the tablet contains no more than 2.25% (w/w) water. Optionally, the tablet contains no more than 2.20% (w/w) water. In some embodiments, the tablet contains no more than 2.15% (w/w) water. Optionally, the tablet contains no more than 2.10% (w/w) water. In some embodiments, the tablet contains no more than 2.05% (w/w) water. Optionally, the tablet contains no more than 2.0% (w/w) water. In some embodiments, the tablet contains no more than 1.95% (w/w) water. Optionally, the tablet contains no more than 1.9% (w/w) water. In some embodiments, the tablet contains no more than 1.85% (w/w) water. Optionally, the tablet contains no more than 1.8% (w/w) water. In some embodiments, the tablet contains no more than 1.75% (w/w) water. Optionally, the tablet contains no more than 1.7% (w/w) water. In some embodiments, the tablet contains no more than 1.65% (w/w) water. Optionally, the tablet contains no more than 1.6% (w/w) water. In some embodiments, the tablet contains no more than 1.55% (w/w) water. Optionally, the tablet contains no more than 1.5% (w/w) water. In some embodiments, the tablet contains no more than 1.45% (w/w) water. Optionally, the tablet contains no more than 1.4% (w/w) water. In some embodiments, the tablet contains no more than 1.35% (w/w) water. Optionally, the tablet contains no more than 1.3% (w/w) water. In some embodiments, the tablet contains no more than 1.25% (w/w) water. Optionally, the tablet contains no more than 1.2% (w/w) water. In some embodiments, the tablet contains no more than 1.15% (w/w) water. Optionally, the tablet contains no more than 1.1% (w/w) water. In some embodiments, the tablet contains no more than 1.05% (w/w) water. Optionally, the tablet contains no more than 1.0% (w/w) water. In some embodiments, the tablet contains no more than 0.95% (w/w) water. Optionally, the tablet contains no more than 0.9% (w/w) water. In some embodiments, the tablet contains no more than 0.85% (w/w) water. Optionally, the tablet contains no more than 0.8% (w/w) water. In some embodiments, the tablet contains no more than 0.75% (w/w) water. Optionally, the tablet contains no more than 0.7% (w/w) water. In some embodiments, the tablet contains no more than 0.65% (w/w) water. Optionally, the tablet contains no more than 0.6% (w/w) water. In some embodiments, water content of the tablet is determined by Karl Fischer titration, such as Karl Fischer Coulometric Titration Method 1c.

In some embodiments, the tablet produced by the method contains about 2.5% (w/w) water. Optionally, the tablet contains about 2.25% (w/w) water. Optionally, the tablet contains about 2.20% (w/w) water. In some embodiments, the tablet contains about 2.15% (w/w) water. Optionally, the tablet contains about 2.10% (w/w) water. In some embodiments, the tablet contains about 2.05% (w/w) water. Optionally, the tablet contains about 2.0% (w/w) water. In some embodiments, the tablet contains about 1.95% (w/w) water. Optionally, the tablet contains about 1.9% (w/w) water. In some embodiments, the tablet contains about 1.85% (w/w) water. Optionally, the tablet contains about 1.8% (w/w) water. In some embodiments, the tablet contains about 1.75% (w/w) water. Optionally, the tablet contains about 1.7% (w/w) water. In some embodiments, the tablet contains about 1.65% (w/w) water. Optionally, the tablet contains about 1.6% (w/w) water. In some embodiments, the tablet contains about 1.55% (w/w) water. Optionally, the tablet contains about 1.5% (w/w) water. In some embodiments, the tablet contains about 1.45% (w/w) water. Optionally, the tablet contains about 1.4% (w/w) water. In some embodiments, the tablet contains about 1.35% (w/w) water. Optionally, the tablet contains about 1.3% (w/w) water. In some embodiments, the tablet contains about 1.25% (w/w) water. Optionally, the tablet contains about 1.2% (w/w) water. In some embodiments, the tablet contains about 1.15% (w/w) water. Optionally, the tablet contains about 1.1% (w/w) water. In some embodiments, the tablet contains about 1.05% (w/w) water. Optionally, the tablet contains about 1.0% (w/w) water. In some embodiments, the tablet contains about 0.95% (w/w) water. Optionally, the tablet contains about 0.9% (w/w) water. In some embodiments, the tablet contains about 0.85% (w/w) water. Optionally, the tablet contains about 0.8% (w/w) water. In some embodiments, the tablet contains about 0.75% (w/w) water. Optionally, the tablet contains about 0.7% (w/w) water. In some embodiments, the tablet contains about 0.65% (w/w) water. Optionally, the tablet contains about 0.6% (w/w) water. In some embodiments, water content of the tablet is determined by Karl Fischer titration, such as Karl Fischer Coulometric Titration Method 1c.

In some embodiments, the tablet produced by the method contains between about 0.8% to about 2.2% (w/w) water. Optionally, the tablet contains between about 0.8% to about 2% (w/w) water. In some embodiments, the tablet produced by the method contains between about 0.8% to about 1.9% (w/w) water. Optionally, the tablet contains between about 0.8% to about 1.8% (w/w) water. In some embodiments, the tablet produced by the method contains between about 0.8% to about 1.7% (w/w) water. Optionally, the tablet contains between about 0.8% to about 1.6% (w/w) water. In some embodiments, the tablet produced by the method contains between about 0.8% to about 1.5% (w/w) water. Optionally, the tablet contains between about 0.8% to about 1.4% (w/w) water. In some embodiments, the tablet produced by the method contains between about 0.8% to about 1.3% (w/w) water. Optionally, the tablet contains between about 0.8% to about 1.2% (w/w) water. In some embodiments, the tablet produced by the method contains between about 0.8% to about 1.1% (w/w) water. Optionally, the tablet contains between about 0.8% to about 1.0% (w/w) water. In some embodiments, the tablet produced by the method contains between about 1.0% to about 2.25% (w/w) water. Optionally, the tablet contains between about 1.0% to about 2.0% (w/w) water. In some embodiments, the tablet produced by the method contains between about 1.0% to about 1.75% (w/w) water. Optionally, the tablet contains between about 1.0% to about 1.5% (w/w) water. In some embodiments, the tablet produced by the method contains between about 1.0% to about 1.25% (w/w) water. Optionally, the tablet contains between about 1.25% to about 2.0% (w/w) water. In some embodiments, the tablet produced by the method contains between about 1.25% to about 1.75% (w/w) water. Optionally, the tablet contains between about 1.25% to about 1.5% (w/w) water. In some embodiments, the tablet produced by the method contains between about 1.5% to about 2.0% (w/w) water. Optionally, the tablet contains between about 1.5% to about 1.75% (w/w) water. In some embodiments, the tablet contains between about 1.75% to about 2.0% (w/w) water. In some embodiments, water content of the tablet is determined by Karl Fischer titration, such as Karl Fischer Coulometric Titration Method 1c.

In some embodiments, the tablet contains no more than 0.5% (w/w) more water than the tablet core prior to the spray coating steps. Optionally, the tablet contains no more water than the tablet core prior to the spray coating steps. In certain embodiments, the tablet contains less water than the tablet core prior to the spray coating steps. In some embodiments, the spray coating steps introduce no more than 0.5% (w/w) water into the tablet core. Optionally, the spray coating steps introduce no water into the tablet core. In certain embodiments, the spray coating steps reduce the amount of water in the tablet core.

Pharmaceutical Compositions

A third aspect of the present disclosure provides a pharmaceutical solid dosage form for oral delivery of calcitonin comprising: (a) a calcitonin intermixed with coated acid particles, wherein the coated acid particles are coated with a pharmaceutically acceptable protective coating, wherein the protective coating separates the organic acid from the calcitonin in the composition; (b) an enteric coating; and (c) a water-soluble barrier layer that separates the tablet core containing the coated acid particles from the enteric coating, wherein the solid dosage form contains no more than 2.5% (w/w) water. In some embodiments, the solid dosage form contains less than 2.5% (w/w) water. Optionally, the solid dosage form is stable at room temperature. In some embodiments, the solid dosage form is room temperature stable for at least 6 months or for at least 9 months or at least 12 months or at least 18 months from the time of packaging.

The solid dosage form may be a capsule or a tablet. In some embodiments, the capsule is a powder-filled capsule. In some embodiments, the capsule is used for over-encapsulation of a tablet core. When the solid dosage form is a capsule, the barrier layer is the capsule body and cap. In some embodiments, the capsule body and cap are coated with an enteric coating. Optionally, the capsule body and cap comprise one or more pharmaceutically approved enteric polymers.

When the solid dosage form is a tablet, the calcitonin intermixed with coated acid particles are present in the tablet core and the tablet core is coated with the water-soluble barrier layer and the enteric coating. Preferably, the barrier layer is a water-soluble barrier layer. The water-soluble barrier layer may be prepared and applied using a non-aqueous solvent, such as isopropyl alcohol or methylene chloride.

In some embodiments, the solid dosage form contains no more than 2.25% (w/w) water. Optionally, the solid dosage form contains no more than 2.20% (w/w) water. In some embodiments, the solid dosage form contains no more than 2.15% (w/w) water. Optionally, the solid dosage form contains no more than 2.10% (w/w) water. In some embodiments, the solid dosage form contains no more than 2.05% (w/w) water. Optionally, the solid dosage form contains no more than 2.0% (w/w) water. In some embodiments, the solid dosage form contains no more than 1.95% (w/w) water. Optionally, the solid dosage form contains no more than 1.9% (w/w) water. In some embodiments, the solid dosage form contains no more than 1.85% (w/w) water. Optionally, the solid dosage form contains no more than 1.8% (w/w) water. In some embodiments, the solid dosage form contains no more than 1.75% (w/w) water. Optionally, the solid dosage form contains no more than 1.7% (w/w) water. In some embodiments, the solid dosage form contains no more than 1.65% (w/w) water. Optionally, the solid dosage form contains no more than 1.6% (w/w) water. In some embodiments, the solid dosage form contains no more than 1.55% (w/w) water. Optionally, the solid dosage form contains no more than 1.5% (w/w) water. In some embodiments, the solid dosage form contains no more than 1.45% (w/w) water. Optionally, the solid dosage form contains no more than 1.4% (w/w) water. In some embodiments, the solid dosage form contains no more than 1.35% (w/w) water. Optionally, the solid dosage form contains no more than 1.3% (w/w) water. In some embodiments, the solid dosage form contains no more than 1.25% (w/w) water. Optionally, the solid dosage form contains no more than 1.2% (w/w) water. In some embodiments, the solid dosage form contains no more than 1.15% (w/w) water. Optionally, the solid dosage form contains no more than 1.1% (w/w) water. In some embodiments, the solid dosage form contains no more than 1.05% (w/w) water. Optionally, the solid dosage form contains no more than 1.0% (w/w) water. In some embodiments, the solid dosage form contains no more than 0.95% (w/w) water. Optionally, the solid dosage form contains no more than 0.9% (w/w) water. In some embodiments, the solid dosage form contains no more than 0.85% (w/w) water. Optionally, the solid dosage form contains no more than 0.8% (w/w) water. In some embodiments, the solid dosage form contains no more than 0.75% (w/w) water. Optionally, the solid dosage form contains no more than 0.7% (w/w) water. In some embodiments, the solid dosage form contains no more than 0.65% (w/w) water. Optionally, the solid dosage form contains no more than 0.6% (w/w) water. In some embodiments, the water content of the tablet is determined by Karl Fischer titration, such as Karl Fischer Coulometric Titration Method 1c.

In some embodiments, the solid dosage form contains about 2.5% (w/w) water. Optionally, the solid dosage form contains about 2.25% (w/w) water. Optionally, the solid dosage form contains about 2.20% (w/w) water. In some embodiments, the solid dosage form contains about 2.15% (w/w) water. Optionally, the solid dosage form contains about 2.10% (w/w) water. In some embodiments, the solid dosage form contains about 2.05% (w/w) water. Optionally, the solid dosage form contains about 2.0% (w/w) water. In some embodiments, the solid dosage form contains about 1.95% (w/w) water. Optionally, the solid dosage form contains about 1.9% (w/w) water. In some embodiments, the solid dosage form contains about 1.85% (w/w) water. Optionally, the solid dosage form contains about 1.8% (w/w) water. In some embodiments, the solid dosage form contains about 1.75% (w/w) water. Optionally, the solid dosage form contains about 1.7% (w/w) water. In some embodiments, the solid dosage form contains about 1.65% (w/w) water. Optionally, the solid dosage form contains about 1.6% (w/w) water. In some embodiments, the solid dosage form contains about 1.55% (w/w) water. Optionally, the solid dosage form contains about 1.5% (w/w) water. In some embodiments, the solid dosage form contains about 1.45% (w/w) water. Optionally, the solid dosage form contains about 1.4% (w/w) water. In some embodiments, the solid dosage form contains about 1.35% (w/w) water. Optionally, the solid dosage form contains about 1.3% (w/w) water. In some embodiments, the solid dosage form contains about 1.25% (w/w) water. Optionally, the solid dosage form contains about 1.2% (w/w) water. In some embodiments, the solid dosage form contains about 1.15% (w/w) water. Optionally, the solid dosage form contains about 1.1% (w/w) water. In some embodiments, the solid dosage form contains about 1.05% (w/w) water. Optionally, the solid dosage form contains about 1.0% (w/w) water. In some embodiments, the solid dosage form contains about 0.95% (w/w) water. Optionally, the solid dosage form contains about 0.9% (w/w) water. In some embodiments, the solid dosage form contains about 0.85% (w/w) water. Optionally, the solid dosage form contains about 0.8% (w/w) water. In some embodiments, the solid dosage form contains about 0.75% (w/w) water. Optionally, the solid dosage form contains about 0.7% (w/w) water. In some embodiments, the solid dosage form contains about 0.65% (w/w) water. Optionally, the solid dosage form contains about 0.6% (w/w) water. In some embodiments, the water content of the solid dosage form is determined by Karl Fischer titration, such as Karl Fischer Coulometric Titration Method 1c.

In some embodiments, the solid dosage form contains between about 0.8% to about 2.2% (w/w) water. Optionally, the solid dosage form contains between about 0.8% to about 2% (w/w) water. In some embodiments, the solid dosage form contains between about 0.8% to about 1.9% (w/w) water. Optionally, the solid dosage form contains between about 0.8% to about 1.8% (w/w) water. In some embodiments, the solid dosage form contains between about 0.8% to about 1.7% (w/w) water. Optionally, the solid dosage form contains between about 0.8% to about 1.6% (w/w) water. In some embodiments, the solid dosage form contains between about 0.8% to about 1.5% (w/w) water. Optionally, the solid dosage form contains between about 0.8% to about 1.4% (w/w) water. In some embodiments, the solid dosage form contains between about 0.8% to about 1.3% (w/w) water. Optionally, the solid dosage form contains between about 0.8% to about 1.2% (w/w) water. In some embodiments, the solid dosage form contains between about 0.8% to about 1.1% (w/w) water. Optionally, the solid dosage form contains between about 0.8% to about 1.0% (w/w) water. In some embodiments, the solid dosage form contains between about 1.0% to about 2.25% (w/w) water. Optionally, the solid dosage form contains between about 1.0% to about 2.0% (w/w) water. In some embodiments, the solid dosage form contains between about 1.0% to about 1.75% (w/w) water. Optionally, the solid dosage form contains between about 1.0% to about 1.5% (w/w) water. In some embodiments, the solid dosage form contains between about 1.0% to about 1.25% (w/w) water. Optionally, the solid dosage form contains between about 1.25% to about 2.0% (w/w) water. In some embodiments, the solid dosage form contains between about 1.25% to about 1.75% (w/w) water. Optionally, the solid dosage form contains between about 1.25% to about 1.5% (w/w) water. In some embodiments, the solid dosage form contains between about 1.5% to about 2.0% (w/w) water. Optionally, the solid dosage form contains between about 1.5% to about 1.75% (w/w) water. In some embodiments, the solid dosage form contains between about 1.75% to about 2.0% (w/w) water. In some embodiments, the water content of the solid dosage form is determined by Karl Fischer titration, such as Karl Fischer Coulometric Titration Method 1c.

The total amount of the coated acid intermixed with the calcitonin should be sufficient, when released into the intestine, to lower the local intestinal pH substantially below the pH optimal for intestinal proteases. In some embodiments, the total acid in the pharmaceutical solid dosage form is in a quantity which, if added to ten milliliters of 0.1 M aqueous sodium bicarbonate solution, would be sufficient to lower the pH of said solution to no higher than 5.5. Optionally, the amount of acid present in the pharmaceutical solid dosage form is sufficient to lower the pH of ten milliliters of 0.1 M aqueous sodium bicarbonate solution to no higher than 4.7, such as no higher than 3.5. In some embodiments, the solid dosage form core comprises about 65% (w/w) coated citric acid. Optionally, the solid dosage form does not include an amount of base which, if released together with the acid, would prevent the pH of said solution from dropping to 5.5 or below. The acid may be selected from citric acid, tartaric acid and an acid salt of an amino acid. Optionally, the acid is citric acid.

In some embodiments, the coated acid is released simultaneously or near-simultaneously with the calcitonin. Quick dissolution of the coating on the coated acid particles may provide sufficient water solubility to permit near-simultaneous release of the acid and the calcitonin. In some embodiments, the coating on the acid particles is a pharmaceutically acceptable protective coating that is non-acidic and has a solubility in water of at least one gram per 100 milliliters of water at room temperature. Optionally, the coating has a solubility in water of at least ten grams per 100 milliliters of water at room temperature. In some embodiments, the protective coating of the coated acid particles is a sugar. Optionally, the sugar is glucose. The sugar may be maltodextrin. In some embodiments, the protective coating is the salt of an acid (e.g., sodium citrate). Optionally, the acid is coated with its corresponding same (e.g., citric acid is coated with a citrate salt, such as sodium citrate). In some embodiments, the average size of the coated acid particles is from 30 mesh to 140 mesh.

In some embodiments, the solid dosage form is a tablet and the tablet core comprises about 55% (w/w) maltodextrin-coated citric acid. Optionally, the tablet core comprises about 56% (w/w) maltodextrin-coated citric acid. In some embodiments, the tablet core comprises about 57% (w/w) maltodextrin-coated citric acid. Optionally, the tablet core comprises about 58% (w/w) maltodextrin-coated citric acid. In some embodiments, the tablet core comprises about 59% (w/w) maltodextrin-coated citric acid. Optionally, the tablet core comprises about 60% (w/w) maltodextrin-coated citric acid. In some embodiments, the tablet core comprises about 61% (w/w) maltodextrin-coated citric acid. Optionally, the tablet core comprises about 62% (w/w) maltodextrin-coated citric acid. In some embodiments, the tablet core comprises about 63% (w/w) maltodextrin-coated citric acid. Optionally, the tablet core comprises about 64% (w/w) maltodextrin-coated citric acid. In some embodiments, the tablet core comprises about 65% (w/w) maltodextrin-coated citric acid. Optionally, the tablet core comprises about 66% (w/w) maltodextrin-coated citric acid.

In some embodiments, the solid dosage form comprises at least about 200 mg maltodextrin-coated citric acid. Optionally, the solid dosage form comprises at least about 250 mg maltodextrin-coated citric acid. In some embodiments, the solid dosage form comprises at least about 300 mg maltodextrin-coated citric acid. Optionally, the solid dosage form comprises at least about 350 mg maltodextrin-coated citric acid. In some embodiments, the solid dosage form comprises at least about 400 mg maltodextrin-coated citric acid. In some embodiments, the solid dosage form comprises at least about 450 mg maltodextrin-coated citric acid. The solid dosage form may comprise about 500 mg maltodextrin-coated citric acid. Optionally, the solid dosage form comprises at least about 550 mg maltodextrin-coated citric acid. In some embodiments, the solid dosage form comprises at least about 600 mg maltodextrin-coated citric acid. Optionally, the solid dosage form comprises between about 200 mg and about 600 mg maltodextrin-coated citric acid.

In some embodiments, the solid dosage form is a tablet and the water-soluble barrier layer comprises an organic based coating.

In some embodiments, the solid dosage form is a tablet and the barrier layer is a water soluble barrier layer. In some embodiments, the water soluble barrier layer is prepared using a non-aqueous (organic) solvent. The non-aqueous solvent may be isopropyl alcohol or methylene chloride. The water soluble barrier coating may be applied using a mixture of water and a non-aqueous solvent, e.g., 70% isopropyl alcohol and 30% water. Optionally, the water soluble barrier layer is soluble in both acidic and basic environments. The barrier layer may have a water solubility of at least one gram per 100 milliliters of water at room temperature. In some embodiments, the barrier layer has a water solubility of at least eleven gram per 100 milliliters of water at room temperature. Optionally, the barrier layer has a water solubility in excess of twelve grams per 100 milliliters of water at room temperature at both pH 6.0 and pH 8.0. The water soluble barrier layer may be non-ionic. In some embodiments, the water-soluble barrier layer comprises hydroxypropylmethylcellulose, hydroxypropylcellulose, methylcellulose, polyvinylpyrolidone, or a polyvinyl alcohol-polyethylene glycol graft copolymer, such as a polyvinyl alcohol-polyethylene glycol graft copolymer. Optionally, the water-soluble barrier layer comprises a polyvinyl alcohol-polyethylene glycol graft copolymer. In some embodiments, the water soluble barrier layer adds at least 3% to the weight of the pharmaceutical tablet, exclusive of the enteric coating. Optionally, the water-soluble barrier layer adds 3-6% to the weight of the pharmaceutical tablet, exclusive of the enteric coating. In some embodiments, the water-soluble barrier layer adds 3% to the weight of the pharmaceutical tablet, exclusive of the enteric coating. Optionally, the water-soluble barrier layer adds 3.5% to the weight of the pharmaceutical tablet, exclusive of the enteric coating. In some embodiments, the water-soluble barrier layer adds 4% to the weight of the pharmaceutical tablet, exclusive of the enteric coating. Optionally, the water-soluble barrier layer adds 4.5% to the weight of the pharmaceutical tablet, exclusive of the enteric coating. In some embodiments, the water-soluble barrier layer adds 5% to the weight of the pharmaceutical tablet, exclusive of the enteric coating. Optionally, the water-soluble barrier layer adds 5.5% to the weight of the pharmaceutical tablet, exclusive of the enteric coating. In some embodiments, the water-soluble barrier layer adds 6% to the weight of the pharmaceutical tablet, exclusive of the enteric coating.

The enteric coating may be any carrier or vehicle that protects the calcitonin from stomach proteases and then dissolves so that the ingredients of the pharmaceutical solid dosage form may be released in the intestine. The enteric coating may be coated on the outside of the pharmaceutical solid dosage form, such as on the outside of the tablet or on the outside of the capsule. In some embodiments, the enteric coating is integrated in the capsule body and cap. In some embodiments, the enteric coating is selected from the group consisting of cellulose acetate phthalate, hydroxypropyl methylethylcellulose succinate, hydroxypropyl methylcellulose phthalate, carboxyl methylethylcellulose, methacrylic acid-methyl methacrylate copolymer, and methacrylic acid-ethyl acrylate. Optionally, the enteric coating comprises a methacrylic acid-ethyl acrylate copolymer (1:1).

In some embodiments, the solid dosage form is a tablet and the enteric coating adds no more than 30% to the weight of the tablet core and water soluble barrier layer. Optionally, the enteric coating adds no more than 20% to the weight of the tablet core and water soluble barrier layer. Optionally, the enteric coating adds 4-8% to the weight of the tablet, including the tablet core and the water-soluble barrier layer. In some embodiments, the enteric coating adds about 4% to the weight of the tablet, including the tablet core and the water-soluble barrier layer. Optionally, the enteric coating adds about 4.5% to the weight of the tablet, including the tablet core and the water-soluble barrier layer. In some embodiments, the enteric coating adds about 5% to the weight of the tablet, including the tablet core and the water-soluble barrier layer. Optionally, the enteric coating adds about 5.5% to the weight of the tablet, including the tablet core and the water-soluble barrier layer. The enteric coating may add 6% to the weight of the tablet, including the tablet core and the water-soluble barrier layer. Optionally, the enteric coating adds 6.5% to the weight of the tablet, including the tablet core and the water-soluble barrier layer. In some embodiments, the enteric coating adds 7% to the weight of the tablet, including the tablet core and the water-soluble barrier layer. The enteric coating may add 7.5% to the weight of the tablet, including the tablet core and the water-soluble barrier layer. Optionally, the enteric coating adds 8% to the weight of the tablet, including the tablet core and the water-soluble barrier layer.

In some embodiments, the calcitonin is selected from the group consisting of human calcitonin, salmon calcitonin, eel calcitonin, elkatonin, porcine calcitonin, and chicken calcitonin. Optionally, the calcitonin is salmon calcitonin. The salmon calcitonin may have the amino acid sequence of CSNLSTCVLGKLSQELHKLQTYPRTNTGSGTP-NH$_2$ (SEQ ID NO: 1), wherein P—NH$_2$ represents an amidated proline. In some embodiments, the solid dosage form comprises about 100 to about 1,000 μg salmon calcitonin. In some embodiments, the solid dosage form comprises about 200 to about 500 μg salmon calcitonin. In some embodiments, the solid dosage form comprises about 100 μg salmon calcitonin. Optionally, the solid dosage form comprises about 150 μg salmon calcitonin. In some embodiments, the solid dosage form comprises about 200 μg salmon calcitonin. Optionally, the solid dosage form comprises about 250 μg salmon calcitonin. In some embodiments, the solid dosage form comprises about 300 μg salmon calcitonin. Optionally, the solid dosage form comprises about 350 μg salmon calcitonin. In some embodiments, the solid dosage form comprises about 400 μg salmon calcitonin. Optionally, the solid dosage form comprises about 450 μg salmon calcitonin. In some embodiments, the solid dosage form comprises about 500 μg salmon calcitonin. In some embodiments, the solid dosage form comprises about 600 μg salmon calcitonin. Optionally, the solid dosage form comprises about 650 μg salmon calcitonin. In some embodiments, the solid dosage form comprises about 700 μg salmon calcitonin. Optionally, the solid dosage form comprises about 750 μg salmon calcitonin. In some embodiments, the solid dosage form comprises about 800 μg salmon calcitonin. Optionally, the solid dosage form comprises about 850 μg salmon calcitonin. In some embodiments, the solid dosage form comprises about 900 μg salmon calcitonin. Optionally, the solid dosage form comprises about 950 μg salmon calcitonin. In some embodiments, the solid dosage form comprises about 1,000 μg salmon calcitonin. Preferably, the solid dosage form comprises about 200 μg salmon calcitonin.

A fourth aspect of the present disclosure provides a pharmaceutical tablet for oral delivery of calcitonin comprising: (a) a tablet core comprising calcitonin intermixed with coated acid particles, wherein the coated acid particles are coated with a pharmaceutically acceptable protective coating, wherein the protective coating separates the organic acid from the calcitonin in the composition; (b) an enteric coating; and (c) a water-soluble barrier layer that separates the tablet core containing the coated acid particles from the enteric coating, wherein the tablet contains no more than 2.5% (w/w) water. In some embodiments, the tablet contains less than 2.5% (w/w) water. Optionally, the tablet is stable at room temperature.

In some embodiments, the tablet contains no more than 2.25% (w/w) water. Optionally, the tablet contains no more than 2.20% (w/w) water. In some embodiments, the tablet contains no more than 2.15% (w/w) water. Optionally, the tablet contains no more than 2.10% (w/w) water. In some embodiments, the tablet contains no more than 2.05% (w/w) water. Optionally, the tablet contains no more than 2.0% (w/w) water. In some embodiments, the tablet contains no more than 1.95% (w/w) water. Optionally, the tablet contains no more than 1.9% (w/w) water. In some embodiments, the tablet contains no more than 1.85% (w/w) water. Optionally, the tablet contains no more than 1.8% (w/w) water. In some embodiments, the tablet contains no more than 1.75% (w/w) water. Optionally, the tablet contains no more than 1.7% (w/w) water. In some embodiments, the tablet contains no more than 1.65% (w/w) water. Optionally, the tablet contains no more than 1.6% (w/w) water. In some embodiments, the tablet contains no more than 1.55% (w/w) water. Optionally, the tablet contains no more than 1.5% (w/w) water. In some embodiments, the tablet contains no more than 1.45% (w/w) water. Optionally, the tablet contains no more than 1.4% (w/w) water. In some embodiments, the tablet contains no more than 1.35% (w/w) water. Optionally, the tablet contains no more than 1.3% (w/w) water. In some embodiments, the tablet contains no more than 1.25% (w/w) water. Optionally, the tablet contains no more than 1.2% (w/w) water. In some embodiments, the tablet contains no more than 1.15% (w/w) water. Optionally, the tablet contains no more than 1.1% (w/w) water. In some embodiments, the tablet contains no more than 1.05% (w/w) water. Optionally, the tablet contains no more than 1.0% (w/w) water. In some embodiments, the tablet contains no more than 0.95% (w/w) water. Optionally, the tablet contains no more than 0.9% (w/w) water. In some embodiments, the tablet contains no more than 0.85% (w/w) water. Optionally, the tablet contains no more than 0.8% (w/w) water. In some embodiments, the tablet contains no more than 0.75% (w/w) water. Optionally, the tablet contains no more than 0.7% (w/w) water. In some embodiments, the tablet contains no more than 0.65% (w/w) water. Optionally, the tablet contains no more than 0.6% (w/w) water. In some embodiments, the water content of the tablet is determined by Karl Fischer titration, such as Karl Fischer Coulometric Titration Method 1c.

In some embodiments, the tablet contains about 2.5% (w/w) water. Optionally, the tablet contains about 2.25% (w/w) water. Optionally, the tablet contains about 2.20% (w/w) water. In some embodiments, the tablet contains about 2.15% (w/w) water. Optionally, the tablet contains about 2.10% (w/w) water. In some embodiments, the tablet contains about 2.05% (w/w) water. Optionally, the tablet contains about 2.0% (w/w) water. In some embodiments, the tablet contains about 1.95% (w/w) water. Optionally, the tablet contains about 1.9% (w/w) water. In some embodiments, the tablet contains about 1.85% (w/w) water. Optionally, the tablet contains about 1.8% (w/w) water. In some embodiments, the tablet contains about 1.75% (w/w) water. Optionally, the tablet contains about 1.7% (w/w) water. In some embodiments, the tablet contains about 1.65% (w/w) water. Optionally, the tablet contains about 1.6% (w/w) water. In some embodiments, the tablet contains about 1.55% (w/w) water. Optionally, the tablet contains about 1.5% (w/w) water. In some embodiments, the tablet contains about 1.45% (w/w) water. Optionally, the tablet contains about 1.4% (w/w) water. In some embodiments, the tablet contains about 1.35% (w/w) water. Optionally, the tablet contains about 1.3% (w/w) water. In some embodiments, the tablet contains about 1.25% (w/w) water. Optionally, the tablet contains about 1.2% (w/w) water. In some embodiments, the tablet contains about 1.15% (w/w) water. Optionally, the tablet contains about 1.1% (w/w) water. In some embodiments, the tablet contains about 1.05% (w/w) water. Optionally, the tablet contains about 1.0% (w/w) water. In some embodiments, the tablet contains about 0.95% (w/w) water. Optionally, the tablet contains about 0.9% (w/w) water. In some embodiments, the tablet contains about 0.85% (w/w) water. Optionally, the tablet contains about 0.8% (w/w) water. In some embodiments, the tablet contains about 0.75% (w/w) water. Optionally, the tablet contains about 0.7% (w/w) water. In some embodiments, the tablet contains about 0.65% (w/w) water. Optionally, the tablet contains about 0.6% (w/w) water. In some embodiments, the water content of the tablet is determined by Karl Fischer titration, such as Karl Fischer Coulometric Titration Method 1c.

In some embodiments, the tablet contains between about 0.8% to about 2.2% (w/w) water. Optionally, the tablet contains between about 0.8% to about 2% (w/w) water. In some embodiments, the tablet contains between about 0.8% to about 1.9% (w/w) water. Optionally, the tablet contains between about 0.8% to about 1.8% (w/w) water. In some embodiments, the tablet contains between about 0.8% to about 1.7% (w/w) water. Optionally, the tablet contains between about 0.8% to about 1.6% (w/w) water. In some embodiments, the tablet contains between about 0.8% to about 1.5% (w/w) water. Optionally, the tablet contains between about 0.8% to about 1.4% (w/w) water. In some embodiments, the tablet contains between about 0.8% to about 1.3% (w/w) water. Optionally, the tablet contains between about 0.8% to about 1.2% (w/w) water. In some embodiments, the tablet contains between about 0.8% to about 1.1% (w/w) water. Optionally, the tablet contains between about 0.8% to about 1.0% (w/w) water. In some embodiments, the tablet contains between about 1.0% to about 2.25% (w/w) water. Optionally, the tablet contains between about 1.0% to about 2.0% (w/w) water. In some embodiments, the tablet contains between about 1.0% to about 1.75% (w/w) water. Optionally, the tablet contains between about 1.0% to about 1.5% (w/w) water. In some embodiments, the tablet contains between about 1.0% to about 1.25% (w/w) water. Optionally, the tablet contains between about 1.25% to about 2.0% (w/w) water. In some embodiments, the tablet contains between about 1.25% to about 1.75% (w/w) water. Optionally, the tablet contains between about 1.25% to about 1.5% (w/w) water. In some embodiments, the tablet contains between about 1.5% to about 2.0% (w/w) water. Optionally, the tablet contains between about 1.5% to about 1.75% (w/w) water. In some embodiments, the tablet contains between about 1.75% to about 2.0% (w/w) water. In some embodiments, the water content of the tablet is determined by Karl Fischer titration, such as Karl Fischer Coulometric Titration Method 1c.

The total amount of the coated acid intermixed with the calcitonin should be sufficient, when released into the intestine, to lower the local intestinal pH substantially below the pH optimal for intestinal proteases. In some embodiments, the total acid in the pharmaceutical tablet is in a quantity which, if added to ten milliliters of 0.1 M aqueous sodium bicarbonate solution, would be sufficient to lower the pH of said solution to no higher than 5.5. Optionally, the amount of acid present in the pharmaceutical tablet is sufficient to lower the pH of ten milliliters of 0.1 M aqueous sodium bicarbonate solution to no higher than 4.7, such as no higher than 3.5. In some embodiments, the tablet core comprises about 65% (w/w) coated citric acid. Optionally, the tablet does not include an amount of base which, if released together with the acid, would prevent the pH of said solution from dropping to 5.5 or below. The acid may be selected from citric acid, tartaric acid and an acid salt of an amino acid. Optionally, the acid is citric acid.

In some embodiments, the coated acid is released simultaneously or near-simultaneously with the calcitonin. Quick dissolution of the coating on the coated acid particles may provide sufficient water solubility to permit near-simultaneous release of the acid and the calcitonin. In some embodiments, the coating on the acid particles is a pharmaceutically acceptable protective coating that is non-acidic and has a solubility in water of at least one gram per 100 milliliters of water at room temperature. Optionally, the coating has a solubility in water of at least ten grams per 100 milliliters of water at room temperature. In some embodiments, the protective coating of the coated acid particles is a sugar. Optionally, the sugar is glucose. The sugar may be maltodextrin. In some embodiments, the protective coating is the salt of an acid (e.g., sodium citrate). Optionally, the acid is coated with its corresponding same (e.g., citric acid is coated with a citrate salt, such as sodium citrate). In some embodiments, the average size of the coated acid particles is from 30 mesh to 140 mesh.

In some embodiments, the tablet core comprises about 55% (w/w) maltodextrin-coated citric acid. Optionally, the tablet core comprises about 56% (w/w) maltodextrin-coated citric acid. In some embodiments, the tablet core comprises about 57% (w/w) maltodextrin-coated citric acid. Optionally, the tablet core comprises about 58% (w/w) maltodextrin-coated citric acid. In some embodiments, the tablet core comprises about 59% (w/w) maltodextrin-coated citric acid. Optionally, the tablet core comprises about 60% (w/w) maltodextrin-coated citric acid. In some embodiments, the tablet core comprises about 61% (w/w) maltodextrin-coated citric acid. Optionally, the tablet core comprises about 62% (w/w) maltodextrin-coated citric acid. In some embodiments, the tablet core comprises about 63% (w/w) maltodextrin-coated citric acid. Optionally, the tablet core comprises about 64% (w/w) maltodextrin-coated citric acid. In some embodiments, the tablet core comprises about 65% (w/w) maltodextrin-coated citric acid. Optionally, the tablet core comprises about 66% (w/w) maltodextrin-coated citric acid.

In some embodiments, the tablet core comprises at least about 200 mg maltodextrin-coated citric acid. Optionally, the tablet core comprises at least about 250 mg maltodextrin-coated citric acid. In some embodiments, the tablet core comprises at least about 300 mg maltodextrin-coated citric acid. Optionally, the tablet core comprises at least about 350 mg maltodextrin-coated citric acid. In some embodiments, the tablet core comprises at least about 400 mg maltodextrin-coated citric acid. In some embodiments, the tablet core comprises at least about 450 mg maltodextrin-coated citric acid. The tablet core may comprise about 500 mg maltodextrin-coated citric acid. Optionally, the tablet core comprises at least about 550 mg maltodextrin-coated citric acid. In some embodiments, the tablet core comprises at least about 600 mg maltodextrin-coated citric acid. Optionally, the tablet core comprises between about 200 mg and about 600 mg maltodextrin-coated citric acid.

In some embodiments, the water-soluble barrier layer comprises an organic based coating.

In some embodiments, the barrier layer is a water soluble barrier layer. In some embodiments, the water soluble barrier layer is prepared using a non-aqueous (organic) solvent. The non-aqueous solvent may be isopropyl alcohol or methylene chloride. The water soluble barrier coating may be applied using a mixture of water and a non-aqueous solvent, e.g., 70% isopropyl alcohol and 30% water. Optionally, the water soluble barrier layer is soluble in both acidic and basic environments. The barrier layer may have a water solubility of at least one gram per 100 milliliters of water at room temperature. In some embodiments, the barrier layer has a water solubility of at least eleven gram per 100 milliliters of water at room temperature. Optionally, the barrier layer has a water solubility in excess of twelve grams per 100 milliliters of water at room temperature at both pH 6.0 and pH 8.0. The water soluble barrier layer may be non-ionic. In some embodiments, the water-soluble barrier layer comprises hydroxypropylmethylcellulose, hydroxypropylcellulose, methylcellulose, polyvinylpyrolidone, or a polyvinyl alcohol-polyethylene glycol graft copolymer, such as a polyvinyl alcohol-polyethylene glycol graft copolymer. Optionally, the water-soluble barrier layer comprises a polyvinyl alcohol-polyethylene glycol graft copolymer. In some embodiments, the water soluble barrier layer adds at least 3% to the weight of the pharmaceutical tablet, exclusive of the enteric coating. Optionally, the water-soluble barrier layer adds 3-6% to the weight of the pharmaceutical tablet, exclusive of the enteric coating. In some embodiments, the water-soluble barrier layer adds 3% to the weight of the pharmaceutical tablet, exclusive of the enteric coating. Optionally, the water-soluble barrier layer adds 3.5% to the weight of the pharmaceutical tablet, exclusive of the enteric coating. In some embodiments, the water-soluble barrier layer adds 4% to the weight of the pharmaceutical tablet, exclusive of the enteric coating. Optionally, the water-soluble barrier layer adds 4.5% to the weight of the pharmaceutical tablet, exclusive of the enteric coating. In some embodiments, the water-soluble barrier layer adds 5% to the weight of the pharmaceutical tablet, exclusive of the enteric coating. Optionally, the water-soluble barrier layer adds 5.5% to the weight of the pharmaceutical tablet, exclusive of the enteric coating. In some embodiments, the water-soluble barrier layer adds 6% to the weight of the pharmaceutical tablet, exclusive of the enteric coating.

The enteric coating may be any carrier or vehicle that protects the calcitonin from stomach proteases and then dissolves so that the ingredients of the pharmaceutical tablet may be released in the intestine. The enteric coating may be coated on the outside of the pharmaceutical tablet. In some embodiments, the enteric coating is selected from the group consisting of cellulose acetate phthalate, hydroxypropyl methylethylcellulose succinate, hydroxypropyl methylcellulose phthalate, carboxyl methylethylcellulose, methacrylic acid-methyl methacrylate copolymer, and methacrylic acid-ethyl acrylate. Optionally, the enteric coating comprises a methacrylic acid-ethyl acrylate copolymer (1:1). In some embodiments, the enteric coating adds no more than 30% to the weight of the tablet core and water soluble barrier layer. Optionally, the enteric coating adds no more than 20% to the weight of the tablet core and water soluble barrier layer. Optionally, the enteric coating adds 4-8% to the weight of the tablet, including the tablet core and the water-soluble barrier layer. In some embodiments, the enteric coating adds about 4% to the weight of the tablet, including the tablet core and the water-soluble barrier layer. Optionally, the enteric coating adds about 4.5% to the weight of the tablet, including the tablet core and the water-soluble barrier layer. In some embodiments, the enteric coating adds about 5% to the weight of the tablet, including the tablet core and the water-soluble barrier layer. Optionally, the enteric coating adds about 5.5% to the weight of the tablet, including the tablet core and the water-soluble barrier layer. The enteric coating may add 6% to the weight of the tablet, including the tablet core and the water-soluble barrier layer. Optionally, the enteric coating adds 6.5% to the weight of the tablet, including the tablet core and the water-soluble barrier layer.

In some embodiments, the enteric coating adds 7% to the weight of the tablet, including the tablet core and the water-soluble barrier layer. The enteric coating may add 7.5% to the weight of the tablet, including the tablet core and the water-soluble barrier layer. Optionally, the enteric coating adds 8% to the weight of the tablet, including the tablet core and the water-soluble barrier layer.

In some embodiments, the calcitonin is selected from the group consisting of human calcitonin, salmon calcitonin, eel calcitonin, elkatonin, porcine calcitonin, and chicken calcitonin. Optionally, the calcitonin is salmon calcitonin. The salmon calcitonin may have the amino acid sequence of CSNLSTCVLGKLSQELHKLQTYPRTNTGSGTP-$NH_2$ (SEQ ID NO: 1), wherein P—$NH_2$ represents an amidated proline. In some embodiments, the tablet comprises about 100 to about 1,000 µg salmon calcitonin. Optionally, the tablet comprises about 200 to about 500 µg salmon calcitonin. In some embodiments, the tablet comprises about 100 µg salmon calcitonin. Optionally, the tablet comprises about 150 µg salmon calcitonin. In some embodiments, the tablet comprises about 200 µg salmon calcitonin. Optionally, the tablet comprises about 250 µg salmon calcitonin. In some embodiments, the tablet comprises about 300 µg salmon calcitonin. Optionally, the tablet comprises about 350 µg salmon calcitonin. In some embodiments, the tablet comprises about 400 µg salmon calcitonin. Optionally, the tablet comprises about 450 µg salmon calcitonin. In some embodiments, the tablet comprises about 500 µg salmon calcitonin. In some embodiments, the tablet comprises about 600 µg salmon calcitonin. Optionally, the tablet comprises about 650 µg salmon calcitonin. In some embodiments, the tablet comprises about 700 µg salmon calcitonin. Optionally, the tablet comprises about 750 µg salmon calcitonin. In some embodiments, the tablet comprises about 800 µg salmon calcitonin. Optionally, the tablet comprises about 850 µg salmon calcitonin. In some embodiments, the tablet comprises about 900 µg salmon calcitonin. Optionally, the tablet comprises about 950 µg salmon calcitonin. In some embodiments, the tablet comprises about 1,000 µg salmon calcitonin. Preferably, the tablet comprises about 200 µg salmon calcitonin.

A fifth aspect of the present disclosure provides a pharmaceutical tablet for oral delivery of calcitonin comprising: (a) a tablet core comprising (i) salmon calcitonin intermixed with maltodextrin-coated citric acid particles, wherein the coated acid particles are coated with a pharmaceutically acceptable protective coating, wherein the protective coating separates the acid from the salmon calcitonin in the composition; (ii) crospovidone; (iii) copovidone; (iv) microcrystalline cellulose; and (v) magnesium stearate; (b) an enteric coating, wherein the enteric coating comprises a methacrylic acid-ethyl acrylate copolymer (1:1); and (c) a water-soluble barrier layer that separates the coated acid particles from the enteric coating, wherein the water-soluble barrier layer comprises a polyvinyl alcohol-polyethylene glycol graft copolymer; wherein the tablet contains no more than 2.5% (w/w) water. In some embodiments, the tablet contains less than 2.5% (w/w) water. Optionally, the tablet is stable at room temperature. In some embodiments, the microcrystalline cellulose is silicified microcrystalline cellulose.

In some embodiments, the tablet comprises about 200 µg salmon calcitonin. Optionally, the tablet core comprises (i) about 0.01% (w/w) to about 0.10% (w/w) salmon calcitonin; (ii) about 62% (w/w) maltodextrin-coated citric acid; (iii) about 1.1% (w/w) crospovidone; (iv) about 5% (w/w) copovidone; (v) about 31% (w/w) microcrystalline cellulose;

and (vi) about 0.5% (w/w) magnesium stearate. In some embodiments, the tablet core comprises about 0.02% (w/w) salmon calcitonin.

In some embodiments, the water-soluble barrier layer adds about 6% to the weight of the tablet core, exclusive of the enteric coating. Optionally, the enteric coating adds about 7% to the weight of the tablet, including the tablet core and the water-soluble barrier layer.

In some embodiments, the tablet contains no more than 2.25% (w/w) water. Optionally, the tablet contains no more than 2.20% (w/w) water. In some embodiments, the tablet contains no more than 2.15% (w/w) water. Optionally, the tablet contains no more than 2.10% (w/w) water. In some embodiments, the tablet contains no more than 2.05% (w/w) water. Optionally, the tablet contains no more than 2.0% (w/w) water. In some embodiments, the tablet contains no more than 1.95% (w/w) water. Optionally, the tablet contains no more than 1.9% (w/w) water. In some embodiments, the tablet contains no more than 1.85% (w/w) water. Optionally, the tablet contains no more than 1.8% (w/w) water. In some embodiments, the tablet contains no more than 1.75% (w/w) water. Optionally, the tablet contains no more than 1.7% (w/w) water. In some embodiments, the tablet contains no more than 1.65% (w/w) water. Optionally, the tablet contains no more than 1.6% (w/w) water. In some embodiments, the tablet contains no more than 1.55% (w/w) water. Optionally, the tablet contains no more than 1.5% (w/w) water. In some embodiments, the tablet contains no more than 1.45% (w/w) water. Optionally, the tablet contains no more than 1.4% (w/w) water. In some embodiments, the tablet contains no more than 1.35% (w/w) water. Optionally, the tablet contains no more than 1.3% (w/w) water. In some embodiments, the tablet contains no more than 1.25% (w/w) water. Optionally, the tablet contains no more than 1.2% (w/w) water. In some embodiments, the tablet contains no more than 1.15% (w/w) water. Optionally, the tablet contains no more than 1.1% (w/w) water. In some embodiments, the tablet contains no more than 1.05% (w/w) water. Optionally, the tablet contains no more than 1.0% (w/w) water. In some embodiments, the tablet contains no more than 0.95% (w/w) water. Optionally, the tablet contains no more than 0.9% (w/w) water. In some embodiments, the tablet contains no more than 0.85% (w/w) water. Optionally, the tablet contains no more than 0.8% (w/w) water. In some embodiments, the tablet contains no more than 0.75% (w/w) water. Optionally, the tablet contains no more than 0.7% (w/w) water. In some embodiments, the tablet contains no more than 0.65% (w/w) water. Optionally, the tablet contains no more than 0.6% (w/w) water. In some embodiments, the water content of the tablet is determined by Karl Fischer titration, such as Karl Fischer Coulometric Titration Method 1c.

In some embodiments, the tablet contains about 2.5% (w/w) water. Optionally, the tablet contains about 2.25% (w/w) water. Optionally, the tablet contains about 2.20% (w/w) water. In some embodiments, the tablet contains about 2.15% (w/w) water. Optionally, the tablet contains about 2.10% (w/w) water. In some embodiments, the tablet contains about 2.05% (w/w) water. Optionally, the tablet contains about 2.0% (w/w) water. In some embodiments, the tablet contains about 1.95% (w/w) water. Optionally, the tablet contains about 1.9% (w/w) water. In some embodiments, the tablet contains about 1.85% (w/w) water. Optionally, the tablet contains about 1.8% (w/w) water. In some embodiments, the tablet contains about 1.75% (w/w) water. Optionally, the tablet contains about 1.7% (w/w) water. In some embodiments, the tablet contains about 1.65% (w/w) water. Optionally, the tablet contains about 1.6% (w/w) water. In some embodiments, the tablet contains about 1.55% (w/w) water. Optionally, the tablet contains about 1.5% (w/w) water. In some embodiments, the tablet contains about 1.45% (w/w) water. Optionally, the tablet contains about 1.4% (w/w) water. In some embodiments, the tablet contains about 1.35% (w/w) water. Optionally, the tablet contains about 1.3% (w/w) water. In some embodiments, the tablet contains about 1.25% (w/w) water. Optionally, the tablet contains about 1.2% (w/w) water. In some embodiments, the tablet contains about 1.15% (w/w) water. Optionally, the tablet contains about 1.1% (w/w) water. In some embodiments, the tablet contains about 1.05% (w/w) water. Optionally, the tablet contains about 1.0% (w/w) water. In some embodiments, the tablet contains about 0.95% (w/w) water. Optionally, the tablet contains about 0.9% (w/w) water. In some embodiments, the tablet contains about 0.85% (w/w) water. Optionally, the tablet contains about 0.8% (w/w) water. In some embodiments, the tablet contains about 0.75% (w/w) water. Optionally, the tablet contains about 0.7% (w/w) water. In some embodiments, the tablet contains about 0.65% (w/w) water. Optionally, the tablet contains about 0.6% (w/w) water. In some embodiments, the water content of the tablet is determined by Karl Fischer titration, such as Karl Fischer Coulometric Titration Method 1c.

In some embodiments, the tablet contains between about 0.8% to about 2.2% (w/w) water. Optionally, the tablet contains between about 0.8% to about 2% (w/w) water. In some embodiments, the tablet contains between about 0.8% to about 1.9% (w/w) water. Optionally, the tablet contains between about 0.8% to about 1.8% (w/w) water. In some embodiments, the tablet contains between about 0.8% to about 1.7% (w/w) water. Optionally, the tablet contains between about 0.8% to about 1.6% (w/w) water. In some embodiments, the tablet contains between about 0.8% to about 1.5% (w/w) water. Optionally, the tablet contains between about 0.8% to about 1.4% (w/w) water. In some embodiments, the tablet contains between about 0.8% to about 1.3% (w/w) water. Optionally, the tablet contains between about 0.8% to about 1.2% (w/w) water. In some embodiments, the tablet contains between about 0.8% to about 1.1% (w/w) water. Optionally, the tablet contains between about 0.8% to about 1.0% (w/w) water. In some embodiments, the tablet contains between about 1.0% to about 2.25% (w/w) water. Optionally, the tablet contains between about 1.0% to about 2.0% (w/w) water. In some embodiments, the tablet contains between about 1.0% to about 1.75% (w/w) water. Optionally, the tablet contains between about 1.0% to about 1.5% (w/w) water. In some embodiments, the tablet contains between about 1.0% to about 1.25% (w/w) water. Optionally, the tablet contains between about 1.25% to about 2.0% (w/w) water. In some embodiments, the tablet contains between about 1.25% to about 1.75% (w/w) water. Optionally, the tablet contains between about 1.25% to about 1.5% (w/w) water. In some embodiments, the tablet contains between about 1.5% to about 2.0% (w/w) water. Optionally, the tablet contains between about 1.5% to about 1.75% (w/w) water. In some embodiments, the tablet contains between about 1.75% to about 2.0% (w/w) water. In some embodiments, water content of the tablet is determined by Karl Fischer titration, such as Karl Fischer Coulometric Titration Method 1c.

In some embodiments, the tablet is made by any of the methods disclosed herein. In certain embodiments, the tablet is room temperature stable.

A sixth aspect of the present disclosure provides a pharmaceutical capsule for oral delivery of calcitonin comprising: (a) a powder fill comprising calcitonin intermixed with coated acid particles, wherein the coated acid particles are coated with a pharmaceutically acceptable protective coating, wherein the protective coating separates the organic acid from the calcitonin in the composition; (b) an enteric coating; and (c) a capsule body and cap that separate the powder fill containing the coated acid particles from the enteric coating, wherein the powder fill contains no more than 2.5% (w/w) water. In some embodiments, the powder fill contains less than 2.5% (w/w) water. Optionally, the capsule is stable at room temperature.

In some embodiments, the powder fill contains no more than 2.25% (w/w) water. Optionally, the powder fill contains no more than 2.20% (w/w) water. In some embodiments, the powder fill contains no more than 2.15% (w/w) water. Optionally, the powder fill contains no more than 2.10% (w/w) water. In some embodiments, the powder fill contains no more than 2.05% (w/w) water. Optionally, the powder fill contains no more than 2.0% (w/w) water. In some embodiments, the powder fill contains no more than 1.95% (w/w) water. Optionally, the powder fill contains no more than 1.9% (w/w) water. In some embodiments, the powder fill contains no more than 1.85% (w/w) water. Optionally, the powder fill contains no more than 1.8% (w/w) water. In some embodiments, the powder fill contains no more than 1.75% (w/w) water. Optionally, the powder fill contains no more than 1.7% (w/w) water. In some embodiments, the powder fill contains no more than 1.65% (w/w) water. Optionally, the powder fill contains no more than 1.6% (w/w) water. In some embodiments, the powder fill contains no more than 1.55% (w/w) water. Optionally, the powder fill contains no more than 1.5% (w/w) water. In some embodiments, the powder fill contains no more than 1.45% (w/w) water. Optionally, the powder fill contains no more than 1.4% (w/w) water. In some embodiments, the powder fill contains no more than 1.35% (w/w) water. Optionally, the powder fill contains no more than 1.3% (w/w) water. In some embodiments, the powder fill contains no more than 1.25% (w/w) water. Optionally, the powder fill contains no more than 1.2% (w/w) water. In some embodiments, the powder fill contains no more than 1.15% (w/w) water. Optionally, the powder fill contains no more than 1.1% (w/w) water. In some embodiments, the powder fill contains no more than 1.05% (w/w) water. Optionally, the powder fill contains no more than 1.0% (w/w) water. In some embodiments, the powder fill contains no more than 0.95% (w/w) water. Optionally, the powder fill contains no more than 0.9% (w/w) water. In some embodiments, the powder fill contains no more than 0.85% (w/w) water. Optionally, the powder fill contains no more than 0.8% (w/w) water. In some embodiments, the powder fill contains no more than 0.75% (w/w) water. Optionally, the powder fill contains no more than 0.7% (w/w) water. In some embodiments, the powder fill contains no more than 0.65% (w/w) water. Optionally, the powder fill contains no more than 0.6% (w/w) water. In some embodiments, the water content of the powder fill is determined by Karl Fischer titration, such as Karl Fischer Coulometric Titration Method 1c.

In some embodiments, the powder fill contains about 2.5% (w/w) water. Optionally, the powder fill contains about 2.25% (w/w) water. Optionally, the powder fill contains about 2.20% (w/w) water. In some embodiments, the powder fill contains about 2.15% (w/w) water. Optionally, the powder fill contains about 2.10% (w/w) water. In some embodiments, the powder fill contains about 2.05% (w/w) water. Optionally, the powder fill contains about 2.0% (w/w) water. In some embodiments, the powder fill contains about 1.95% (w/w) water. Optionally, the powder fill contains about 1.9% (w/w) water. In some embodiments, the powder fill contains about 1.85% (w/w) water. Optionally, the powder fill contains about 1.8% (w/w) water. In some embodiments, the powder fill contains about 1.75% (w/w) water. Optionally, the powder fill contains about 1.7% (w/w) water. In some embodiments, the powder fill contains about 1.65% (w/w) water. Optionally, the powder fill contains about 1.6% (w/w) water. In some embodiments, the powder fill contains about 1.55% (w/w) water. Optionally, the powder fill contains about 1.5% (w/w) water. In some embodiments, the tablet contains about 1.45% (w/w) water. Optionally, the powder fill contains about 1.4% (w/w) water. In some embodiments, the powder fill contains about 1.35% (w/w) water. Optionally, the powder fill contains about 1.3% (w/w) water. In some embodiments, the powder fill contains about 1.25% (w/w) water. Optionally, the powder fill contains about 1.2% (w/w) water. In some embodiments, the powder fill contains about 1.15% (w/w) water. Optionally, the powder fill contains about 1.1% (w/w) water. In some embodiments, the powder fill contains about 1.05% (w/w) water. Optionally, the powder fill contains about 1.0% (w/w) water. In some embodiments, the powder fill contains about 0.95% (w/w) water. Optionally, the powder fill contains about 0.9% (w/w) water. In some embodiments, the powder fill contains about 0.85% (w/w) water. Optionally, the powder fill contains about 0.8% (w/w) water. In some embodiments, the powder fill contains about 0.75% (w/w) water. Optionally, the powder fill contains about 0.7% (w/w) water. In some embodiments, the powder fill contains about 0.65% (w/w) water. Optionally, the powder fill contains about 0.6% (w/w) water. In some embodiments, the water content of the powder fill is determined by Karl Fischer titration, such as Karl Fischer Coulometric Titration Method 1c.

In some embodiments, the powder fill contains between about 0.8% to about 2.2% (w/w) water. Optionally, the powder fill contains between about 0.8% to about 2% (w/w) water. In some embodiments, the powder fill contains between about 0.8% to about 1.9% (w/w) water. Optionally, the powder fill contains between about 0.8% to about 1.8% (w/w) water. In some embodiments, the powder fill contains between about 0.8% to about 1.7% (w/w) water. Optionally, the powder fill contains between about 0.8% to about 1.6% (w/w) water. In some embodiments, the powder fill contains between about 0.8% to about 1.5% (w/w) water. Optionally, the powder fill contains between about 0.8% to about 1.4% (w/w) water. In some embodiments, the powder fill contains between about 0.8% to about 1.3% (w/w) water. Optionally, the powder fill contains between about 0.8% to about 1.2% (w/w) water. In some embodiments, the powder fill contains between about 0.8% to about 1.1% (w/w) water. Optionally, the powder fill contains between about 0.8% to about 1.0% (w/w) water. In some embodiments, the powder fill contains between about 1.0% to about 2.25% (w/w) water. Optionally, the powder fill contains between about 1.0% to about 2.0% (w/w) water. In some embodiments, the powder fill contains between about 1.0% to about 1.75% (w/w) water. Optionally, the powder fill contains between about 1.0% to about 1.5% (w/w) water. In some embodiments, the powder fill contains between about 1.0% to about 1.25% (w/w) water. Optionally, the powder fill contains between about 1.25% to about 2.0% (w/w) water. In some embodiments, the powder fill contains between about 1.25% to about 1.75% (w/w) water. Optionally, the powder fill contains between about 1.25% to about 1.5% (w/w) water. In some embodiments, the powder fill contains between about 1.5% to about 2.0% (w/w) water. Optionally, the powder fill contains between about 1.5% to about 1.75% (w/w) water. In some embodiments, the powder fill contains between about 1.75% to about 2.0% (w/w) water. In some embodiments, the water content of the powder fill is determined by Karl Fischer titration, such as Karl Fischer Coulometric Titration Method 1c.

The total amount of the coated acid intermixed with the calcitonin should be sufficient, when released into the intestine, to lower the local intestinal pH substantially below the pH optimal for intestinal proteases. In some embodiments, the total acid in the pharmaceutical capsule is in a quantity which, if added to ten milliliters of 0.1 M aqueous sodium bicarbonate solution, would be sufficient to lower the pH of said solution to no higher than 5.5. Optionally, the amount of acid present in the pharmaceutical capsule is sufficient to lower the pH of ten milliliters of 0.1 M aqueous sodium bicarbonate solution to no higher than 4.7, such as no higher than 3.5. In some embodiments, the powder fill comprises about 65% (w/w) coated citric acid. Optionally, the capsule does not include an amount of base which, if released together with the acid, would prevent the pH of said solution from dropping to 5.5 or below. The acid may be selected from citric acid, tartaric acid and an acid salt of an amino acid. Optionally, the acid is citric acid.

In some embodiments, the coated acid is released simultaneously or near-simultaneously with the calcitonin. Quick dissolution of the coating on the coated acid particles may provide sufficient water solubility to permit near-simultaneous release of the acid and the calcitonin. In some embodiments, the coating on the acid particles is a pharmaceutically acceptable protective coating that is non-acidic and has a solubility in water of at least one gram per 100 milliliters of water at room temperature. Optionally, the coating has a solubility in water of at least ten grams per 100 milliliters of water at room temperature. In some embodiments, the protective coating of the coated acid particles is a sugar. Optionally, the sugar is glucose. The sugar may be maltodextrin. In some embodiments, the protective coating is the salt of an acid (e.g., sodium citrate). Optionally, the acid is coated with its corresponding same (e.g., citric acid is coated with a citrate salt, such as sodium citrate). In some embodiments, the average size of the coated acid particles is from 30 mesh to 140 mesh.

In some embodiments, the powder fill comprises about 55% (w/w) maltodextrin-coated citric acid. Optionally, the powder fill comprises about 56% (w/w) maltodextrin-coated citric acid. In some embodiments, the powder fill comprises about 57% (w/w) maltodextrin-coated citric acid. Optionally, the powder fill comprises about 58% (w/w) maltodextrin-coated citric acid. In some embodiments, the powder fill comprises about 59% (w/w) maltodextrin-coated citric acid. Optionally, the powder fill comprises about 60% (w/w) maltodextrin-coated citric acid. In some embodiments, the powder fill comprises about 61% (w/w) maltodextrin-coated citric acid. Optionally, the powder fill comprises about 62% (w/w) maltodextrin-coated citric acid. In some embodiments, the powder fill comprises about 63% (w/w) maltodextrin-coated citric acid. Optionally, the powder fill comprises about 64% (w/w) maltodextrin-coated citric acid. In some embodiments, the powder fill comprises about 65% (w/w) maltodextrin-coated citric acid. Optionally, the powder fill comprises about 66% (w/w) maltodextrin-coated citric acid.

In some embodiments, the powder fill comprises at least about 200 mg maltodextrin-coated citric acid. Optionally, the powder fill comprises at least about 250 mg maltodextrin-coated citric acid. In some embodiments, the powder fill comprises at least about 300 mg maltodextrin-coated citric acid. Optionally, the powder fill comprises at least about 350 mg maltodextrin-coated citric acid. In some embodiments, the powder fill comprises at least about 400 mg maltodextrin-coated citric acid. In some embodiments, the powder fill comprises at least about 450 mg maltodextrin-coated citric acid. The powder fill may comprise about 500 mg maltodextrin-coated citric acid. Optionally, the powder fill comprises at least about 550 mg maltodextrin-coated citric acid. In some embodiments, the powder fill comprises at least about 600 mg maltodextrin-coated citric acid. Optionally, the powder fill comprises between about 200 mg and about 600 mg maltodextrin-coated citric acid.

The enteric coating may be any carrier or vehicle that protects the calcitonin from stomach proteases and then dissolves so that the ingredients of the pharmaceutical tablet may be released in the intestine. The enteric coating may be coated on the outside of the capsule body and cap. Optionally, the enteric coating is intrinsic to the capsule body and cap. Such intrinsically enteric capsules are known in the art, e.g., the enTRinsic™ drug delivery technology by CAPSUGEL®. In some embodiments, the enteric coating is selected from the group consisting of cellulose acetate phthalate, hydroxypropyl methylethylcellulose succinate, hydroxypropyl methylcellulose phthalate, carboxyl methylethylcellulose, methacrylic acid-methyl methacrylate copolymer, and methacrylic acid-ethyl acrylate. Optionally, the enteric coating comprises a methacrylic acid-ethyl acrylate copolymer (1:1). In some embodiments, the enteric coating adds no more than 30% to the weight of the powder-filled capsule. Optionally, the enteric coating adds no more than 20% to the weight of the powder-filled capsule. Optionally, the enteric coating adds 4-8% to the weight of the powder-filled capsule. In some embodiments, the enteric coating adds about 4% to the weight of the powder-filled capsule. Optionally, the enteric coating adds about 4.5% to the weight of the powder-filed capsule. In some embodiments, the enteric coating adds about 5% to the weight of the powder-filed capsule. Optionally, the enteric coating adds about 5.5% to the weight of the powder-filed capsule. The enteric coating may add 6% to the weight of the powder-filled capsule. Optionally, the enteric coating adds 6.5% to the weight of the powder-filed capsule. In some embodiments, the enteric coating adds 7% to the weight of the powder-filed capsule. The enteric coating may add 7.5% to the weight of the powder-filled capsule. Optionally, the enteric coating adds 8% to the weight of the powder-filled capsule.

In some embodiments, the calcitonin is selected from the group consisting of human calcitonin, salmon calcitonin, eel calcitonin, elkatonin, porcine calcitonin, and chicken calcitonin. Optionally, the calcitonin is salmon calcitonin. The salmon calcitonin may have the amino acid sequence of CSNLSTCVLGKLSQELHKLQTYPRTNTGSGTP-NH$_2$ (SEQ ID NO: 1), wherein P—NH$_2$ represents an amidated proline. In some embodiments, the capsule comprises about 100 to about 1,000 µg salmon calcitonin. Optionally, the capsule comprises about 200 to about 500 µg salmon calcitonin. In some embodiments, the capsule comprises about 100 µg salmon calcitonin. Optionally, the capsule comprises about 150 µg salmon calcitonin. In some embodiments, the capsule comprises about 200 µg salmon calcitonin. Optionally, the capsule comprises about 250 µg salmon calcitonin. In some embodiments, the capsule comprises about 300 µg salmon calcitonin. Optionally, the capsule comprises about 350 µg salmon calcitonin. In some embodiments, the capsule comprises about 400 µg salmon calcitonin. Optionally, the capsule comprises about 450 µg salmon calcitonin. In some embodiments, the capsule comprises about 500 µg salmon calcitonin. In some embodiments, the capsule comprises about 600 µg salmon calcitonin. Optionally, the capsule comprises about 650 µg salmon calcitonin. In some embodiments, the capsule comprises about 700 µg salmon calcitonin. Optionally, the capsule comprises about 750 µg salmon calcitonin. In some embodiments, the capsule comprises about 800 µg salmon calcitonin. Optionally, the capsule comprises about 850 µg salmon calcitonin. In some embodiments, the capsule comprises about 900 µg salmon calcitonin. Optionally, the capsule comprises about 950 µg salmon calcitonin. In some embodiments, the capsule comprises about 1,000 µg salmon calcitonin. Preferably, the capsule comprises about 200 µg salmon calcitonin.

In some embodiments, the solid dosage form, tablet or capsule may contain one or more additional pharmaceutical excipients. In some embodiments, the one or more additional pharmaceutical excipients are in the tablet core. Optionally, the one or more additional pharmaceutical excipients are in a powder fill of the capsule. The use of such excipients in oral dosage forms of active peptides is known in the art (see, e.g., U.S. Pat. No. 8,377,863, incorporated by reference herein in its entirety). Non-limiting examples of additional pharmaceutical excipients include absorption enhancers (e.g., solubility enhancers and transport enhancers), fillers, binders, glidants, antioxidants, additional peptides, carriers, diluents, preservatives, and colorants.

The pharmaceutical solid dosage form, tablet or capsule may comprise a pharmaceutically acceptable absorption enhancer. In some embodiments, the absorption enhancer is a surface active agent, which acts as both a solubility enhancer and an uptake enhancer. A solubility enhancer improves the ability of the solid dosage form, tablet or capsule components to be solubilized in either the aqueous environment into which they are originally released, into the lipophilic environment of the mucous layer lining the intestinal walls, or both. Transport enhancers (i.e., uptake enhancers) are those which facilitate the ease by which peptide agents cross the intestinal wall. Any suitable absorption enhancer may be used. In some embodiments, the absorption enhancer is a surface active agent selected from the group consisting of (i) anionic surface active agents that are cholesterol derivatives (e.g., bile acids), (ii) cationic surface agents (e.g., acyl carnitines, phospholipids and the like), (iii) non-ionic surface active agents, and (iv) mixtures of anionic surface active agents (especially those having linear hydrocarbon regions) together with negative charge neutralizers. Negative charge neutralizers include but are not limited to acyl carnitines, cetyl pyridinium chloride, and the like. Optionally, the absorption enhancer is soluble at acid pH, e.g., in the 3.0 to 5.0 range. In some embodiments, the absorption enhancer is a mixture of cationic surface active agents and anionic surface active agents that are cholesterol derivatives, both of which are soluble at acid pH. In some embodiments, the absorption enhancer is selected from the group consisting of (a) salicylates such as sodium salicylate, 3-methoxysalicylate, 5-methoxysalicylate and homovanilate; (b) bile acids such as taurocholic, tauorodeoxycholic, deoxycholic, cholic, glycholic, lithocholate, chenodeoxycholic, ursodeoxycholic, ursocholic, dehydrocholic, fusidic, etc.; (c) non-ionic surfactants such as polyoxyethylene ethers (e.g. Brij 36T, Brij 52, Brij 56, Brij 76, Brij 96, Texaphor A6, Texaphor A14, Texaphor A60 etc.), p-t-octyl phenol polyoxyethylenes (Triton X-45, Triton X-100, Triton X-114, Triton X-305 etc.) nonylphenoxypoloxyethylenes (e.g. Igepal CO series), polyoxyethylene sorbitan esters (e.g. Tween-20, Tween-80 etc.); (d) anionic surfactants such as dioctyl sodium sulfosuccinate; (e) lyso-phospholipids such as lysolecithin and lysophosphatidylethanolamine; (f) acylcarnitines, acylcholines and acyl amino acids such as lauroylcarnitine, myristoylcarnitine, palmitoylcarnitine, lauroylcholine, myristoylcholine, palmitoylcholine, hexadecyllysine, N-acylphenylalanine, N-acylglycine etc.; g) water soluble phospholipids such as diheptanoylphosphatidylcholine, dioctylphosphatidylcholine etc.; (h) medium-chain glycerides which are mixtures of mono-, di- and triglycerides containing medium-chain-length fatty acids (caprylic, capric and lauric acids); (i) ethylene-diaminetetraacetic acid; (j) cationic surfactants such as cetylpyridinium chloride; (k) fatty acid derivatives of polyethylene glycol such as Labrasol, Labrafac, etc.; and (l) alkylsaccharides such as lauryl maltoside, lauroyl sucrose, myristoyl sucrose, palmitoyl sucrose, etc. In some embodiments, the absorption enhancer is L-lauroyl carnitine.

The pharmaceutical solid dosage form, tablet or capsule may comprise a pharmaceutically acceptable filler. Any suitable filler may be used. In some embodiments, the filler is a cellulose filler, such as microcrystalline cellulose.

The pharmaceutical solid dosage form, tablet or capsule may comprise a pharmaceutical binder, e.g., for dry compression. The binder may be used to ensure uniform dispersion of the components within the tablet core or powder fill. Such thorough intermixing may improve the simultaneous release of the components of the tablet core, such as the calcitonin and the coated acid particles. Any suitable binder may be used. In some embodiments, the binder is selected from the group consisting of copovidone (e.g. KOLLIDON VA64 (BASF) or KOLLIDON VA64 fine (BASF)), povidone (KOLLIDON 30 (BASF)), microcrystalline cellulose (e.g. AVICEL PH-101 (FMC BIOPOLYMER)), hydroxypropyl methylcellulose (e.g., PHARMACOAT 606 (SHIN-ETSU)), and maltodextrin (e.g., MALDEX (AMYLUM)).

The pharmaceutical solid dosage form, tablet or capsule may comprise a pharmaceutically acceptable disintegrant. The disintegrant may enhance the dissolution speed of the tablet core or powder fill of the capsule. Any suitable disintegrant may be used. In some embodiments, the disintegrant is selected from the group consisting of crospovidone (e.g., POLYPLASDONE (INTERNATIONAL SPECIALTY PRODUCTS)), sodium starch glyoclate (e.g., EXPLOTAB (JRS PHARMA)), and croscarmellose sodium (e.g., AC-DI-SOL (FMC BIOPOLYMER), such as crospovidone. Optionally, the disintegrant comprises between about 1 and 15% (w/w) of the tablet core or powder fill.

The pharmaceutical solid dosage form, tablet or capsule may comprise a pharmaceutically acceptable glidant. The glidant may enhance powder flow. Any suitable glidant may be used. In some embodiments, the glidant the glidant is selected from the group consisting of talc, calcium silicate, magnesium silicate, and silicon dioxide, such as talc. Optionally, the glidant is present in an amount between about 0.1 and 2.0% (w/w) of the tablet core or powder fill.

The pharmaceutical solid dosage form, tablet or capsule may comprise a pharmaceutically acceptable lubricant. The lubricant may prevent the powdered components of the solid dosage form, tablet or capsule from sticking to the tooling may be used. Any suitable lubricant may be used. In some embodiments, the lubricant is selected from the group consisting of stearic acid, magnesium stearate, and hydrogenated vegetable oil type 1, such as magnesium stearate. Optionally, the lubricant is present in an amount between about 0.5 and 5.0% (w/w) of the tablet core or powder fill of the capsule.

The pharmaceutical solid dosage form, tablet or capsule may comprise an additional peptide to reduce non-specific adsorption (e.g., binding of the peptide to the intestinal mucus barrier). Optionally, the additional peptide is not physiologically active and may act as a protease scavenger to reduce the interaction between intestinal proteases and calcitonin. The additional peptide may be a food peptide. In some embodiments, the additional peptide is albumin, casein, soy protein, an animal protein or a vegetable protein. Optionally, the additional peptide is present in an amount between about 1.0 and 10.0% (w/w) of the tablet core or powder fill of the capsule.

The pharmaceutical solid dosage form, tablet or capsule may comprise common pharmaceutical carriers, diluents, fillers, preservatives, colorants and the like in their usual known sizes and amounts. In some embodiments, the maximum weight loss during friability testing of the tablet is no greater than 1%. As used herein, friability testing refers to the technique described in "Tablet Friability", Chapter 1216, USP 28 page 2745, incorporated by reference herein.

An additional aspect of the present disclosure provides a plurality of batches of any of pharmaceutical solid dosage forms, tablets or capsules disclosed above, wherein each of the batches comprises solid dosage forms, tablets or capsules containing no more than 2.25% (w/w) water. Optionally, each of the batches comprises solid dosage forms, tablets or capsules containing no more than 2.20% (w/w) water. In some embodiments, each of the batches comprises solid dosage forms, tablets or capsules containing no more than 2.15% (w/w) water. Optionally, each of the batches comprises solid dosage forms, tablets or capsules containing no more than 2.10% (w/w) water. In some embodiments, each of the batches comprises solid dosage forms, tablets or capsules containing no more than 2.05% (w/w) water. Optionally, each of the batches comprises solid dosage forms, tablets or capsules containing no more than 2.0% (w/w) water. In some embodiments, each of the batches comprises solid dosage forms, tablets or capsules containing no more than 1.95% (w/w) water. Optionally, each of the batches comprises solid dosage forms, tablets or capsules containing no more than 1.9% (w/w) water. In some embodiments, each of the batches comprises solid dosage forms, tablets or capsules containing no more than 1.85% (w/w) water. Optionally, each of the batches comprises solid dosage forms, tablets or capsules containing no more than 1.8% (w/w) water. In some embodiments, each of the batches comprises solid dosage forms, tablets or capsules containing no more than 1.75% (w/w) water. Optionally, each of the batches comprises solid dosage forms, tablets or capsules containing no more than 1.7% (w/w) water. In some embodiments, each of the batches comprises solid dosage forms, tablets or capsules containing no more than 1.65% (w/w) water. Optionally, each of the batches comprises solid dosage forms, tablets or capsules containing no more than 1.6% (w/w) water. In some embodiments, each of the batches comprises solid dosage forms, tablets or capsules containing no more than 1.55% (w/w) water. Optionally, each of the batches comprises solid dosage forms, tablets or capsules containing no more than 1.5% (w/w) water. In some embodiments, each of the batches comprises solid dosage forms, tablets or capsules containing no more than 1.45% (w/w) water. Optionally, each of the batches comprises solid dosage forms, tablets or capsules containing no more than 1.4% (w/w) water. In some embodiments, each of the batches comprises solid dosage forms, tablets or capsules containing no more than 1.35% (w/w) water. Optionally, each of the batches comprises solid dosage forms, tablets or capsules containing no more than 1.3% (w/w) water. In some embodiments, each of the batches comprises solid dosage forms, tablets or capsules containing no more than 1.25% (w/w) water. Optionally, each of the batches comprises solid dosage forms, tablets or capsules containing no more than 1.2% (w/w) water. In some embodiments, each of the batches comprises solid dosage forms, tablets or capsules containing no more than 1.15% (w/w) water. Optionally, each of the batches comprises solid dosage forms, tablets or capsules containing no more than 1.1% (w/w) water. In some embodiments, each of the batches comprises solid dosage forms, tablets or capsules containing no more than 1.05% (w/w) water. Optionally, each of the batches comprises solid dosage forms, tablets or capsules containing no more than 1.0% (w/w) water. In some embodiments, each of the batches comprises solid dosage forms, tablets or capsules containing no more than 0.95% (w/w) water. Optionally, each of the batches comprises solid dosage forms, tablets or capsules containing no more than 0.9% (w/w) water. In some embodiments, each of the batches comprises solid dosage forms, tablets or capsules containing no more than 0.85% (w/w) water. Optionally, each of the batches comprises solid dosage forms, tablets or capsules containing no more than 0.8% (w/w) water. In some embodiments, each of the batches comprises solid dosage forms, tablets or capsules containing no more than 0.75% (w/w) water. Optionally, each of the batches comprises solid dosage forms, tablets or capsules containing no more than 0.7% (w/w) water. In some embodiments, each of the batches comprises solid dosage forms, tablets or capsules containing no more than 0.65% (w/w) water. Optionally, each of the batches comprises solid dosage forms, tablets or capsules containing no more than 0.6% (w/w) water. In some embodiments, the water content of the tablets is determined by Karl Fischer titration, such as Karl Fischer Coulometric Titration Method 1c.

In some embodiments, each of the batches comprises solid dosage forms, such as tablets or capsules, containing between about 0.8% to about 2.2% (w/w) water. Optionally, each of the batches comprises solid dosage forms, such as tablets or capsules, containing between about 0.8% to about 2% (w/w) water. In some embodiments, each of the batches comprises solid dosage forms, such as tablets or capsules, containing between about 0.8% to about 1.9% (w/w) water. Optionally, each of the batches comprises solid dosage forms, such as tablets or capsules, containing between about 0.8% to about 1.8% (w/w) water. In some embodiments, the each of the batches comprises solid dosage forms, such as tablets or capsules, containing between about 0.8% to about 1.7% (w/w) water. Optionally, each of the batches comprises solid dosage forms, such as tablets or capsules, containing between about 0.8% to about 1.6% (w/w) water. In some embodiments, each of the batches comprises solid dosage, such as forms, tablets or capsules, containing between about 0.8% to about 1.5% (w/w) water. Optionally, each of the batches comprises solid dosage forms, such as tablets or capsules, containing between about 0.8% to about 1.4% (w/w) water. In some embodiments, each of the batches comprises solid dosage forms, such as tablets or capsules, containing between about 0.8% to about 1.3% (w/w) water. Optionally, each of the batches comprises solid dosage forms, such as tablets or capsules, containing between about 0.8% to about 1.2% (w/w) water. In some embodiments, each of the batches comprises solid dosage forms, such as tablets or capsules, containing contains between about 0.8% to about 1.1% (w/w) water. Optionally, each of the batches comprises solid dosage forms, such as tablets or capsules, containing between about 0.8% to about 1.0% (w/w) water.

In some embodiments, each of the batches comprises solid dosage forms, such as tablets or capsules, containing between about 1.0% to about 2.25% (w/w) water. Optionally, each of the batches comprises solid dosage forms, such as tablets or capsules, containing between about 1.0% to about 2.0% (w/w) water. In some embodiments, each of the batches comprises solid dosage forms, such as tablets or capsules, containing between about 1.0% to about 1.75% (w/w) water. Optionally, each of the batches comprises solid dosage forms, such as tablets or capsules, containing between about 1.0% to about 1.5% (w/w) water. In some embodiments, each of the batches comprises solid dosage forms, such as tablets or capsules, containing between about 1.0% to about 1.25% (w/w) water. Optionally, each of the batches comprises solid dosage forms, such as tablets or capsules, containing between about 1.25% to about 2.0% (w/w) water. In some embodiments, each of the batches comprises solid dosage forms, such as tablets or capsules, containing between about 1.25% to about 1.75% (w/w) water. Optionally, each of the batches comprises solid dosage forms, such as tablets or capsules, containing between about 1.25% to about 1.5% (w/w) water. In some embodiments, each of the batches comprises solid dosage forms, such as tablets or capsules, containing between about 1.5% to about 2.0% (w/w) water. Optionally, each of the batches comprises solid dosage forms, such as tablets or capsules, containing between about 1.5% to about 1.75% (w/w) water. In some embodiments, each of the batches comprises solid dosage forms, such as tablets or capsules, containing between about 1.75% to about 2.0% (w/w) water.

Methods of Treatment

A further aspect of the present disclosure provides a method for treating a bone-related disease, a calcium disorder, an inflammatory disease or a degenerative disease by administering a therapeutically effective amount of calcitonin to a subject in need thereof. In some embodiments, the calcitonin is administered as any of the above pharmaceutical solid dosage forms, tablets or capsules. In some embodiments, the calcitonin is administered at a dose of 100 μg to 1000 μg. For example, the calcitonin may be administered at a dose of 200 μg. Optionally, the calcitonin is administered once daily. The calcitonin may be administered with food. In some embodiments, the calcitonin is administered at night. In some embodiments, the calcitonin can be administered without food (e.g., several hours after the prior meal and/or before the next meal). In some embodiments, the calcitonin is administered twice daily (i.e., bis in die, b.i.d.). For example, the calcitonin may be administered at morning and at night.

In some embodiments, the bone-related disease is selected from the group consisting of osteoporosis, osteopenia, Paget's disease, pain associated with recent vertebral fragility fracture, pain associated with metastasis of the bone, and hypercalcemia of malignancy. In some embodiments, the inflammatory disease is selected from the group consisting of, but not limited to, osteoarthritis (OA), rheumatoid arthritis (RA), juvenile rheumatoid arthritis (JRA), and ankylosing spondylitis (AS).

In some embodiments, the subject is a mammal. Optionally, the subject is a human patient. In some embodiments, the subject is a companion animal, such as a dog or a horse. Optionally, the method comprises identifying the subject in need thereof.

In some embodiments, the calcitonin pharmaceutical tablets of the present disclosure are administered in combination with a therapeutically effective amount of an additional therapeutic agent. The additional therapeutic agent may be a matrix metalloproteinase inhibitor (e.g., galardin or BB-94). In some embodiments, the additional therapeutic agent is an antibiotic, such as a tetracycline antibiotic (e.g., tetracycline, and doxycycline). Optionally, the additional therapeutic agent is an interleukin antagonist (e.g., anakinra). The additional therapeutic agent may be an aggrecanase inhibitor. In some embodiments, the additional therapeutic agent is a cyclooxygenase-2 (COX-2) inhibitor (e.g., valdecoxib, celecoxib etoricoxib, rofecoxib). Optionally, the additional therapeutic agent is a nonsteroidal anti-inflammatory drug (NSAID, e.g., aspirin, ibuprofen and naproxen).

In some embodiments, the additional therapeutic agent is selected from the group consisting of minocycline, doxycycline, oxytetracycline, enrofloxacin, ceftiofur, salinomycin, tetracycline, BB-94 (available from Tocris Bioscience as BATIMASTAT®), solimastat, Galardin (available from U.S. Biological as LLOMASTAT®), anakinra (available from Biovitrum as KINERET®), valdecoxib, celecoxib (available from Pfizer as CELEBREX®), etoricoxib, rofecoxib, aspirin, ibuprofen and naproxen (available from Bayer as ALEVE®).

EXAMPLES

In order that this disclosure be more fully understood, the following examples are set forth. These examples are for the purpose of illustration only and are not to be construed as limiting the scope of the disclosure in any way.

Example 1 Identification of Room Temperature Stable Tablets

Recombinant salmon calcitonin was manufactured into large batches of tablets, which demonstrated batch-to-batch variability in room temperature stability. Further analysis revealed that batches of tablets that exhibit lower stability at RT conditions over time (e.g., Batch 1) were determined to have higher water content. By comparison, tablets from room-temperature stable batches (e.g., Batch 4) had low water content (e.g., less than 2.5% (w/w) water, or even less than 2.2% (w/w) water). For example, Batch 1 tablets contained 2.80% (w/w) water, while Batch 4 tablets contained 1.95% (w/w) water. Accordingly, methods for controlling water content and consistently manufacturing batches of tablets with lower water content, and thus room temperature stability, were developed (see, Examples 2 and 3). The final tablet water content was influenced by both the water content of the tablet core following direct compression and the impact of the subsequent application of the water soluble sub-coat and outer enteric coat.

Tablets prepared as described herein to limit water content exhibited better room temperature stability than tablets having higher water content. See, e.g., FIG. 1. Batch 1 tablets contained 2.8% (w/w) water, while Batch 2 tablets contained 1.8% (w/w) water.

Figure 2:
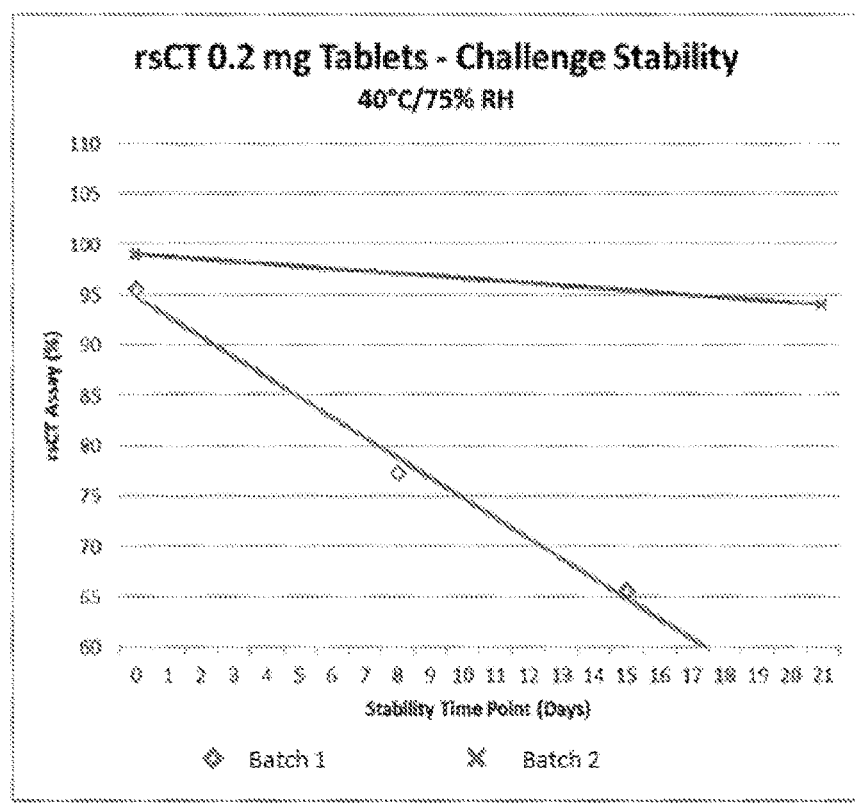
FIG. 2 demonstrates that accelerated challenge stability conditions (40° C. and 75% relative humidity) are predictive of tablets that will achieve room temperature stability. The results also demonstrate the marked difference in stability performance between batches containing higher water content (Batch 1, 2.80% water w/w) versus tablets manufactured using the methods outlined in the present patent application to limit water content (Batch 2) to no more than 2.5% w/w.

A short-term accelerated stability study was performed on one of the batches with good 25° C. stability and one of the batches with lower 25° C. stability. The short-term accelerated stability study was conducted at 40° C. and 75% RH for 21 days and showed definitive differences in stability as measured by the assay of rsCT between the batches. See, FIG. 2. The results of the study suggested that short-term accelerated stability could be used to identify batches with acceptable room temperature stability.

Example 2 Effect of Water Content on the Tablet Core

Figure 3:
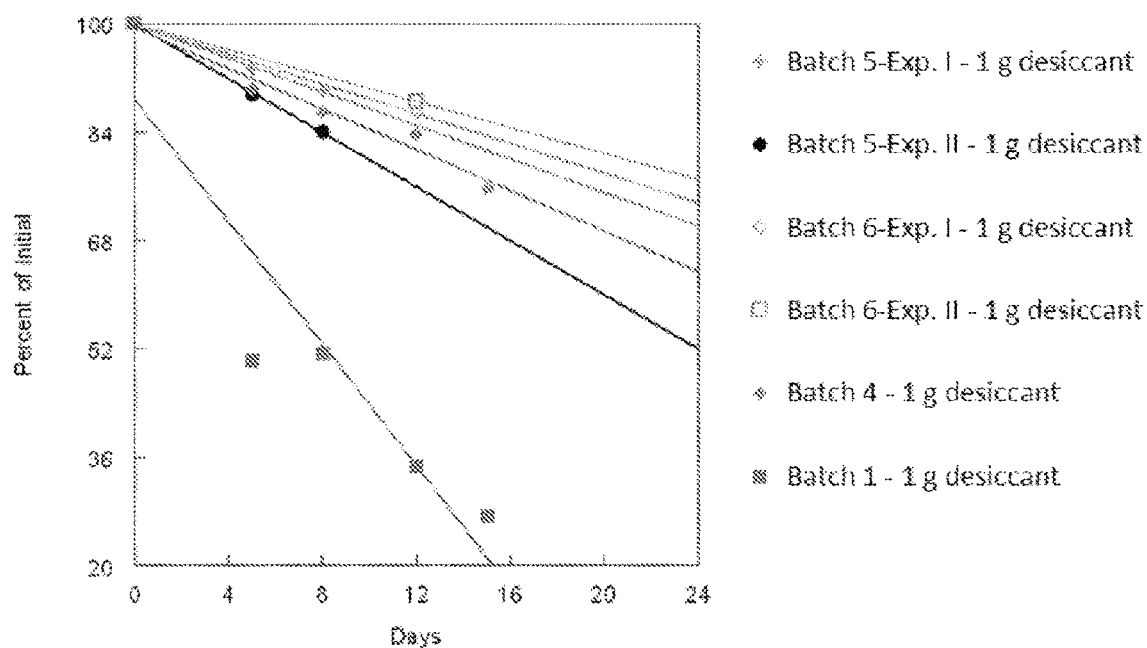
FIG. 3 depicts the stability of various batches of a tablet for oral delivery of calcitonin. Batch 5-Exp. I (1.94% water w/w), Batch 5-Exp. II (2.01% water w/w), Batch 6-Exp. I (1.82% water w/w), Batch 6-Exp. II (1.84% water w/w) and Batch 4 (1.95% water w/w) each demonstrated greater stability than Batch 1 (2.80% water w/w).

The stability of rsCT in the binary presence of the tablet core and subcoat excipients, as well as the effect of intrinsic and extrinsic moisture on the stability of those mixtures, was thoroughly examined. Each of the components including rsCT was evaluated in its untreated state and after drying in a lyophilizer (dried). The water content of each powder was determined by Karl Fischer Coulometric Titration Method 1c prior to preparation of the binary mixtures and is presented in Table 1, below.

TABLE 1

| Excipient Water Content for Binary Mixture Study | | |
|---|---|---|
| Material | Untreated Water Content | Dried Water content |
| rsCT | 8.91% | 0.90% |
| Citric Acid DC F20 | 0.39% | 0.12% |
| Polyplasdone XL-10 (Crospovidone) | 4.58% | 0.26% |
| Kollidon VA 64 (Copovidone) | 2.42% | 0.50% |
| Prosolv HD 90 | 4.41% | 0.25% |
| Magnesium Stearate | 5.00% | 3.51% |
| Kollicoat IR | 1.09% | 0.14% |

Binary mixtures were prepared by combining about 18 mg of rsCT with about 300 mg of each of the excipients, individually. Each binary mixture was evaluated in the presence or absence of 10% (w/w) water. Control samples included rsCT only. The mixtures were stored at 40° C., were pulled in duplicate after 7 days and 32 days, and were evaluated for recovery (assay activity relative to that of untreated and dried rsCT) and purity. The average results are summarized in Table 2, below.

TABLE 2

| Binary Mixture Results after 7 and 32 Days at 40° C. | | | | |
|---|---|---|---|---|
| | T = 7 days | | T = 32 days | |
| Binary Mixture | Average Recovery | Average Purity (Area %) | Average Recovery | Average Purity (Area %) |
| Untreated Powders | | | | |
| rsCT Only | 99.3% | 98.9% | 97.3% | 96.0% |
| rsCT/Citric Acid DC | 98.1% | 98.7% | 96.0% | 95.9% |
| rsCT/Polyplasdone | 101.3% | 98.9% | 98.0% | 96.7% |
| rsCT/Kollidon VA64 | 97.3% | 98.8% | 93.3% | 97.6% |
| rsCT/Prosolv HD90 | 99.8% | 99.1% | 97.7% | 97.7% |
| rsCT/Magnesium | 82.6% | 98.9% | 83.7% | 97.9% |
| rsCT/Kollicoat IR | 97.4% | 98.5% | 94.2% | 96.6% |
| 10% (v/w) Water Added | | | | |
| rsCT Only | 85.6% | 98.2% | 83.8% | 95.1% |
| rsCT/Citric Acid DC | 24.2% | 32.5% | 3.2% | 9.2% |
| rsCT/Polyplasdone | 100.9% | 98.7% | 98.2% | 96.7% |
| rsCT/Kollidon VA64 | 93.8% | 98.7% | 90.8% | 96.7% |
| rsCT/Prosolv HD90 | 23.4% | 67.2% | 15.6% | 49.1% |
| rsCT/Magnesium | 51.5% | 75.1% | 19.2% | 40.7% |
| rsCT/Kollicoat IR | 72.6% | 87.9% | 50.3% | 70.2% |

These results demonstrate the negative impact of water content on the RT stability profile of the final tablet. All excipients were individually compatible with rsCT if dry, when recovery and purity were measured over 7 and 32 days of storage at 40° C. In the presence of water, rsCT rapidly degraded with concomitant loss of recovery and purity in the presence of Citric Acid DC F20. In the presence of water, there was a rapid loss of rsCT activity and non-concomitant loss in purity in the presence of Prosolv HD90. In the presence of water, there was a loss of rsCT activity and loss in purity in the presence of Kollicoat IR. Attention to starting water content of the tablet components and limiting water ingress into the tablet core were key parameters to achieve RT stability.

This binary compatibility study demonstrated that under a dry blend and direct compression manufacture process, all of the excipients identified for this formulation were compatible with rsCT when they met water content specifications. Moisture penetration of the core during the coating process may have a negative impact on long term stability. The interaction between Prosolv and rsCT in the presence of water at elevated temperature was the most probable cause of assay loss, not degradation, during the real time stability studies.

Example 3 Effect of Coating Process on Water Content and Tablet Stability

Initial attention relating to water content was focused on the excipients and rsCT; once specifications were established for tablet water content the attention was re-focused on the method of the water soluble sub-coat application. Production of acceptable tablets cores could be undermined if the water soluble sub-coat was not applied properly. Therefore improvement of the tablet coating parameters was initiated.

A small scale batch split into two portions using a 30 inch coating pan tested this theory by controlling the process such that the only difference in manufacture was the conditions for sub-coating (see, Table 3, below). Both sub-coating approaches yielded low water content of in-process material and finished product, compared to the poorer performing batch (Batch 1, see Table 4, below).

TABLE 3

| Comparison of Sub-Coat Spray Parameters | | |
|---|---|---|
| | Batch 5 | |
| | Experiment I | Experiment II |
| Inlet Temp (° C.) | 53-64 | 58-61 |
| Exhaust Temp (° C.) | 48-51 | 44-47 |
| Product Temp (° C.) | 48-51 | 43-45 |
| First Spray rate (g/min/kg) | 1.000 | 2.290 |
| Total Time for Sub-Coat Application (minutes) | 384 | 130 |

TABLE 4

| Water Content Comparison of Various Batches | |
|---|---|
| Batch | Water Content (% w/w) |
| Batch 1 | 2.80% |
| Batch 4 | 1.95% |
| Batch 5 Experiment I | In-process Sub-Coated Core = 1.59%<br>Final Enteric Coated tablet = 1.94% |
| Batch 5 Experiment II | In-process Sub-Coated Core = 2.11%<br>Final Enteric Coated tablet = 2.01% |

After enteric coating, the batches were packaged into 30 count high density polyethylene (HDPE) bottles with desiccant and placed on accelerated stability (50° C. and 71% RH for 24 days). Assay results from accelerated stability testing of finished product from both experimental sub-coating application processes showed improved results compared to Batch 1 that demonstrated poor room temperature stability and comparable or better stability to Batch 4 that showed acceptable room temperature stability (FIG. 3). The results from this experiment suggested that the water content of the tablet cores needs to be controlled during the coating process, and that the sub-coating conditions must be controlled to assure an acceptable level for the water content of the tablets.

With data confirming that the coating conditions for sub-coat application can have an impact on tablet stability on accelerated stability, a second study was conducted. The coating times for the two sub-coating experiments (Batch 5 experiment I and experiment II) were lengthy. In an attempt to decrease the sub-coating application time, the next coating experiment used a 65 kg (77,225 tablets) batch (Batch 6). The experiment evaluated a two tiered weight gain approach to the sub-coat application process. The batch was blended, compressed and divided into approximately two 31 kg sub-lots A and B. The coating experiments were performed using an O'Hara 30 inch coating pan. Application of the sub-coat was slow at the start of the process by using a low spray rate established in Batch 5 experiment I until a specified tablet weight gain, either 0.25% or 0.5% for the sub-coat was achieved (Batch 6 experiment I and II, respectively), then the spray rate was increased for the rest of the process. Both batches were then enteric coated using the same coating process variables. The water content values for the two batches are listed in Table 5, below.

TABLE 5

Water Content Comparison Batch 6 Experiments I and II

| Batch | Weight Gain before spray rate increase | Water Content (% w/w) |
| --- | --- | --- |
| Batch 6 Experiment I | 0.25% | Final Enteric Coated tablet = 1.82% |
| Batch 6 Experiment II | 0.5% | Final Enteric Coated tablet = 1.84% |

The two enteric coated sub-lots were packaged into HDPE bottles with 1 gram desiccant and placed on accelerated stability (50° C. and 71% RH for 24 days). Comparing the accelerated stability test results to the prior batches showed both sub-lots (Experiments A and B), to have stability similar to Batch 4, which had shown good room temperature stability. The assay data show both approaches to the sub-coating processes yielded comparable assay results to the previous Batch 5 Experiment I (FIG. 3).

The process was scaled-up to a 100.621 kg (125,000 tablets) batch. See, Table 6, below. Batch 7 replicated the two tier sub-coat process established in the previous coating experiment using an O'Hara 48 inch coating pan. The sub-coating parameters were scaled up from the 30 inch coating conditions. After the tablets were enteric coated, they were packaged into HDPE bottles with 1 gram of desiccant and placed on accelerated stability. Water content of finished product was found to be higher than previously seen in the 30 inch pan coating experiments suggesting that the scaled-up coating parameters needed adjusting, in particular the spray rate needed to be slower. See, Table 7, below.

The next 100.621 kg scale-up batch (Batch 8) utilized a reduction in spray rate for both sub-coat and enteric coat process, unsuccessfully. See, Table 6, below. Defects in appearance of the tablet coating were found in finished product after enteric coating. Investigation into this coating appearance failure identified a disparity between the qualified flow rates for the spray nozzle being used and the targeted spray rates for the sub-coat and enteric-coat processes. The targeted flow rates used up to this point were below the acceptable flow rates specified for the nozzle. With the slow flow rates for these processes being below the acceptable operational range for this nozzle diameter size, the performance of the spray guns was poor which had a direct impact on the tablet appearance, coating process, and water uptake of the tablet core during the coating process. See, Table 7, below. A reduced spray gun orifice was selected for sub-coat application in a 48-inch pan (Batch 9) and showed improved tablet appearance and water uptake of the tablet core. See, Table 7, below. It is within the skill of the art to select the appropriate spray nozzle for other spray coaters (e.g., a spray coater with a 60-inch pan).

TABLE 6

Comparison of Sub Coat (Kollicoat) parameters for Full Scale Batches of Salmon Calcitonin Tablets Delayed release 0.2 mg

| Batch # | Batch 7 | Batch 8 | Batch 9 |
| --- | --- | --- | --- |
| Nozzle Size | Original | Original | Reduced |
| First Spray Inlet Temperature (° C.) | 57-62 | 57-62 | 57-62 |
| First Spray Exhaust Temperature (° C.) | 48-53 | 48-53 | 48-53 |
| First Spray Product Temperature (° C.) | 47-52 | 47-52 | 47-52 |
| Relative Spray Rate[1] | 1.0 | 0.79 | 0.75 |
| Weight Gain @ Spray Rate Change | 0.49 | 1.3 | 0.6 |
| Second Spray Inlet Temperature (° C.) | 57-62 | 57-62 | 57-62 |
| Second Spray Exhaust Temperature (° C.) | 45-50 | 45-50 | 45-50 |
| Second Spray Product Temperature (° C.) | 43-48 | 43-48 | 43-48 |
| Relative Spray Rate[1] | 1.88 | 1.25 | 1.41 |
| Fold-increase in Spray Rate | 1.88 | 1.58 | 1.87 |
| Final Weight gain (%) | 6.14 | 6.11 | 6.04 |
| Total Time for Sub-Coat Application (minutes) | 120 | 125 | 191 |

[1]Typically, spray rates are reported in g/min/kg. To highlight the relative change in spray rates, the spray rates in Table 6 are being reported as relative spray rates, with the rate of the first spray of Batch 7 set to 1.0.

TABLE 7

Finished Product Water Content

| Batch Number | Water Content (%) |
| --- | --- |
| Batch 5 - Experiment I | 1.94% |
| Batch 5 - Experiment II | 2.02% |
| Batch 6 - Experiment I | 1.82% |
| Batch 6 - Experiment II | 1.89% |
| Batch 7 | 2.34% |
| Batch 8 | 2.06% |
| Batch 9 | 1.75% |

The coating experiments described above resulted in optimization of the sub-coating processes for salmon calcitonin delayed release tablets. Improved stability at elevated temperatures were achieved by lowering the residual water content found in the finished product.

What is claimed:

1. A method for preparing a tablet for oral delivery of calcitonin comprising:
   (a) dry blending calcitonin, silicified microcrystalline cellulose, coated citric acid, copovidone, crospovidone, and magnesium stearate;
   (b) compressing the blended mixture into a tablet core;
   (c) applying a water-soluble barrier layer in an initial spray at a first spray rate sufficient to add approximately 0.25% (w/w) to the tablet core in about 30 minutes at an average product temperature of at least 45° C.; and
   (d) applying an enteric coating.

2. A method for spray coating a tablet core for oral delivery of calcitonin comprising:
   (a) providing a tablet core;
   (b) applying a water-soluble barrier layer in an initial spray at a first spray rate sufficient to add approximately 0.25% (w/w) of the water-soluble barrier layer to the tablet core in about 30 minutes at an average product temperature of at least 45° C.; and
   (c) applying an enteric coating.

3. The method of claim 2, wherein the tablet core comprises
   (a) calcitonin intermixed with coated citric acid particles;
   (b) crospovidone;
   (c) copovidone;
   (d) microcrystalline cellulose; and
   (e) magnesium stearate.

4. The method of claim 3, wherein the microcrystalline cellulose is silicified microcrystalline cellulose.

5. The method of claim 1, wherein the tablet core comprises
   (a) about 0.01% (w/w) to about 0.10% (w/w) salmon calcitonin;
   (b) about 62% (w/w) maltodextrin-coated citric acid;
   (c) about 1.1% (w/w) crospovidone;
   (d) about 5% (w/w) copovidone;
   (e) about 31% (w/w) silicified microcrystalline cellulose; and
   (f) about 0.5% (w/w) magnesium stearate.

6. The method of claim 5, wherein the tablet core comprises about 0.02% (w/w) salmon calcitonin.

7. The method of claim 1, wherein the first spray rate is sufficient to add approximately 0.5% (w/w) of the water-soluble barrier layer to the tablet core in about 30 minutes.

8. The method of claim 1, wherein after applying the water-soluble barrier layer at the first spray rate for at least 30 minutes, the water-soluble barrier layer is applied in a subsequent spray at a second spray rate, which is faster than the first spray rate.

9. The method of claim 8, wherein the second spray rate is sufficient to add about 5.5% (w/w) of the water-soluble barrier layer to the tablet core in about two hours to about four and a half hours.

10. The method of claim 8, wherein the method comprises applying the water-soluble barrier layer at the first spray rate until about 0.5% (w/w) to about 2.0% (w/w) of the water-soluble barrier layer is added to the tablet core and then applying the water-soluble barrier layer at the second spray rate.

11. The method of claim 10, wherein the water-soluble barrier layer is applied at the second spray rate until a total of about 3.0% (w/w) to about 7.0% (w/w) of the water-soluble barrier layer is added to the tablet core.

12. The method of claim 2, wherein the average product temperature during the initial spray is at least 46° C. to at least 50° C.

13. The method of claim 1, wherein the minimum product temperature during the initial spray is at least 45° C.

14. The method of claim 1, wherein the enteric coating adds about 6% to about 8% to the weight of the tablet, including the tablet core and the water-soluble barrier layer.

15. The method of claim 2, wherein after applying the water-soluble barrier layer at the first spray rate for at least 30 minutes, the water-soluble barrier layer is applied in a subsequent spray at a second spray rate, which is faster than the first spray rate.

16. The method of claim 15, wherein the second spray rate is sufficient to add about 5.5% (w/w) of the water-soluble barrier layer to the tablet core in about two hours to about four and a half hours.

17. The method of claim 15, wherein the method comprises applying the water-soluble barrier layer at the first spray rate until about 0.5% (w/w) to about 2.0% (w/w) of the water-soluble barrier layer is added to the tablet core and then applying the water-soluble barrier layer at the second spray rate.

18. The method of claim 17, wherein the water-soluble barrier layer is applied at the second spray rate until a total of about 3.0% (w/w) to about 7.0% (w/w) of the water-soluble barrier layer is added to the tablet core.

19. The method of claim 2, wherein the average product temperature during the initial spray is at least 46° C. to at least 50° C.

20. The method of claim 2, wherein the minimum product temperature during the initial spray is at least 45° C.

* * * * *